United States Patent [19]

Takaya et al.

[11] 4,294,960
[45] Oct. 13, 1981

[54] 7-[2-(2-AMINOTHIAZOL-4-YL)-2-CYCLOPENTYLOXYIMINOACETAMIDO]-3-CEPHEM-4-CARBOXYLIC ACID (SYNISOMER)

[75] Inventors: Takao Takaya, Kawanishi; Hisashi Takasugi, Kohamanishi; Toshiyuki Chiba, Iwami; Kiyoshi Tsuji, Nagai-cho-naka, all of Japan

[73] Assignee: Fujisawa Pharmaceutical Co., Ltd., Osaka, Japan

[21] Appl. No.: 123,481

[22] Filed: Feb. 21, 1980

Related U.S. Application Data

[63] Continuation-in-part of Ser. No. 886,340, Mar. 14, 1978.

[30] Foreign Application Priority Data

Mar. 14, 1977 [GB] United Kingdom ............... 10699/77
Jul. 12, 1977 [GB] United Kingdom ............... 29245/77
Nov. 11, 1977 [GB] United Kingdom ............... 42315/77

[51] Int. Cl.$^3$ ............................................. C07D 501/22
[52] U.S. Cl. .................................... 544/22; 424/246; 544/28
[58] Field of Search .......................................... 544/22

[56] References Cited

U.S. PATENT DOCUMENTS 4,098,888  7/1978  Ochiai et al. ................. 424/246
4,205,072  5/1980  Vignau et al. ................. 424/246

Primary Examiner—Paul M. Coughlan, Jr.
Attorney, Agent, or Firm—Oblon, Fisher, Spivak, McClelland & Maier

[57] ABSTRACT

The invention relates to new thiadiazolyl or thiazolyl-substituted cephem and cepham compounds, the pharmaceutically acceptable salts and bioprecursors thereof, of antimicrobial activity, processes for preparation thereof, intermediates for preparing the new compounds and to pharmaceutical compositions comprising the new compounds, and methods of using the compositions for treatment of infectious diseases.

1 Claim, No Drawings

7-[2-(2-AMINOTHIAZOL-4-YL)-2-CYCLOPENTYLOXYIMINOACETAMIDO]-3-CEPHEM-4-CARBOXYLIC ACID (SYNISOMER)

This application is a continuation-in-part of parent application Ser. No. 886,340, filed Mar. 14, 1978.

This invention relates to new cephem and cepham compounds. More particularly, it relates to new 7-substituted-3-cephem(or cepham)-4-carboxylic acid, its pharmaceutically acceptable salt and pharmaceutically acceptable bioprecursor thereof, which have antimicrobial activities, and processes for preparation thereof, to intermediate for preparing the same and processes for preparation thereof, and to pharmaceutical composition comprising the same and methods of using the same prophylactically and therapeutically for treatment of infectious diseases in human being and animals.

Accordingly, the objects of this invention are to provide:
new 7-substituted-3-cephem(or cepham)-4-carboxylic acid, its pharmaceutically acceptable salt and pharmaceutically acceptable bioprecursor thereof, which exhibit excellent antimicrobial activities against a wide variety of pathogenic microorganisms including Gram negative and Gram positive bacteria,
processes for preparation of the same,
pharmaceutical composition comprising one of the same as an active ingredient, and
a method of using the same prophylactically and therapeutically for treatment of infectious diseases caused by pathogenic microorganisms in human being and animals; and further
intermediate to be used for preparation of pharmaceutically active 7-substituted-3-cepham(or cephem)-4-carboxylic acid, its pharmaceutically acceptable salt or pharmaceutically acceptable bioprecursor thereof, and
methods for preparation of the same.

The cephem and cepham compounds provided by this invention can be represented by the formula (I):

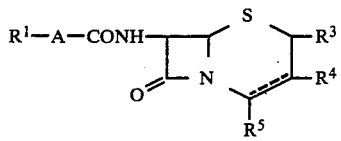

wherein
$R^1$ is thiadiazolyl, thiazolyl of the formula:

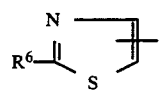

in which $R^6$ is amino or protected amino, or haloacetyl,
A is methylene or a group of the formula:

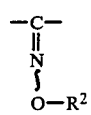

in which $R^2$ is hydrogen or an aliphatic hydrocarbon residue which may be substituted with halogen, carboxy or esterified carboxy, $R^3$ is hydrogen or lower alkyl,
$R^4$ is hydrogen, halogen, lower alkyl or a group of the formula: —O—$R^7$ in which $R^7$ is hydrogen, lower alkyl or acyl,
$R^5$ is carboxy or functionally modified carboxy, and
the dotted line represents 3-cephem and cepham nuclei, inclusively,
provided that
(i) $R^4$ is hydrogen, halogen or a group of the formula: —O—$R^7$ in which $R^7$ is as defined above, when $R^3$ is hydrogen,
(ii) $R^4$ is lower alkyl, when $R^3$ is lower alkyl,
(iii) A is a group of the formula:

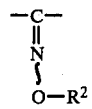

in which $R^2$ is as defined above, when $R^1$ is thiadiazolyl or thiazolyl of the formula:

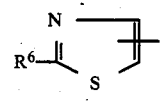

in which $R^6$ is as defined above, and
(iv) the dotted line represents 3-cephem nucleus and $R^4$ is hydrogen, halogen, lower alkyl or —O$R^7$ in which $R^7$ is lower alkyl, when $R^1$ is haloacetyl.

It is to be noted that the cephem and cepham compounds (I) as illustrated above include a compound useful as an antimicrobial agent and also a compound useful as an intermediate for preparing the above antimicrobial agent, particularly as illustrated below.

The compound useful as an antimicrobial agent can be represented by the formula (I'):

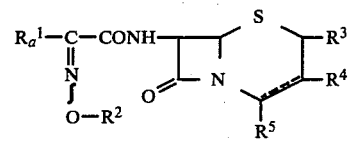

wherein
$R_a^1$ is thiadiazolyl or thiazolyl of the formula:

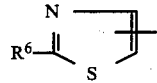

in which $R^6$ is as defined above, and
$R^2$, $R^3$, $R^4$ and $R^5$ are each as defined above.

On the other hand, the compound useful as an intermediate for preparing the above compound (I') can be represented by the formula (I''):

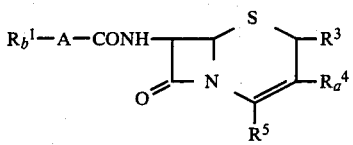

wherein $R_b^1$ is haloacetyl, $R_a^4$ is hydrogen, halogen, lower alkyl or a group of the formula: —O—$R^7$ in which $R^7$ is lower alkyl, and $R^3$, $R^5$ and A are each as defined above.

And further, it is to be noted that the compound (I') where $R_a^1$ is thiazolyl of the formula:

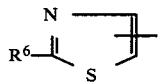

in which $R^6$ is protected amino, $R^4$ is a group of the formula: —O—$R^7$ in which $R^7$ is hydrogen or acyl and/or $R^5$ is functionally modified carboxy is also useful as an intermediate for preparing the more active compound as explained below.

Accordingly, the more preferred active compound can be represented by the formula (I'''):

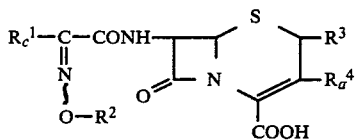

(I''')

wherein $R_c^1$ is thiadiazolyl or thiazolyl of the formula:

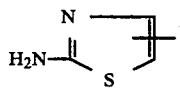

and $R^2$, $R^3$ and $R_a^4$ are each as defined above.

The terms and definitions described in this specification and claims are illustrated as follows.

(a) Partial structure of the formula:

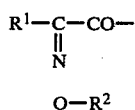

is intended to mean both of the geometrical formulae:

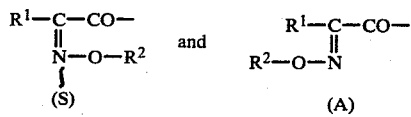

The geometry of the formula (S) is referred to as "syn" and another formula (A) is referred to as "anti".

Accordingly, one isomer of the compound having the partial structure shown by the above formula (S) is referred to as "syn isomer" and another isomer of the compound having the alternative one shown by the above formula (A) is referred to as "anti isomer", respectively.

From the view point of structure-activity relationship, it is to be noted that a syn isomer of the compound (I') tends to be of much higher antimicrobial activity than the corresponding anti isomer, and accordingly the syn isomer of the compound (I') is more preferable antimicrobial agent than the corresponding anti isomer in the prophylactic and therapeutic value.

(b) The thiazolyl group of the formula:

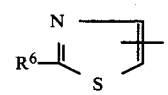

(wherein $R^6$ is as defined above) is well known to lie in tautomeric relation with a thiazolinyl group of the formula:

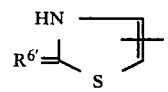

(wherein $R^{6'}$ is imino or protected imino).

The tautomerism between the said thiazolyl and thiazolinyl groups can be illustrated by the following equilibrium:

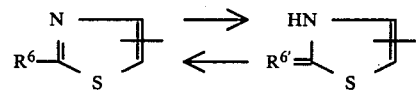

(wherein $R^6$ and $R^{6'}$ are each as defined above).

Accordingly, it is to be understood that both of the said groups are substantially the same, and the tautomers consisting of such groups are regarded as the same compounds, especially in the manufacturing chemistry. Therefore, both of the tautomeric forms of the compounds having such groups in their molecule are included in the scope of this invention and designated inclusively with one expression "thiazolyl" and represented by the formula:

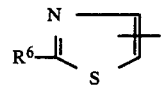

(wherein $R^6$ is as defined above) only for the convenient sake throughout this specification and claims.

(c) It is well known that the 3-hydroxy-3-cephem compound having the partial structure of the formula:

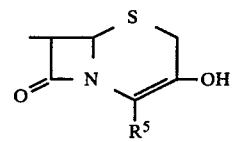

lies in a tautomeric relation with the 3-oxo-cepham compound of the formula:

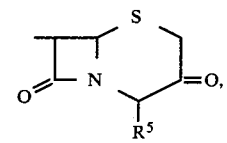

each of which is referred to as the enol- or keto-tautomer, and that the enol-tautomer is usually the stabilized one.

Accordingly, both of the compounds having such tautomeric structures are included within the same scope of the compound, and therefore, the structure and nomenclature of such tautomers are expressed inclusively with one expression of the stabilized enol tautomer, i.e. 3-hydroxy-3-cephem compound throughout this specification and claims.

In the above and subsequent descriptions of this specification, suitable examples and illustration of the various definitions which this invention intends to include within the scope thereof are explained in detail as follows.

The term "lower" is used to intend a group having 1 to 6 carbon atoms, unless otherwise provided.

"Thiadiazolyl" for $R^1$ may be 1,2,3-thiadiazolyl (e.g 1,2,3-thiadiazol-4-yl or 1,2,3-thiadiazol-5-yl), 1,3,4-thiadiazolyl or 1,2,4-thiadiazolyl, preferably 1,2,3-thiadiazolyl, and more preferably 1,2,3-thiadiazol-4-yl.

"Aliphatic hydrocarbon residue" for $R^2$ may include a monovalent radical of a saturated or unsaturated, and straight, branched or cyclic aliphatic hydrocarbon, and particularly may include alkyl, alkenyl, alkynyl, cycloalkyl and the like, the details of which are explained below.

"Alkyl" may include a residue of straight or branched alkane having 1 to 12 carbon atoms such as methyl, ethyl, propyl, isopropyl, butyl, isobutyl, t-butyl, pentyl, neopentyl, hexyl, heptyl, octyl, nonyl, decyl, undecyl, dodecyl and the like, preferably lower alkyl, and more preferably the one having 1 to 4 carbon atoms.

"Alkenyl" may include a residue of a straight or branched alkene having up to 12 carbon atoms, preferably lower alkenyl such as vinyl, allyl, 1-propenyl, isopropenyl, butenyl, isobutenyl, pentenyl, hexenyl and the like, and more preferably the ones having up to 4 carbon atoms.

"Alkynyl" may include a residue of a straight or branched alkyne having up to 12 carbon atoms, preferably lower alkynyl such as ethynyl, propargyl, 1-propynyl, 3-butynyl, 2-butynyl, 4-pentynyl, 3-pentynyl, 2-pentynyl, 1-pentynyl, 5-hexynyl and the like, and more preferably the ones having up to 4 carbon atoms.

"Cycloalkyl" may include a residue of a cycloalkane having up to 8 carbon atoms, preferably lower cycloalkyl such as cyclopropyl, cyclobutyl, cyclopentyl and cyclohexyl, and more preferably cyclohexyl.

These aliphatic hydrocarbon residues may be substituted with halogen atom(s), carboxy or esterified carboxy group(s). Accordingly, "aliphatic hydrocarbon residue substituted with halogen atom(s), carboxy or esterified carboxy group(s)" can also be alternatively expressed as "halogen-substituted aliphatic hydrocarbon residue", "carboxy-substituted aliphatic hydrocarbon residue" and "esterified carboxy-substituted aliphatic hydrocarbon residue", respectively, which may include more particularly halo-alkyl, alkenyl, alkynyl and cycloalkyl; carboxy-alkyl, alkenyl, alkynyl and cycloalkyl; and esterified carboxy-alkyl, alkenyl, alkynyl and cycloalkyl, respectively.

Suitable examples of the "halogen" may include chlorine, bromine, iodine and fluorine; suitable examples of the "esterified carboxy" may be alkoxycarbonyl or the like; and preferred examples of the "alkyl", "alkenyl", "alkynyl", "cycloalkyl" and alkyl moiety of the "alkoxycarbonyl" are the corresponding "lower" ones as mentioned above.

Preferred examples of the "halo-alkyl, alkenyl, alkynyl and cycloalkyl" may be chloromethyl, bromomethyl, iodomethyl, fluoromethyl, trichloromethyl, trifluoromethyl, 2-chloroethyl, 1,2-dichloroethyl, 2,2,2-trifluoroethyl, 3-chloropropyl, 4-iodobutyl, 5-fluoropentyl, 6-bromohexyl, 3-fluoroallyl, 3-chloropropargyl, 4-fluorocyclohexyl, or the like.

Preferred examples of the "carboxy-alkyl, alkenyl, alkynyl and cycloalkyl" may be carboxymethyl, 1-carboxyethyl, 2-carboxyethyl, 1-carboxypropyl, 3-carboxypropyl, 4-carboxybutyl, 5-carboxypentyl, 6-carboxyhexyl, 1-carboxyisopropyl, 1-ethyl-1-carboxyethyl, 2-methyl-2-carboxypropyl, 3-carboxyallyl, 3-carboxypropargyl, 4-carboxycyclohexyl, or the like.

Preferred examples of the "esterified carboxyalkyl, alkenyl, alkynyl and cycloalkyl" may be lower alkoxycarbonyl(lower)alkyl (e.g. methoxycarbonylmethyl, ethoxycarbonylmethyl, propoxycarbonylmethyl, t-butoxycarbonylmethyl, 2-ethoxycarbonylethyl, 2-ethoxycarbonylpropyl, 4-ethoxycarbonylbutyl, 1-t-butoxycarbonylisopropyl, 1-t-butoxycarbonyl-1-methylpropyl, 4-t-butoxycarbonylbutyl, 5-t-butoxycarbonylpentyl, 6-butoxycarbonylhexyl, etc.), lower alkoxycarbonyl(lower)alkenyl (e.g. 3-methoxycarbonylallyl, etc.), lower alkoxycarbonyl(lower)alkynyl (e.g. 3-methoxycarbonylpropargyl, etc.), lower alkoxycarbonyl(lower)cycloalkyl (e.g. 4-methoxycarbonylcyclohexyl, etc.) or the like, and more preferably lower alkoxycarbonylmethyl as exemplified above.

"Lower alkyl" for $R^3$, $R^4$ and $R^7$ is to be referred to those as exemplified in the term of the aliphatic hydrocarbon residue for $R^2$, preferably may be the ones having up to 4 carbon atoms and more preferably methyl.

"Halogen" for $R^4$ may be chlorine, bromine, iodine or fluorine, and preferred one is chlorine or bromine.

"Acyl" for $R^7$ may be lower alkanoyl (e.g. formyl, acetyl, propionyl, butyryl, isobutyryl, isovaleryl, pivaroyl, etc.), aroyl (e.g. benzoyl, etc.), lower alkanesulfonyl (e.g. mesyl, ethanesulfonyl, 1-methylethanesulfonyl, propanesulfonyl, butanesulfonyl, etc.), arenesulfonyl (e.g. benzenesulfonyl, tosyl, etc.) or the like.

"Protective groups" in the "protected amino" for $R^6$ may be the conventional N-protective group such as substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.) tetrahydropyranyl, substituted phenylthio, substituted alkylidene, substituted aralkylidene, substituted cycloalkylidene, acyl, or the like.

Suitable acyl for the protective group may be substituted or unsubstituted lower alkanoyl (e.g. formyl, acetyl, chloroacetyl, trifluoroacetyl, etc.), substituted or unsubstituted lower alkoxycarbonyl (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, trichloroethoxycarbonyl, 2-pyridylmethoxycarbonyl, etc.), substituted or unsubstituted ar(lower)alkoxycarbonyl (e.g. benzyloxycarbonyl, benzhydryloxycarbonyl, 4-nitrobenzyloxycarbonyl, etc.), lower cycloalkoxycarbonyl (e.g. cyclopentyloxycarbonyl, cyclohexyloxycarbonyl, etc.), 8-quinolyloxycarbonyl, succinyl, phthaloyl, or the like.

And further, the reaction product is a silan, boron, aluminium or phosphorus compound with the amino group may also be included in the protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

"Functionally modified carboxy" for $R^5$ may be an ester, amide or the like.

Suitable examples of the ester may be alkyl ester (e.g. methyl ester, ethyl ester, propyl ester, isopropyl ester, butyl ester, isobutyl ester, t-butyl ester, pentyl ester, t-pentyl ester, hexyl ester, heptyl ester, octyl ester, 1-cyclopropylethyl ester, etc.);

alkenyl ester (e.g. vinyl ester, allyl ester, etc.);

alkynyl ester (e.g. ethynyl ester, propynyl ester, etc.);

alkoxyalkyl ester (e.g. methoxymethyl ester, ethoxymethyl ester, isopropoxymethyl ester, 1-methoxyethyl ester, 1-ethoxyethyl ester, etc.);

alkylthioalkyl ester (e.g. methylthiomethyl ester, ethylthiomethyl ester, ethylthioethyl ester, isopropylthiomethyl ester, etc.);

haloalkyl ester (e.g. 2-iodoethyl ester, 2,2,2-trichloroethyl ester, etc.);

alkanoyloxyalkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, palmitoyloxymethyl ester, etc.);

alkanesulfonylalkyl ester (e.g. mesylmethyl ester, 2-mesylethyl ester, etc.);

substituted or unsubstituted aralkyl ester (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

substituted or unsubstituted aryl ester (e.g. phenyl ester, tolyl ester, t-butylphenyl ester, xylyl ester, mesityl ester, cumenyl ester, salicyl ester, etc.);

an ester with a silyl compound such as trialkylsilyl compound, dialkylalkoxysilyl compound or trialkoxysilyl compound, for example, trialkylsilyl ester (e.g. trimethyl silyl ester, triethylsilyl ester, etc.), dialkylalkoxy silyl ester (e.g. dimethylmethoxysilyl ester, dimethylethoxysilyl ester, diethylmethoxysilyl ester, etc.) or trialkoxysilyl ester (e.g. trimethoxysilyl ester, triethoxysilyl ester, etc.) or the like.

With regard to the terms "protected amino" for $R^6$ and "functionally modified carboxy" for $R^5$, it is to be understood that these groups bear the meaning not only in synthetic manufacture of the object compound by chemical process(es), but also in physiological and pharmaceutuical properties of the object compound per se.

That is, in the meaning of the synthetic manufacture, free amino group for $R^6$ and/or free carboxy group for $R^5$ may be transformed into the "protected amino" and/or "functionally modified carboxy" as mentioned above before conducting the process(es) for preventing any possible undesired side reaction(s), and the "protected amino" and/or "functionally modified carboxy" group in the resultant compound may be transformed into free amino and/or carboxy group after the reaction is conducted. This will be apparent from the explanation of the processes in the following.

On the other hand, in the meaning of the physiological and pharmaceutical properties of the object compound, the compound bearing the "protected amino" and/or "functionally modified carboxy" group is optionally used for improving the properties such as solubility, stability, absorbability, toxicity of the particularly active object compound bearing the free amino and/or carboxy group.

Suitable "pharmaceutically acceptable salt" of the object compound (I') may be conventional non-toxic salt, and may include a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a slat with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like.

It is well known in the pharmaceutical field that the active drug, when it has any undesired physiological or pharmaceutical property such as solutility, stability, absorbability, etc., is converted into modified derivative thereof for improving such undesired properties, and then said derivative, upon administration to a patient, exhibits the active efficacy by being converted in the body to the parent drug. In this meaning, the term "pharmaceutically acceptable bioprecursor" used throughout this specification and claim is intended to fundamentally mean all of the modified derivatives, which have structural formulae different from those of the active compounds of this invention, but are converted in the body to the active compounds of this invention upon administration, and also to mean the derivatives which are sometimes derived physiologically from the compounds of this invention in the body and exhibit antimicrobial efficacy.

The compounds (I) of this invention can be prepared by processes as shown in the following scheme.

Process A: N-Acylation

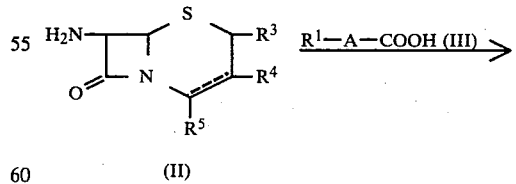

(II)

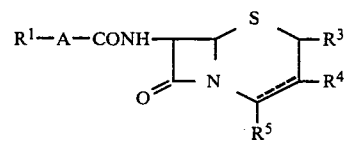

(I)

Process B: C-Nitrosation

-continued
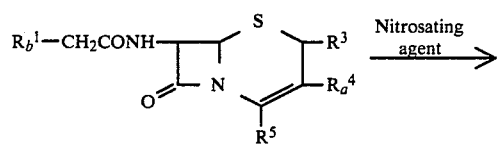
(IV)
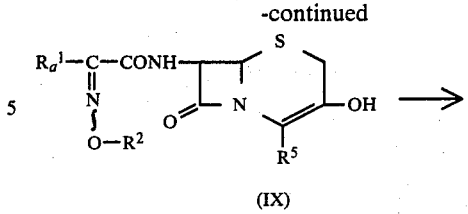
(IX)
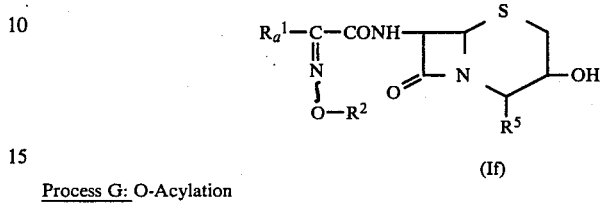
(If)
(Ib)
Process C: Etherification
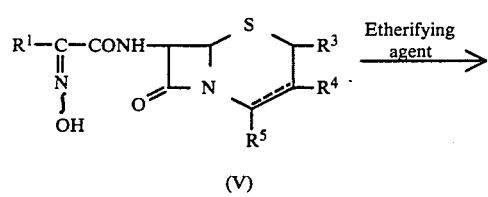
(V)
Process G: O-Acylation
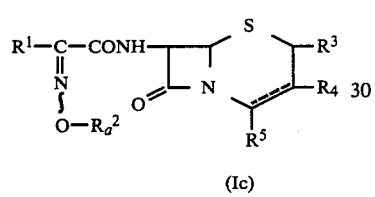
(If)
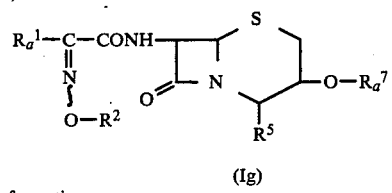
(Ig)
(Ic)
Process D: Thiazole ring formation
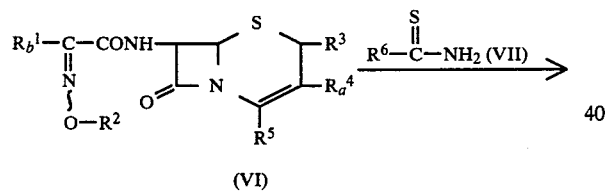
(VI)
Process H: 3-Cephem formation
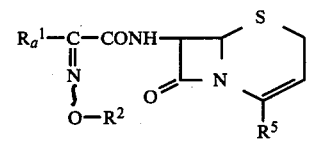
(Ig)
(Id)
Process E: Elimination of amino-protective group
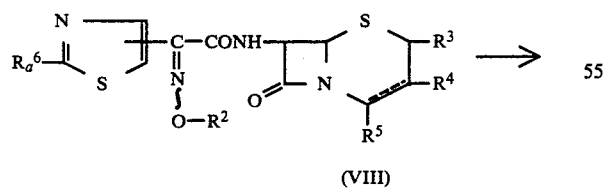
(VIII)
(Ih)
Process I: Halogenation
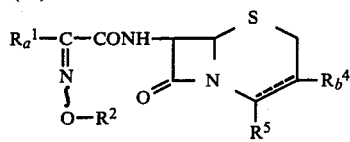
(XI)
(Ii)
(Ie)
Process F: Reductive formation of 3-hydroxycepham
Process J: Esterification
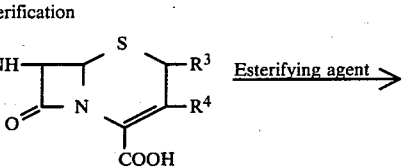
(XII)

-continued

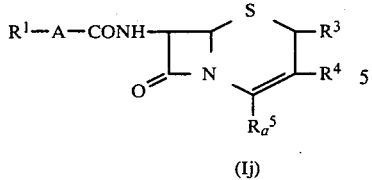

Process K: Carboxy formation

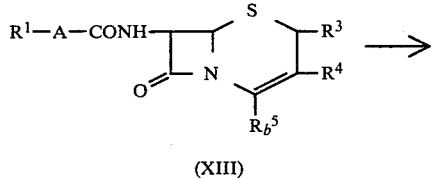

→

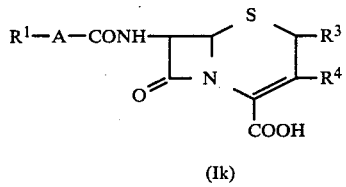

wherein
$R^2_a$ is an aliphatic hydrocarbon residue which may be substituted with halogen, carboxy or esterified carboxy,
$R^4_b$ is halogen,
$R^5_a$ is esterified carboxy,
$R^5_b$ is functionally modified carboxy,
$R^6_a$ is protected amino,
$R^7_a$ is acyl, and
$R^1$, $R^1_a$, $R^1_b$, $R^2$, $R^3$, $R^4$, $R^4_a$, $R^5$ and A are each as defined above.

The above processes will be explained in detail in the following.

Process A: N-Acylation

A compound (I) and its salt can be prepared by reacting a 7-amino-3-cephem (or cepham) compound (II), its reactive derivative at the amino or a salt thereof with a carboxylic acid (III), its reactive derivative at the carboxy or a salt thereof according to a conventional manner of so-called amidation reaction well known in β-lactam chemistry.

The starting compound (III) includes both of known and new ones, and the new compound (III) can be prepared according to the methods as explained hereinafter in this specification.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with a ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorous chloride, etc.), or with a sulfur compound (e.g. thionyl chloride, etc.), and the like.

Suitable salt of the compound (II) may be referred to the one as exemplified for the compound (I).

Suitable reactive derivative at the carboxy group of the compound (III) may include, for example, an acid halide, an acid anhydride, an activated amide, an activated ester, and the like, and preferably acid halide such as acid chloride, acid bromide; a mixed acid anhydride with an acid such as substituted phsophoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl, thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivatives of the compounds (II) and (III) can be optionally selected from the above according to the kind of the compounds (II) and (III) to be used practically, and to the reaction conditions.

Suitable salt of the compound (III) may include a salt with an inorganic base such as alkali metal salt (e.g. sodium salt, potassium salt, etc.) and an alkaline earth metal salt (e.g. calcium salt, magnesium salt, etc.), a salt with an organic base such as tertiary amine (e.g. trimethylamine salt, triethylamine salt, N,N-dimethylaniline salt, pyridine salt, etc.), a salt with an inorganic acid (e.g. hydrochloride, hydrobromide, etc.) and the like.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence to the reaction, or an optional mixture thereof.

When the acylating agent (III) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketen-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphorus oxychloride, phosgene or the like.

With regard to the geometry of the compound (I) wherein A is a group of the formula:

[hereinafter referred to as "oximino compound" (I)] produced by this process, it is to be noted that there seems to be stereoselectivity between syn and anti isomers, as expalined as follows.

In case that the reaction is conducted by reacting a compound (II) or its reactive derivative at the amino group or a salt thereof with a compound (III) wherein A is a group of the formula:

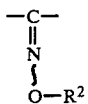

[hereinafter referred to as "oximino acylating agent" (III)] in the presence of a condensing agent, for example, phosphorus pentachloride, thionyl chloride, etc., an anti isomer of the oximino compound (I) tends to be produced as the dominant product and the corresponding syn isomer thereof can be hardly isolated from the reaction product even when a syn isomer of the oximino acylating agent (III) is used. It may be understood that the tendency of such a isomerization in the reaction conducted by the method as explained above is due to the fact that the less stable syn isomer tends to isomerize partially or wholly to the corresponding more stable anit isomer in the course of such reaction, for example, in so-called activation step of the oximino acylating agent (III) so that more stable isomer, i.e. the anti isomer of the oximino compound (I) may be isolated as the reaction product.

Accordingly, in order to obtain a syn isomer of the oximino compound (I) selectively and in high yield, it is preferable to use a syn-isomer of the oximino acylating agent (III), and to conduct the reaction under a selected reaction condition. That is, a syn isomer of the oximino compound (I) can be obtained selectively and in high yield by conducting the reaction of a compound (II) with a syn isomer of the oximino acylating agent (III), for example, in the presence of a Vilsmeier reagent as mentioned above and under around neutral condition.

The object compound (I) and salt thereof are useful as an antimicrobial agent, and a part thereof can be also used as a starting material in the following processes.

Process B: C-Nitrosation

An object compound (Ib) and its salt can be prepared by reacting a compound (IV) or its salt with a nitrosating agent.

The starting compound (IV) corresponds to the 3-cephem compound (I) wherein $R^1$ is haloacetyl, $R^4$ is hydrogen, halogen, lower alkyl or a group of the formula: $-O-R^7$ in which $R^7$ is lower alkyl and A is methylene, and can be prepared by the above Process A, preferably by reacting a compound (II) with diketene and halogen (e.g. chlorine, bromine, etc.). Thus prepared starting compound (IV) can be used in this process without any isolation and/or purification.

Suitable nitrosating agent may include nitrous acid and its conventional derivatives such as nitrosyl halide (e.g. nitrosyl chloride, nitrosyl bromide, etc.), alkali metal nitrite (e.g. sodium nitrite, potassium nitrite, etc.), alkyl nitrite (e.g. butyl nitrite, pentyl nitrite, etc.) and the like.

In case that a salt of nitrous acid is used as a nitrosating agent, the reaction is preferably carried out in the presence of an acid such as an inorganic or organic acid (e.g. hydrochloric acid, sulfuric acid, formic acid, acetic acid, etc.). And also, in case that an ester of nitrous acid is used, the reaction is preferably carried out in the presence of a strong base such as alkali metal alkoxide or the like.

This reaction is usually conducted in a solvent such as water, acetic acid, benzene, methanol, ethanol, tetrahydrofuran or any other solvent which does not adversely influence the reaction. The reaction temperature is not critical and the reaction is preferably conducted within the range of cooling to an ambient temperature.

Thus prepared compound (Ib) and salt thereof can be used as a starting material in the following Processes C and D.

Process C: Etherification

An object compound (Ic) and its salt can be prepared by reacting a compound (V) or its salt with an etherifying agent.

The starting compound (V) corresponds to the compound (I) wherein A is N-hydroxyiminomethylene group, and can be prepared by the above Process A and B and also by the following Process D.

Suitable examples of the etherifying agent may include a conventional alkylating agent such as dialkyl sulfate (e.g. dimethyl sulfate, diethyl sulfate, etc.), diazoalkane (e.g. diazomethane, diazoethane, etc.), alkyl halide (e.g. methyl iodide, ethyl iodide, ethyl bromide, etc.), alkyl sulfonate (e.g. methyl tosylate, etc.), the corresponding alkenylating-, alkynylating- or cycloalkylating agent, in which the aliphatic hydrocarbon moiety may be substituted with halogen, carboxy or esterified carboxy, for example, alkenyl halide (e.g. allyl iodide, etc.), alkynyl halide (e.g. propargyl bromide, etc.), cycloalkyl halide (e.g. cyclohexyl bromide, etc.), lower alkoxycarbonylalkyl halide (e.g. ethoxycarbonylmethyl iodide, etc.) and the like.

In case of using diazoalkane as an etherifying agent, the reaction is usually conducted in a solvent such as diethyl ether, dioxane or any other solvent which does not adversely influence the reaction, at a temperature within a range of cooling to an ambient temperature.

In case of using the other etherifying agent, the reaction is usually conducted in a solvent such as water, acetone, ethanol, diethyl ether, dimethylformamide or any other solvent which does not adversely influence the reaction within a temperature range of cooling to heating, preferably in the presence of a base such as an inorganic or organic base, suitable examples of which are referred to the ones used for the basic hydrolysis in the Process E as illustrated below.

Some of the object compound (Ic) and salt thereof are useful as an antimicrobial agent, and some of them, especially the compound where $R^1$ is haloacetyl can be used as a starting material in the following Process D.

This process is an alternative one for preparing the compound (Ic) where $R^1$ is haloacetyl group, and further this process is particularly preferable and advantageous for preparing the compound (Ic) where $R^1$ is haloacetyl and $R_a^2$ is substituted- or unsubstituted-lower alkyl, lower alkenyl or lower alkynyl, more preferably lower alkyl.

Process D: Thiazole ring formation

A compound (Id) and its salt can be prepared by reacting a compound (VI) or its salt with a thiourea compound (VII).

The starting compound (VI) corresponds to the 3-cephem compound (I) wherein $R^1$ is haloacetyl, $R^4$ is hydrogen, halogen, lower alkyl or a group of the formula: —O—$R^7$ in which $R^7$ is lower alkyl and A is a group of the formula:

in which $R^2$ is as defined above, and can be prepared by the above Process(es) A, B and/or C.

The reaction is usually conducted in a solvent such as water, alcohol (e.g. methanol, ethanol, etc.), benzene, dimethylformamide, tetrahydrofuran or any other solvent which does not adversely influence the reaction within a temperature range of an ambient temperature to heating.

This process is an alternative and highly advantageous one for providing the active compound (Id), especially (a) the compound (Id) wherein $R^2$ is hydrogen and $R^6$ is amino from the compound (IV) via the Process B, and (b) the compound (Id) wherein $R^2$ is lower alkyl and $R^6$ is amino from the compound (IV) via the Processes B and C.

Process E: Elimination of amino-protective group

A compound (Ie) and its salt can be prepared by subjecting a compound (VIII) or its salt to elimination reaction of the protective group in the protected amino group for $R_a^6$.

The starting compound (VIII) corresponds to the compound (I) wherein $R^1$ is thiazolyl of the formula:

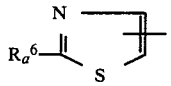

in which $R_a^6$ is protected amino and A is a group of the formula:

in which $R^2$ is as defined above, and can be prepared, for example, by the above Process A.

The elimination reaction may be conducted in accordance with a conventional method such as hydrolysis, reduction or the like. These methods may be selected according to the kind of the protective group to be eliminated.

The hydrolysis may include a method using an acid (acidic hydrolysis), a base (basic hydrolysis) or hydrazine, and the like.

Among these methods, hydrolysis using an acid is one of the common and preferable methods for eliminating the protective group such as an acyl group, for example, substituted or unsubstituted lower alkanoyl, substituted or unsubstituted lower alkoxycarbonyl, substituted or unsubstituted ar(lower)alkoxycarbonyl, lower cycloalkoxycarbonyl, substituted phenylthio, substituted alkylidene, substituted aralkylidene, substituted cycloalkylidene or the like, particulars of which are to be referred to those as illustrated for the N-protective group, respectively.

Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can be easily separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the protective group to be eliminated. The acidic hydrolysis can be conducted in the presence or absence of a solvent. Suitable solvent may be a conventional organic solvent, water or a mixture thereof, which does not adversely influence this reaction. Particularly, when the hydrolysis is conducted with trifluoroacetic acid, the reaction may be accelerated by addition of anisole.

The hydrolysis using a base can be applied for eliminating the protective group such as an acyl group, preferably, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2,]octane, 1,5-diazabicyclo[5,4,0]-7-undeceneanion-exchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl, for example, halo(lower)alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, etc.), 2-pyridylmethoxycarbonyl, etc., aralkyl (e.g. benzyl, benzhydryl, trityl, etc.) and the like. Suitable reduction may include, for example, reduction using an alkali metal borohydride (e.g. sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

The reaction temperature is not critical and may be optionally selected in consideration of the chemical property of the starting compound and reaction product as well as the kind of the N-protective group and the method to be applied, and the reaction is preferably carried out under a mild condition such as under cooling, at ambient temperature or slightly elevated temperature.

The process includes in its scope the cases that the functionally modified carboxy for $R^5$ is simultaneously transformed into the free carboxy group in the course of the above reaction or in the post-treatment.

As to this process, it is to be understood that the purpose of this process lies in providing the generally more active compound (I') wherein $R_a{}^1$ is aminothiazolyl by eliminating the protective group in the protected amino group of the compound (VIII) prepared by the other processes as mentioned above or below.

Process F: Reductive formation of 3-hydroxycepham

A compound (If) and its salt can be prepared by reducing a compound (IX) or its salt.

The starting compound (IX) corresponds to the 3-cephem compound (I) wherein $R^1$ is thiadiazolyl or thiazolyl of the formula:

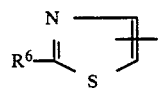

in which $R^6$ is as defined above, $R^3$ is hydrogen, $R^4$ is a group of the formula: $-O-R^7$ in which $R^7$ is hydrogen and A is a group of the formula:

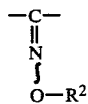

in which $R^2$ is as defined above, and can be prepared, for example, by the above Process A.

The method of reduction applied to this process may include a conventional one which is applicable for reduction of ketonic carbonyl group including its tautomeric enol form into hydroxymethylene group, and the preferable method may be reduction using an alkali metal borohydride (e.g. sodium borohydride, etc.) or a combination of an acid (e.g. hydrochloric acid, sulfuric acid, formic acid, acetic acid, etc.) and a metal (e.g. zinc, iron, copper, etc.), catalytic reduction using a conventional catalyst (e.g. palladium on carbon, palladium sponge, Raney nickel, platinum, platinum black, etc.) or the like.

The reaction is usually carried out in a conventional solvent such as water, alcohol (e.g. methanol, ethanol, etc.), dimethylformamide, tetrahydrofuran or any other solvent which does not adversely influence the reaction within a temperature range from cooling to somewhat elevated temperature.

Although thus prepared compound (If) and salt thereof have antimicrobial activities, they are also useful mainly as an intermediate, especially as a starting material in the following Process G and successively Process H for preparing the more active 3-cephem compound (Ih).

Process G: O-acylation

A compound (Ig) and its salt can be prepared by reacting a compound (If) or its salt with a compound (X), its salt or its reactive derivative.

As to the compound (X), suitable examples of the acyl moiety for $R_a{}^7$ are to be referred to those as exemplified above for the acyl group for $R^7$ of the compound (I).

The reactive derivative of the compound (X) may be an acyl halide, anhydride, azide, activated ester, activated amide and the like, which are to be referred to those as exemplified above for the compound (III) in the Process A, preferably an acyl halide such as lower alkanoyl halide (e.g. acetyl chloride, etc.), aroyl halide (e.g. benzoyl chloride, etc.), lower alkanesulfonyl halide (e.g. mesyl chloride, mesyl bromide, ethanesulfonyl chloride, etc.), arenesulfonyl halide (e.g. tosyl chloride, etc.), an acyl azide such as lower alkanesulfonyl azide (e.g. mesyl azide, etc.), arenesulfonyl azide (e.g. tosyl azide, etc.) or the like, and more preferably lower alkanesulfonyl halide or arenesulfonyl halide.

The reaction is usually carried out in a conventional solvent such as dimethylformamide, chloroform, methylene chloride or any other solvent which does not adversely influence the reaction, under cooling or at an ambient or somewhat elevated temperature.

In case that the acyl halide is used as an acylating agent, the reaction is generally conducted in the presence of a base as exemplified in the above Process E.

This process is the first activation step for preparing a more active 3-cephem compound (Ih) from the 3-hydroxycephem compound (If) via the 3-acyloxycepham compound (Ig), which is successively treated with a base in the following Process H.

Process H: 3-Cephem formation

This process is the final step to transform the 3-hydroxycephem compound (IX) into the more active 3-cephem compound (Ih) or its salt. That is, a compound (Ih) or its salt can be prepared by treating a compound (Ig) as prepared in the above Process G or its salt with a base.

The preferable base includes an inorganic base such as metal hydroxide (e.g. sodium hydroxide, potassium hydroxide, etc.), metal carbonate (e.g. sodium carbonate, potassium carbonate, magnesium carbonate, etc.), metal bicarbonate (e.g. sodium bicarbonate, potassium bicarbonate, etc.), organic base such as tertiary amine (e.g. trimethyl amine, triethyl amine, pyridine, etc.) alkali metal alkoxide (e.g. sodium methoxide, sodium ethoxide, etc.) and the like.

The reaction is usually carried out in a conventional solvent such as an alcohol, dimethylformamide, chloroform, methylene chloride or any other solvent which does not adversely influence the reaction, under cooling or at an ambient or somewhat elevated temperature.

Process I: Halogenation

A compound (Ii) or its salt can be prepared by halogenating a compound (XI) or its salt.

The starting compound (XI) corresponds to the compound (I) wherein $R^1$ is thiadiazolyl or thiazolyl of the formula:

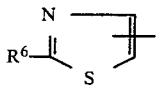

in which R⁶ is as defined above, R³ is hydrogen, R⁴ is a group of the formula: —O—R⁷ in which R⁷ is hydrogen and A is a group of the formula:

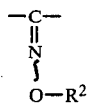

in which R² is as defined above, and can be prepared by the processes as explained above.

Suitable halogenating agent may include a conventional halogen compound such as phosphorus halide (e.g. phosphorus trichloride, phosphorus pentachloride, phosphorus tribromide, phosphorus pentabromide, phosphoryl chloride, etc.), thionyl chloride and the like.

The reaction is usually carried out in a conventional solvent such as chloroform, methylene chloride, dimethylformamide or any other solvent which does not adversely influence the reaction and preferably under cooling or at ambient or somewhat elevated temperature.

Process J: Esterification

This process is to provide an ester compound (Ij) and its salt for improving the chemical, phisiological and/or pharmaceutical properties of the corresponding free carboxy compound (XII), which corresponds to the 3-cephem compound (I) wherein R⁵ is carboxy, or its salt.

The esterification is conducted by reacting a free carboxy compound (XII), its reactive derivative at the carboxy or a salt thereof with an esterifying agent.

The preferred reactive derivative at the carboxy group of the compound (XII) is to be referred to those of the compound (III) as exemplified in the Process A.

The esterifying agent may include a hydroxy compound and its reaction equivalent.

Suitable examples of the hydroxy compound may be a substituted or unsubstituted alcohol such as alkanol, aralkanol, arenol or the like, particulars of which may be substituted alcohol such as alkanoyloxy(lower)alkanol (e.g. acetoxymethanol, propionyloxymethanol, butyryloxymethanol, pentanoyloxymethanol, hexanoyloxymethanol, acetoxyethanol, propionyloxyethanol, butyryloxyethanol, pentanoyloxyethanol, hexanoyloxyethanol, acetoxypropanol, propionyloxypropanol, hexanoyloxypropanol, hexanoyloxyhexanol, palmitoyloxymethanol, etc.), halo(lower)alkanol (e.g. mono-, di- or trichloroethanol, etc.), lower cycloalkyl(lower)alkanol (e.g. 1-cyclopropylethanol, etc)., substituted ar(lower)alkanol (e.g. 4-nitrobenzyl alcohol, 4-chlorobenzyl alcohol, 4-methoxybenzyl alcohol, 3,5-di-tert-butyl-4-hydroxybenzyl alcohol, bis(methoxyphenyl)methanol, etc.), substituted arenol (e.g. 4-methoxyphenol, etc.), the corresponding unsubstituted alcohol or the like.

Suitable reactive equivalent of the hydroxy compound may include a conventional one such as halide, alkanesulfonate, arenesulfonate or salt of the hydroxy compound, diazoalkane, diazoaralkane, and the like.

Preferable halide of the hydroxy compound may be chloride, bromide or iodide.

Preferable alkane- or arene-sulfonate of the hydroxy compound may be methanesulfonate, ethanesulfonate, benzenesulfonate, tosylate or the like.

Preferable salt of the hydroxy compound may be an alkali metal salt such as lithium salt, sodium salt, potassium salt or the like.

Preferable diazoalkane and diazoaralkane may be diazomethane, diazoethane, diazopropane, diphenyldiazomethane or the like.

The reaction can be carried out in the presence or absence of a solvent such as N,N-dimethylformamide, dimethylsulfoxide or any other solvent which does not adversely influence the reaction, and within a temperature range of cooling to heating. The liquid hydroxy compound can be also used as a solvent in this reaction.

This reaction can be preferably conducted in the presence of an inorganic or organic base as exemplified in the above Process E.

In case of preparing a substituted- or unsubstituted-aryl ester (Ij), particularly substituted-or unsubstituted-phenyl ester, this reaction is to be conducted by reacting (a) a compound (XII) or its salt with phenol or its salt in the presence of a condensing agent as exemplified in the above Process A, or (b) a reactive derivative of the compound (XII) preferably a mixed acid anhydride of the compound (XII) with phenol or its salt in the presence of a base.

In case that a compound (XII), where A is a group of the formula:

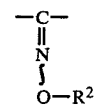

in which R² is an aliphatic hydrocarbon residue substituted with carboxy, is used as a starting material in this reaction, the said carboxy group may be also esterified in accordance with the reagent and the reaction conditions, and this mode of the reaction is included within the scope of this process.

And further, in case that the 2-cephem compound corresponding to the compound (Ij) is produced, the said 2-cephem compound can be transformed into the 3-cephem compound (Ij) by oxydizing and then reducing the resultant S-oxide compound in a conventional manner. This mode of the reactions is also included within the scope of this process.

Process K: Carboxy formation

This process is to provide a free carboxy compound (Ik) or its salt, expecially the compound (Ik) wherein R¹ is thiadiazolyl or thiazolyl of the formula:

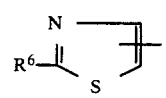

in which R⁶ is as defined above and A is a group of the formula:

in which R² is as defined above, which generally exhibits higher antimicrobial activities as compared with the corresponding functionally modified carboxy compound (XIII).

Accordingly, the meaning of the functionally modified carboxy in the compound (XIII) lies in mainly synthetic manufacture by chemical process(es) as illustrated hereinabove.

This process is conducted by transforming the functionally modified carboxy group of the starting compound (XIII) into free carboxy group, and the preferred functionally modified carboxy for $R^5_b$ in the compound (XIII) may be an esterified carboxy group as exemplified for $R^5$ of the compound (I).

The method to be applied to this process includes conventional ones such as hydrolysis, reduction and the like.

The method of hydrolysis includes a conventional one using an acid, base, enzyme or enzymatic preparation, and the like.

Suitable examples of the acid and base are to be referred to those as exemplified in the above Process E, and the acidic or basic hydrolysis can be carried out in a similar manner to that of the Process E.

Suitable enzyme includes an esterase and esterase preparation which exhibits an esterase activity such as a cultured broth of microorganism or processed materials of microorganism, the preparation of animal or plant tissues, or the like, and preferably a cultured broth of microorganism or processed material thereof.

An esterase to be used in the enzymatic hydrolysis may be used not only in a purified state, but also in a crude state.

Such an esterase is frequently found to exist widely, for example, in various kind of microorganisms, which can be easily isolated from a soil sample and other sources by conventional means, and further can be easily selected from the collected cultures available in public facilities for culture collection such as ATCC (American Type Culture Collection, Maryland, USA), IAM (Institute of Applied Microbiology, University of Tokyo, Japan), IFO (Institute For Fermentation, Osaka, Japan), IID (The Institute for Infectious Diseases, University of Tokyo, Tokyo, Japan), CBS (Centraalbureau voor Schimmelcultures, Bearn, Netherlands), FERM (Fermentation Research Institute, Agency of Industrial Science and Technology, Chiba, Japan) and NRRL (Northern Utilization Research and Development Division, U.S. Department of Agriculture, Illinois, U.S.A.) and the like.

As to the microorganism having an esterase activity, there may be exemplified one belonging to the genus, Bacillus, Corynebacterium, Micrococcus, Flavovacterium, Salmonella, Staphylococcus, Vibrio, Microbacterium, Escherichia, Arthrobacter, Azotobacter, Alcaligenes, Rhizobium, Brevibacterium, Kluyvera, Proteus, Sarcina, Pseudomonas, Xanthomonas, Protaminobacter, Comamonus and the like.

Examples of the above microorganisms may be *Bacillus subtilis* IAM-1069, IAM-1107, IAM-1214, *Bacillus sphaericus* IAM-1286, *Corynebacterium equi* IAM-1308, *Micrococcus varians* IAM-1314, *Flavobacterium rigeus* IAM-1238, *Salmonella typhimurium* IAM-1406, *Staphylococcus epidermidis* IAM-1296, *Microbacterium flavum* IAM-1642, *Alcaligenes faecalis* ATCC-8750, *Arthrobacter simplex* ATCC-6946, *Azotobacter vinelandii* IAM-1078, *Escherichia coli* IAM-1101, *Rhizobium japonicum* IAM-0001, *Vibrio metchnikovii* IAM-1039, *Brevibacterium helvolum* IAM-1637, *Protaminobacter alboflavum* IAM-1040, *Comamonas terrigena* IFO-12685, *Sarcina lutea* IAM-1099, *Pseudomonus schuylkilliensis* IAM-1055, *Xanthomonas trifolii* ATCC-12287 or the like.

In the enzymatic hydrolysis, the esterase can be preferably used in a form of a cultured broth obtained by culturing microorganisms having an esterase activity in a suitable manner, or of its processed material.

Cultivation of microorganisms can be generally conducted in a conventional manner. As a culture medium to be used, there may be used a nutrient one containing sources of assimilable carbon and nitrogen and inorganic salts. The preferred sources of carbon are, for example, glucose, sucrose, lactose, sugars, glycerol and starch. The preferred sources of nitrogen are, for example, meat extract, peptone, gluten meal, corn meal, cotton-seed meal, soybean meal, corn steep liquor, yeast extracts, casein hydrolysate and amino acids, as well as inorganic and organic nitrogen such as ammonium salts (e.g. ammonium sulfate, ammonium nitrate, ammonium phosphate, etc.), sodium nitrate or the like. If desired, mineral salts such as calcium carbonate, sodium or potassium phosphate, magnesium salts and copper salts, and various vitamines can be also used.

Suitable pH of the culture medium, suitable cultivation temperature and suitable cultivation time vary with the kind of the microorganisms to be used. A desirable pH usually lies in a range of pH 5 to 8. The temperature is usually selected from about 20° C. to about 35° C. The cultivation time is usually selected from 20 hours to 120 hours.

The cultured broth per se thus obtained and its processed material may be employed for enzymatic hydrolysis of this process. The "processed material" of cultured broth means any preparation having esterase activity, which is processed by conventionally suitable means for increasing said esterase activity.

The esterase activity of the cultured broth is present in cells (intracellularly) and/or out of cells (extracellularly).

When the activity exists mainly in cells, the following preparation, for example, may be used as a processed material of the cultured broth.

(1) raw cells; separated from the cultured broth in conventional manners such as filtration and centrifugation, (2) dried cells; obtained by drying said raw cells in conventional manners such as lyophilization and vacuum drying, (3) a cell-free extract; obtained by destroying said raw or dried cells in conventional manners (e.g. grinding the cells with almina, sea sand, etc. or treating the cells with super sonic waves), or (4) an enzyme solution; obtained by purification or partial purification of said cell-free extract in a conventional manner.

When the activity exists mainly out of cells, the following preparation, for example, may be used as a processed material.

(1) a supernatant or a filtrate; obtained from the cultured broth in a conventional manner, or (2) an enzyme solution; obtained by purification or partial purification of said supernatant or filtrate in a conventional manner.

The enzymatic hydrolysis is conducted by contacting the compound (XIII) with the cultured broth of the microorganism or its processed material in an aqueous medium such as water or a buffer solution (e.g. phosphate buffer, etc.), preferably in the presence of conventional surface-active agent. That is, the reaction is usually conducted by adding the compound (XIII) to the cultured broth of the microorganism or its liquid processed material (e.g. supernatant, filtrate, enzyme solution, etc.), or to the solution or suspension of the cultured broth or its processed material in an aqueous medium. Sometimes, an agitation of the said reaction mixture is preferable.

Preferred pH of reaction mixture, concentration of substrates, reaction time and reaction temperature may vary with characteristics of the cultured broth or its processed material to be used, or the compound (XIII) to be used. However, the reaction conditions are preferably selected from a range of at pH 4 to 10, more preferably at pH 6 to 8, at 20° to 50° C., more preferably at 25° to 35° C. for 1 to 100 hours. The concentration of the starting compound (XIII) to be used as a substrate in the reaction mixture may be in a range of 0.1 to 100 mg per ml, preferably 1 to 20 mg per ml.

The method of the reduction for this process may be carried out in a similar manner to that of the above Process E.

This process includes within its scope the cases that the protective group in the protected amino for $R^6$, which is a substituent on the thiazolyl group for $R^1$, is eliminated and/or the esterified carboxy group, which is an optional substituent on the aliphatic hydrocarbon residue for $R^2$ in the group A, is transformed into free carboxy group in the course of the reaction or the post-treatment.

The compound obtained in accordance with the processes as explained above can be isolated and purified in a conventional manner.

In case that the object compound (I) has free carboxy for $R^5$ and/or free amino for $R^6$, it may be transformed into its pharmaceutically acceptable salt by a conventional method.

Among the object compound (I), the compound (I'), its pharmaceutically acceptable salt and bioprecursor thereof exhibit high antimicrobial activities inhibiting the growth of a wide variety of pathogenic microorganisms including Gram-positive and Gram-negative bacteria and are useful as antimicrobial agents.

And further, the compound (I") and its salt are novel and useful as an intermediate for preparing the active compound (I'), its pharmaceutically acceptable salt or bioprecursor thereof.

According to the aforementioned processes, more specifically the following compounds can be prepared.

7-[2-(2-amino-4-thiazolyl)-2-methoxyiminoacetamido]-3-methoxy-3-cephem-4-carboxylic acid (syn isomer)

7-[2-(2-amino-4-thiazolyl)-2-methoxyiminoacetamido]-2,3-dimethyl-3-cephem-4-carboxylic acid (syn isomer)

7-[2-(2-amino-4-thiazolyl)-2-methoxyiminoacetamido]-3-chloro-3-cephem-4-carboxylic acid (anti isomer)

7-[2-(1,2,3-thiadiazol-4-yl)-2-methoxyiminoacetamido]-3-cephem-4-carboxylic acid (syn isomer)

7-[2-(2-amino-4-thiazolyl)-2-hydroxyiminoacetamido]-3-cephem-4-carboxylic acid (syn isomer)

7-[2-(2amino-4-thiazolyl)-2-methoxyiminoacetamido]-3-tosyloxy-3-cephem-4-carboxylic acid (syn isomer)

7-[2-(2-amino-4-thiazolyl)-2-ethoxyiminoacetamido]-3-cephem-4-carboxylic acid (syn isomer)

7-[2-(2-amino-4-thiazolyl)-2-ethoxyiminoacetamido]-3-chloro-3-cephem-4-carboxylic acid (syn isomer)

7-[2-(2-amino-4-thiazolyl)-2-isopropoxyiminoacetamido]-3-cephem-4-carboxylic acid (syn isomer)

7-[2-(2-amino-4-thiazolyl)-2-propoxyiminoacetamido]-3-chloro-3cephem-4-carboxylic acid (syn isomer)

7-[2-(2-amino4-thiazolyl)-2-propoxyiminoacetamido]-3cephem-4-carboxylic acid (syn isomer)

7-[2-(2-amino-4-thiazolyl)-2-isobutyloxyiminoacetamido]-3-cephem-4-carboxylic acid (syn isomer)

7-[2-(2-amino-4-thiazolyl)-2-n-butoxyiminoacetamido]-3-cephem-4-carboxylic acid (syn isomer)

7-[2-(2-amino-4-thiazolyl)-2-n-hexyloxyiminoacetamido]-3-cephem-4-carboxylic acid (syn isomer)

7-[2-(2-amino-4-thiazolyl)-2cyclohexyloxyiminoacetamido]-3-cephem-4-carboxylic acid (syn isomer)

7-[2-(2-amino-4-thiazolyl)-2-allyloxyiminoacetamido]-3-cephem-4-carboxylic acid (syn isomer)

7-[2-(2-amino-4-thiazolyl)-2-propargyloxyiminoacetamido]-3-cephem-4-carboxylic acid (syn isomer)

7-[2-(2-amino-4-thiazolyl)-2-ethoxycarbonylmethoxyiminoacetamido]-3-cephem-4-carboxylic acid (syn isomer)

7-[2-(2-amino-4-thiazolyl)-2-carboxymethoxyiminoacetamido]-3-cephem-4-carboxylic acid (syn isomer)

7-[2-(2-amino-4-thiazolyl)-2-n-pentyloxyiminoacetamido]-3-cephem-4-carboxylic acid (syn isomer)

7-[2-(2-amino-4-thiazolyl)-2-(2,2,2-trifluoroethoxyimino)acetamido]-3-cephem-4-carboxylic acid (syn isomer)

7-[2-(2-amino-4-thiazolyl)-2-(2-chloroethoxyimino)acetamido]-3-cephem-4-carboxylic acid (syn isomer)

7-[2-(2-amino-4-thiazolyl)-2-(2,2,2-trifluoroethoxyimino)acetamido]-3-chloro-3-cephem-4-carboxylic acid (syn isomer)

7-[2-(2-formamido-4-thiazolyl)-2-methoxyiminoacetamido]-3-cephem-4-carboxylic acid (syn isomer)

7-[2-(2-amino-4-thiazolyl)-2-methoxyiminoacetamido]-3-cephem-4-carboxylic acid (anti isomer)

7-[2-(2-amino-4-thiazolyl)-2-n-octyloxyiminoacetamido]-3-cephem-4-carboxylic acid (syn isomer)

7-[2-(2-amino-4thiazolyl)-2-(2,3,3-trifluoro-2-propenyloxyimino)acetamido]-3-cephem-4-carboxylic acid (syn isomer)

7-[2-(2-amino-4-thiazolyl)-2-lauroyloxymethoxyiminoacetamido]-3-cephem-4-carboxylic acid (syn isomer)

7-[2-(1,2,3-thiadiazol-4-yl)-2-n-hexyloxyiminoacetamido]-3-cephem-4-carboxylic acid (syn isomer)

7-[2-(2-amino-4-thiazolyl)-2-n-butoxyiminoacetamido]-3-chloro-3-cephem-4-carboxylic acid (syn isomer)

7-[2-(2-amino-4-thiazolyl)-2-n-butoxyiminoacetamido]-3-methoxy-3-cephem-4-carboxylic acid (syn isomer)

7-[2-(2-amino-4-thiazolyl)-2-propargylox-
yiminoacetamido]-3-methoxy-3-cephem-4-carboxylic
acid (syn isomer)
7-[2-(2-amino-4-thiazolyl)-2-trifluoromethox-
yiminoacetamido]-3-cephem-4-carboxylic acid (syn
isomer)
the corresponding functionally modified derivative
such as
hexanoyloxymethyl 7-[-2-(2-amino-4-thiazolyl)-2-
methoxyiminoacetamido]-3-cephem-4-carboxylate
(syn isomer)
pivaloyloxymethyl 7-[2-(2-amino-4-thiazolyl)-2-
methoxyiminoacetamido]-3-cephem-4-carboxylate
(syn isomer)
4-nitrobenzyl 7-[2-(2-amino-4-thiazolyl)-2-methox-
yiminoacetamido]-3-cephem-4-carboxylate (syn iso-
mer)
4-nitrobenzyl 7-[2-(2-amino-4-thiazolyl)-2-methox-
yiminoacetamido]-3-hydroxy-3-cephem-4-carboxy-
late (syn isomer)
4-nitrobenzyl 7-[2-(2-amino-4-thiazolyl)-2-ethox-
yiminoacetamido]-3-hydroxy-3-cephem-4-carboxy-
late (syn isomer)
4-nitrobenzyl 7-[2-(2-amino-4-thiazolyl)-2-n-propox-
yiminoacetamido]-3-hydroxy-3-cephem-4-carboxy-
late (syn isomer)
4-nitrobenzyl 7-[2-(2-amino-4-thiazolyl)-2-isobutox-
yiminoacetamido]-3-hydroxy-3-cephem-4-carboxy-
late (syn isomer)
the corresponding salt such as
sodium 7-[2-(2-amino-4-thiazolyl)-2-methox-
yiminoacetamido]-3-cephem-4-carboxylate (syn iso-
mer)
calcium 7-[2-(2-amino-4-thiazolyl)-2-methox-
yiminoacetamido]-3-cephem-4-carboxylate (syn iso-
mer)
magnesium 7-[2-(2-amino-4-thiazolyl)-2-methox-
yiminoacetamido]-3-cephem-4-carboxylate (syn iso-
mer)
arginine salt of 7-[2-(2-amino-4-thiazolyl)-2-methox-
yiminoacetamido]-3-cephem-4-carboxylic acid (syn
isomer)
lysine salt of 7-[2-(2-amino-4-thiazolyl)-2-methox-
yiminoacetamido]-3-cephem-4-carboxylic acid (syn
isomer)
7-[2-(2-amino-4-thiazolyl)-2-methoxyiminoacetamido]-
3-cephem-4-carboxylic acid hydrochloride (syn iso-
mer)

In order to show the utility of the active compound (I'), the test data of some representative compounds (I') are shown in the following.

1. In vitro antibacterial activity:
   (1) Test method:
   In vitro antibacterial activity was determined by the two-fold agar-plate dilution method as described below.
   One loopful of the 100-fold dilution of an overnight culture of each test strain in Trypticase-soy broth was streaked on heart infusion agar (HI-agar) containing graded concentrations of the test compound and incubated at 37° C. for 20 hours. The minimal inhibitory concentration (MIC) was expressed in μg/ml.

| | |
|---|---|
| 1 | 7-[2-(2-Amino-4-thiazolyl)-2-methoxyiminoacetamido]-3-cephem-4-carboxylic acid (syn isomer) |
| 2 | 7-[2-(2-Amino-4-thiazolyl)-2-hydroxyiminoacetamido]-3-cephem-4-carboxylic acid (syn isomer) |
| 3 | 7-[2-(2-Amino-4-thiazolyl)-2-ethoxyiminoacetamido]-3-cephem-4-carboxylic acid (syn isomer) |
| 4 | 7-[2-(2-Amino-4-thiazolyl)-2-methoxyiminoacetamido]-3-chloro-3-cephem-4-carboxylic acid (syn isomer) |
| 5 | 7-[2-(Amino-4-thiazolyl)-2-n-propoxyiminoacetamido]-3-cephem-4-carboxylic acid (syn isomer) |
| 6 | 7-[2-(2-Amino-4-thiazolyl)-2-n-butoxyiminoacetamido]-3-cephem-4-carboxylic acid (syn isomer) |
| 7 | 7-[2-(2-Amino-4-thiazolyl)-2-allyloxyiminoacetamido]-3-cephem-4-carboxylic acid (syn isomer) |
| 8 | 7-[2-2-Amino-4-thiazolyl)-2-propargyloxyiminoacetamido]-3-cephem-4-carboxylic acid (syn isomer) |
| 9 | 7-[2-(2-Amino-4-thiazolyl)-2-n-pentyloxyiminoacetamido]-3-cephem-4-carboxylic acid (syn isomer) |
| 10 | 7-[2-(Amino-4-thiazolyl)-2-n-hexyloxyiminoacetamido]-3-cephem-4-carboxylic acid (syn isomer) |
| 11 | 7-[-2-(Amino-4-thiazolyl)-2-cyclohexyloxyiminoacetamido]-3-cephem-4-carboylic acid (syn isomer) |
| 12 | 7-[2-(2-Amino-4-thiazolyl)-2-(2-chloroethoxyimino)-acetamido]-3-cephem-4-carboxylic acid (syn isomer) |
| 13 | 7-[2-(2-Amino-4-thiazolyl)-2-(2,2,2-trifluoroethoxyimino)acetamido]-3-cephem-4-carboxylic acid (syn isomer) |

(3) Test results MIC (μg/ml)

| Test Strains | Compound No. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Staphylococcus aureus 209P JC-1 | 6.25 | 0.39 | 3.13 | 12.5 | 1.56 | 0.78 | 1.56 | 1.56 | 0.39 | 1.56 | 0.39 | 1.56 | 1.56 |
| Escherichia coli. NIHJ JC-2 | ≦0.025 | 0.1 | 0.05 | 0.39 | 0.2 | 0.39 | 0.2 | 0.1 | 3.13 | 1.56 | 3.13 | 0.1 | 0.2 |
| Proteus vulgaris IAM-1025 | ≦0.025 | 0.1 | ≦0.025 | ≦0.025 | ≦0.025 | 0.05 | ≦0.025 | ≦0.025 | 0.39 | 0.2 | 0.78 | ≦0.025 | ≦0.025 |
| Klebsiella pneumoniae 20 | ≦0.025 | ≦0.025 | ≦0.025 | 0.1 | ≦0.025 | 0.2 | ≦0.025 | ≦0.025 | 0.2 | 0.05 | 0.39 | 0.1 | 0.05 |
| Proteus mirabilis 18 | ≦0.025 | ≦0.025 | ≦0.025 | 0.0125 | 0.1 | 0.2 | ≦0.025 | ≦0.025 | 1.56 | 0.78 | 1.56 | 0.2 | 0.2 |
| Pseudomonus aeruginosa NCTC-10490 | 0.39 | 6.25 | ≦1.56 | 6.25 | ≦1.56 | ≦1.56 | ≦1.56 | ≦1.56 | 3.13 | ≦1.56 | ≦1.56 | ≦1.56 | ≦1.56 |
| Serratia marcescens 35 | 1.56 | 12.5 | 0.78 | 50 | 3.13 | 6.25 | 1.56 | 3.13 | 3.13 | 12.5 | 12.5 | 12.5 | 6.25 |

2. Protecting effect against experimental infections in mice:

(1) Test method
Male ICR strain mice aged 4 weeks, each weighing 18.5–21.5 g. were used in groups in 10 mice. The test bacteria were cultured overnight at 37° C. on Trypticase-soy agar and then suspended in 5% mucin to obtain the suspension corresponding to each challenge cells. Mice were inoculated intraperitoneally with 0.5 ml. of the suspension. A solution containing each test compound was given subcutaneously to the mice in various dosage one hour after the challenge. The $ED_{50}$ values were calculated from the number of surviving mice for each dosage after four days of observation.

(2) Test compounds

| No. | |
|---|---|
| 1 | 7-[2-(2-Amino-4-thiazolyl)-2-methoxyiminoacetamido]-3-cephem-4-carboxylic acid (syn isomer) |
| reference | 7-[2-(2-Amino-4-thiazolyl)-2-methoxyimino-acetamido] cephalospolanic acid (syn isomer) |

(3) Test results:

| Test Bacteria | Inoculated Cells/mouse | $ED_{50}$(s.c.)(mg/kg) | | MIC ($\mu$g/ml.) | | |
|---|---|---|---|---|---|---|
| | | Test Compounds | | Inoculum Size | Test Compounds | |
| | | 1 | reference | | 1 | reference |
| Escherichia coli 54 | $1.1 \times 10^7$ | 0.95 | 2.8 | $10^0$ *1 | 0.78 | 3.13 |
| | | | | $10^{-2}$ *2 | 0.05 | 0.1 |
| Klebsiella pneumoniae 39 | $8 \times 10^6$ | <0.98 | 0.995 | $10^0$ | 0.39 | 3.13 |
| | | | | $10^{-2}$ | $\leq$0.025 | 0.05 |
| Proteus rettgeri 24 | $9.9 \times 10^6$ | 0.39 | 1.171 | $10^0$ | 1.56 | 50 |
| | | | | $10^{-2}$ | $\leq$0.025 | 0.1 |
| Serratia Marcescens 58 | $1.2 \times 10^7$ | 3.562*3 | 31.427*3 | $10^0$ | 25 | 50 |
| | | | | $10^{-2}$ | 0.39 | 1.56 |

*1 overnight culture
*2 100-fold dilution of the overnight culture
*3 treated with two divisional doses at 1 hr. and 3 hrs. after infection 3. Acute toxicity:
(1) Test method:
Ten male and 10 female rats aged 6 weeks (JCL-SD strain) were used per group. Test compound dissolved in distilled water was given subcutaneously and intraveneously to the animals. These animals were observed for 7 days after dosing. The $LD_{50}$ values were calculated from the number of dead animals by the Litchfield-Wilcoxon method.

(2) Test compound:
7-[2-(2-amino-4-thiazolyl)-2-methoxyiminoacetamido]-3-cephem-4-carboxylic acid (syn isomer)
(3) Test results:

| Test animal | Sex | $LD_{50}$ (mg./kg.) | |
|---|---|---|---|
| | | s.c. | i.v. |
| Rat | Male | >8000 | about 8000 |
| | Female | >8000 | >8000 |

4. Absorbability
(1) Test method:
Test compound was given orally to a group of 5 rats (JCL-SC strain, 6-week-old, male) which had been fasted. Bile and urine samples were collected at 0~6 and 6~24 hrs. The concentrations of the test compound in the samples were determined by bioassay (disk method) using Batillus subtilis ATCC-6633 as test organism, and the recoveries in bile and urine were calculated.

(2) Test compound:
7-[2-(2-amino-4-thiazolyl)-2-n-pentyloxyiminoacetamido]-3-cephem-4-carboxylic acid (syn isomer)

(3) Test result:
Total recovery in bile and urine in 24 hrs. was 22.8%.

For prophylactic and/or therapeutic administration, the active compound (I') of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age and conditions of the patient, a kind of disease and a degree of the infection, and further a kind of the active compound (I') to be applied, etc., an average single dose of about 50 mg., 100 mg., 250 mg. and 500 mg. of the active compound (I') is sufficient for treating infectious diseases caused by pathogenic bacteria. In general, the active compound (I') can be administered in an amount betweeen 1 mg/kg and 100 mg/kg, preferably 5 mg/kg and 50 mg/kg.

The starting compound (III) can be prepared as illustrated below.

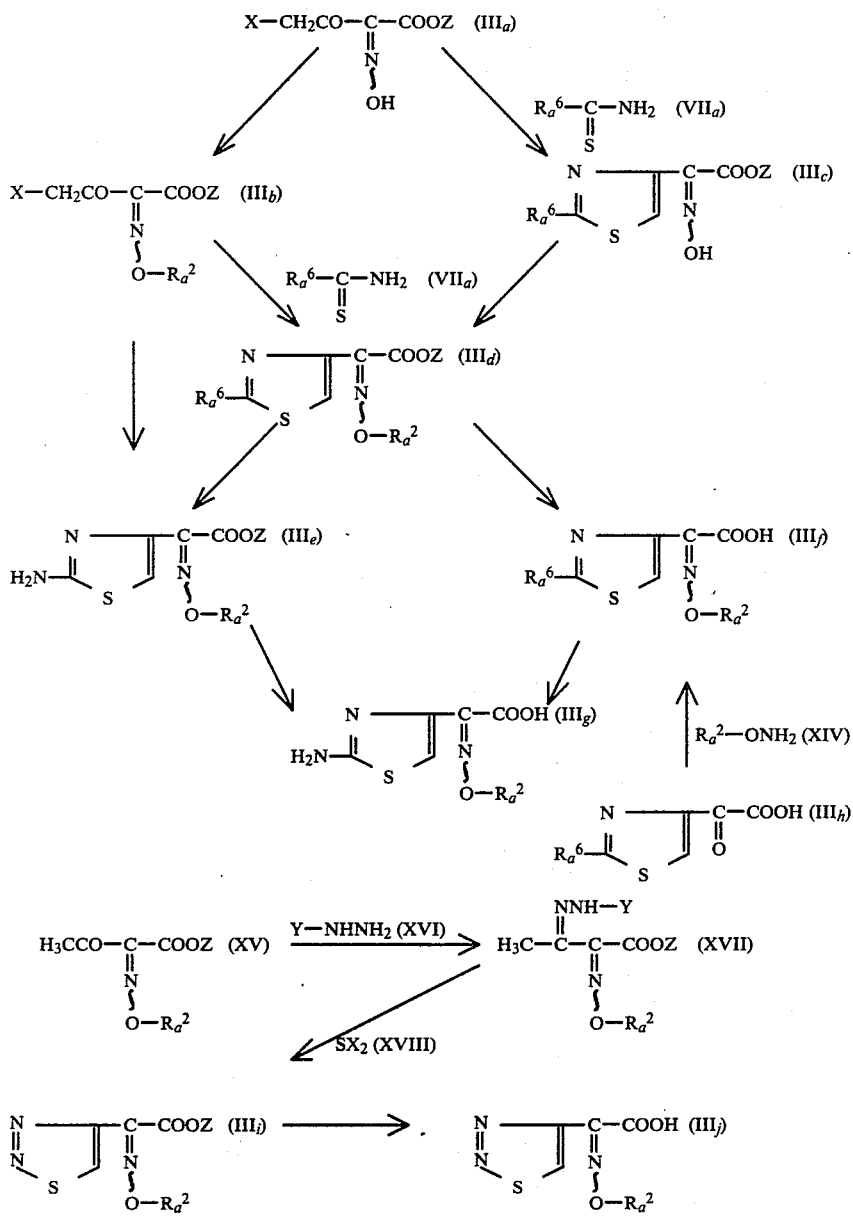

wherein $R_a^2$ is an aliphatic hydrocarbon residue which may be substituted with halogen, carboxy or estrified carboxy $R_a^6$ is protected amino X is halogen Y is lower alkoxycarbonyl, and Z is lower alkyl Each of the above processes are explained in the following.

Process 1: Etherification

The compound (III$_b$) and (III$_d$) can be prepared by reacting a compound (III$_a$) or (III$_c$) with an etherifying agent, respectively.

This reaction may be conducted substantially in the same manner as the aforementioned Process C.

Process 2: Thiazole ring formation

The compound (III$_c$) and (III$_d$) can be prepared by reacting a compound (III$_a$) or (III$_b$) with a thiourea compound (VII$_a$), respectively, and further the compound (III$_e$) can be prepared by reacting a compound (III$_b$) with thiourea.

This reaction may be conducted substantially in the same manner as the aforementioned Process D.

Process 3: Elimination of amino-protective group

The compound (III$_e$) and (III$_g$) can be prepared by subjecting a compound (III$_d$) or (III$_f$) to elimination reaction of the protective group in the protected amino group for $R_a^6$, respectively.

This reaction may be conducted substantially in the same manner as the aforementioned Process E.

Process 4: Carboxy formation

The compound (III$_f$), (III$_g$) and (III$_j$) can be prepared by transforming the esterified carboxy group of a compound (III$_d$), (III$_e$) or (III$_i$) into free carboxy group, respectively.

This reaction may be conducted substantially in the same manner as the aforementioned Process K.

Process 5: Oximation

The compound (I$_f$) can be also prepared by reacting a compound (III$_h$) with a hydroxylamine derivative (XIV) or its salt.

The hydroxylamine derivative (XIV) may be hydroxylamine substituted with an aliphatic hydrocarbon residue which may be substituted with halogen, carboxy or esterified carboxy, particulars of which are to be referred to those as exemplified before. Suitable salt of the hydroxylamine derivative (XIV) may be hydrochloride, hydrobromide, sulfate or the like.

The reaction is usually conducted in a conventional solvent such as water, alcohol, tetrahydrofuran, acetonitrile, dimethylsulfoxide, pyridine or any other solvent which does not adversely influence the reaction, or a mixture thereof, and the reaction temperature is not critical.

In case that a salt of the hydroxylamine derivative (XIV) is used as a reagent, the reaction is preferably conducted in the presence of a conventional base.

Process 6: Thiadiazol ring formation

The compound (III$_i$) can be prepared by reacting a compound (XV) with a hydrazine derivative (XVI), and then reacting the resultant compound (XVII) with sulfur dihalide (XVIII).

Among the starting compound (III), the compound of the formula:

wherein
R$_a^1$ is thiadiazolyl or thiazolyl of the formula:

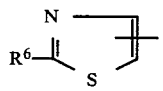

in which R$^6$ is amino or protected amino,

R$_a^{2'}$ is alkyl, alkenyl or alkynyl having more the one carbon atom or cycloalkyl which may be substituted with halogen, carboxy or esterified carboxy, R$^8$ is hydrogen or lower alkyl, provided that R$^6$ is amino which may be protected with formyl, and R$^8$ is hydrogen, when R$_a^{2'}$ is ethyl, isopropyl or allyl, is novel and useful as a starting material in the aforementioned Process A.

Particulars of each definition in the above are to be referred to those as explained before.

Following examples are given only for explaining this invention in more detail.

Preparation of the starting compounds:

EXAMPLE A (1) A solution of ethyl 2-methoxyiminoacetoacetate (a mixture of syn and anti isomers) (34.6 g.) and t-butoxycarbonylhydrazine (26.4 g.) in ethanol (200 ml.) was stirred for 7.5 hours at ambient temperature and allowed to stand overnight to precipitate crystals. The crystals were collected by filtration, washed with ethanol and dried to give ethyl 2-methoxyimino-3-t-butoxycarbonylhydrazonobutyrate (a mixture of syn and anti isomers) (41.7 g.), mp 144° to 145° C.

I.R. $\nu_{max}^{Nujol}$: 3200, 1750, 1705, 1600, 1520 cm$^{-1}$.

N.M.R. $\delta_{ppm}$ (CDCl$_3$): 8.52 (1H, broad s), 4.35 (2H, q, J=7 Hz), 4.10 (3H, s), 2.00 (3H, s), 1.50 (9H, s), 1.33 (3H, t, J=7 Hz).

(2) Sulfur dichloride (15.9 ml.) was added with stirring at ambient temperature to a solution of ethyl 2-methoxyimino-3-t-butoxycarbonylhydrazonobutyrate (a mixture of syn and anti isomers) (14.35 g.) in methylene chloride (150 ml.), and the mixture was stirred for 1 hour at ambient temperature. To the reaction mixture was added ice-water (300 ml.), and the methylene chloride layer was washed with water, with a saturated aqueous solution of sodium bicarbonate and with a saturated aqueous solution of sodium chloride and dried over magnesium sulfate. The solvent was distilled off to give an oil. The oil was purified by column chromatography on silica gel using a mixture of benzene and n-hexene (19:1) as an eluent to firstly give ethyl 2-methoxyimino-2-(1,2,3-thiadiazol-4-yl)acetate (syn isomer) (1.8 g.), mp 77° to 79° C.

I.R. $\nu_{max}^{Nujol}$: 1720, 1595 cm$^{-1}$.

N.M.R. $\delta_{ppm}$ (CDCl$_3$): 8.92 (1H, s), 4.46 (2H, q, J=7 Hz), 4.06 (3H, s), 1.38 (3H, t, J=7 Hz).

From subsequent fractions, ethyl 2-methoxyimino-2-(1,2,3-thiadiazol-4-yl)acetate (anti isomer) (0.7 g.) was obtained as an oil.

I.R. $\nu_{max}^{Film}$: 1730, 1590 cm$^{-1}$.

N.M.R. $\delta_{ppm}$ (CDCl$_3$): 9.38 (1H, s), 4.47 (2H, q, J=7 Hz), 4.20 (3H, s), 1.40 (3H, t, J=7 Hz).

(3) 1N Aqueous solution of sodium hydroxide (6.7 ml.) was added to a solution of ethyl 2-methoxyimino-2-(1,2,3-thiadiazol-4-yl)acetate (syn isomer) (1.2 g.) in methanol (10 ml.) and the mixture was stirred for 1.5 hours at ambient temperature. Methanol was distilled off from the reaction mixture and water was added to the residue. The mixture was washed with ether, adjusted to pH 1 with 10% hydrochloric acid and extracted with ethyl acetate. The extract was washed with a saturated aqueous solution of sodium chloride and dried over magnesium sulfate. The solvent was distilled off to give prisms of 2-methoxyimino-2-(1,2,3-thiadiazol-4-yl)acetic acid (syn isomer) (0.7 g.), m.p. 110° to 113° C.

I.R. $\nu_{max}^{Nujol}$: 2750-2150, 1730, 1595 cm$^{-1}$.

N.M.R. $\delta_{ppm}$ (d$_6$-DMSO): 9.47 (1H, s), 4.01 (3H, s)

EXAMPLE B (1) Pulverized potassium carbonate (160 g.) was added to a solution of ethyl 2-hydroxyiminoacetoacetate (a mixture of syn and anti isomers) (152 g.) in acetone (500 ml.). Dimethyl sulfate (130 g.) was dropwise added thereto with stirring over 1 hour at 45° to 50° C. and the mixture was stirred for 2 hours. An insoluble material was filtered off and the filtrate was concentrated under reduced pressure. The filtered insoluble material was dissolved in water (500 ml.) and this solution was added to the residue. The mixture was extracted twice with ethyl acetate (300 ml.). The extract was washed twice with water (200 ml.) and with a saturated sodium chloride aqueous solution (200 ml.) and dried over magnesium sulfate. The solvent was distilled off under reduced pressure and the residue was distilled under reduced pressure to give colorless oil of ethyl 2-methoxyiminoacetoacetate (a mixture of syn and anti isomers) (145.3 g.), bp (55° to 64° C./0.5 mm Hg.

I.R. $\nu_{max}^{Film}$: 1745, 1695, 1600 cm$^{-1}$.

N.M.R. $\delta_{ppm}$ (CDCl$_3$): 4.33 (4H, q, J=8 Hz), 4.08 (3H, s), 3.95 (3H, s), 2.40 (3H, s), 1.63 (3H, s), 1.33 (6H, t, J=8 Hz).

(2) Sulfuryl chloride (235 ml.) was dropwise added over 20 minutes with stirring and ice-cooling to a solution of ethyl 2-methoxyiminoacetoacetate (syn isomer) (500 g.) in acetic acid (500 ml.), and the mixture was stirred overnight under cooling with water. Nitrogen gas was introduced to the reaction mixture for 2 hours, and the resulting mixture was poured into water (2.5 l.) After extracting with methylene chloride (500 ml.) and twice with methylene chloride (200 ml.), the extracts were combined. The combined extract were washed with a saturated aqueous solution of sodium chloride, and adjusted to pH 6.5 by adding water (800 ml.) and sodium bicarbonate. Methylene chloride layer was separated, washed with an aqueous solution of sodium chloride and dried over magnesium sulfate. The solvent was distilled off to give ethyl 2-methoxyimino-4-chloroacetoacetate (syn isomer) (559 g.).

I.R. $\nu_{max}^{Film}$: 1735, 1705 cm$^{-1}$.

(3) Ethyl 2-methoxyimino-4-chloroacetoacetate (syn isomer) (50 g.) was added over 3 minutes with stirring at ambient temperature to a solution of thiourea (18.4 g.) and sodium acetate (19.8 g.) in a mixture of methanol (250 ml.) and water (250 ml.). After stirring for 35 minutes at 40° to 45° C., the reaction mixture was cooled with ice and adjusted to pH 6.3 with a saturated aqueous solution of sodium bicarbonate. After stirring for 30 minutes at the same temperature, precipitates were collected by filtration, washed with water (200 ml.) and then with diisopropyl ether (100 ml.), and dried to give colorless crystals of ethyl 2-methoxyimino-2-(2-amino-1,3-thiazol-4-yl)acetate (syn isomer) (37.8 g.), m.p. 161° to 162° C.

I.R. $\nu_{max}^{Nujol}$: 3400, 3300, 3150, 1725, 1630, 1559 cm$^{-1}$.

N.M.R. $\delta_{ppm}$ (CDCl$_3$): 6.72 (1H, s), 5.91 (2H, broad s), 4.38 (2H, q, J=7 Hz), 4.03 (3H, s), 1.38 (3H, t, J=7 Hz).

(4) Ethanol (10 ml.) was added to a suspension of ethyl 2-methoxyimino-2-(2-amino-1,3-thiazol-4-yl)acetate (syn isomer) (2.2 g.) in a 1 N aqueous solution of sodium hydroxide (12 ml.) and the mixture was stirred for 15 hours at ambient temperature. The reaction mixture was adjusted to pH 7.0 with 10% hydrochloric acid and ethanol was distilled off under reduced pressure. The residual aqueous solution was washed with ethyl acetate, adjusted to pH 2.8 with 10% hydrochloric acid and stirred under ice-cooling to precipitate crystals. The crystals were collected by filtration, washed with acetone and recrystallized from ethanol to give colorless needles of 2-methoxyimino-2-(2-amino-1,3-thiazol-4-yl)acetic acid (syn isomer) (1.1 g.)

I.R. $\nu_{max}^{Nujol}$: 3150, 1670, 1610, 1585 cm$^{-1}$.

N.M.R. $\delta_{ppm}$ (d$_6$-DMSO): 7.20 (2H, broad s), 6.85 (1H, s), 3.83 (3H, s).

EXAMPLE C (1) Sulfuryl chloride (35.2 g.) was added all at once to the stirred solution of ethyl 2-ethoxyimino-3-oxobutyrate (syn isomer, 48.9 g.) in acetic acid (49 ml.) at room temperature, and stirred at the same temperature for an hour. After adding the resultant solution into water (200 ml.), the solution was extracted with methylene chloride. The extract was washed with a saturated aqueous solution of sodium chloride, neutralized with an aqueous solution of sodium bicarbonate and washed with water. The solution was dried over magnesium sulfate and concentrated under reduced pressure to give ethyl 2-ethoxyimino-3-oxo-4-chlorobutyrate (syn isomer, 53.8 g.), pale yellow oil.

(2) A mixture of ethyl 2-ethoxyimino-3-oxo-4-chlorobutyrate (syn isomer 38.7 g.), thiourea (13.2 g.), sodium acetate (14.3 g.), methanol (95 ml.) and water (95 ml.) was stirred at 48° C. for 40 minutes. After the resultant solution was adjusted to pH 6.5 with an aqueous solution of sodium bicarbonate, the appeared precipitates were collected by filtration and washed with diisopropyl ether to give ethyl 2-(2-amino-4-thiazolyl)-2-ethoxyiminoacetate (syn isomer, 14.7 g.), mp 130° to 131° C.

I.R. $\nu_{max}^{Nujol}$: 3450, 3275, 3125, 1715, 1620 cm$^{-1}$.

(3) Ethyl 2-(2-amino-4-thiazolyl)-2-ethoxyiminoacetate (syn isomer, 5 g.) was added to a mixture of 1 N sodium hydroxide (45.9 ml.) and ethanol (30 ml.) and stirred at room temperature for 5 hours. After removing ethanol from the resultant solution under reduced pressure, the residue was dissolved in water (60 ml.) and adjusted to pH 2.0 with 10% hydrochloric acid. The solution was subjected to salting-out, and the precipitates were collected by filtration and dried to give 2-(2-amino-4-thiazolyl)-2-ethoxyiminoacetic acid (syn isomer, 2.9 g.).

I.R. $\nu_{max}^{Nujol}$: 3625, 3225 (shoulder), 3100, 1650, 1615 cm$^{-1}$.

N.M.R. $\delta$ppm (DMSO-d$_6$): 1.20 (3H, t, J=7 Hz), 4.09 (2H, q, J=7 Hz), 6.82 (1H, s), 7.24 (2H, broad s).

(4) 2-(2-Aminothiazol-4-yl)-2-ethoxyiminoacetic acid (syn isomer, 100 g.), formic acid (85.5 g.) and acetic anhydride (190.1 g.) were treated in a similar manner to that of Example F-(5) to give 2-(2-formamidothiazol-4-yl)-2-ethoxyiminoacetic acid (syn isomer, 99.1 g.).

I.R. $\nu_{max}^{Nujol}$: 3200, 3140, 3050, 1700 cm$^{-1}$.

N.M.R. $\delta$(DMSO-d$_6$, ppm): 1.18 (3H, t, J=6 Hz), 4.22 (2H, q, J=6 Hz), 7.56 (1H, s), 8.56 (1H, s), 12.62 (1H, broad s).

EXAMPLE D (1) To a suspension of ethyl 2-hydroxyimino-3-oxobutyrate (syn isomer, 15 g.) and potassium carbonate (19.8 g.) in acetone (75 ml.) was added dropwise propyliodide (16.2 g.) with stirring, and the mixture was stirred at ambient temperature for 1,5 hours. The insoluble substance was collected by filtration and washed with acetone. The washings and the filtrate were combined and evaporated to dryness under reduced pressure. To the resultant residue was added water and the aqueous solution was extracted twice with chloroform. The extract was washed with an aqueous solution of sodium chloride, dried over magnesium sulfate, and then evaporated to dryness under reduced pressure to give ethyl 3-oxo-2-propoxyiminobutyrate (syn isomer, 15.4 g.), oil.

(2) Ethyl 3-oxo-2-propoxyiminobutyrate (syn isomer, 15.4 g.) and sulfuryl chloride (10.6 g.) were dissolved in acetic acid (15.4 ml.), warmed at 35° to 45° C. for 10 minutes with stirring and then stirred at ambient temperature for additional 6 hours. The reaction mixture was poured into ice-water (200 ml.) and the resultant mixture was extracted twice with chloroform. The extract was washed with an aqueous solution of sodium chloride, twice a saturated aqueous solution of sodium bicarbonate and once with water in turn, dried over magnesium sulfate, and then evaporated to dryness under reduced pressure to give ethyl 4-chloro-3-oxo-2-propoxyiminobutyrate (syn isomer, 15.4 g.), oil.

I.R. $\nu_{max}^{film}$: 1740, 1710, 1695, 1455 cm$^{-1}$.

(3) Ethyl 4-chloro-3-oxo-2-propoxyiminobutyrate (syn isomer, 15.4 g.), thiourea (4.97 g.) and sodium acetate hydrate (8.89 g.) were dissolved in a mixture of water (40 ml.) and ethanol (50 ml.), and stirred at 40° C. for an hour.

The reaction mixture was adjusted to pH 6.5 with a saturated aqueous solution of potassium carbonate under cooling and stirred at the same temperature for half an hour. The precipitating crystals were collected by filtration, washed with water and diisopropyl ether, and then dried to give crystalline ethyl 2-(2-amino-4-thiazolyl)-2-propoxyiminoacetate (syn isomer, 10.55 g.), mp 142°–144° C.

I.R. $\nu_{max}^{Nujol}$: 3460, 3260, 3120, 1720, 1620, 1540 cm$^{-1}$.

N.M.R. δppm (d$_6$-DMSO): 0.88 (3H, t, J=7 Hz), 1.27 (3H, t, J=6 Hz), 1.60 (2H, sextet, J=7 Hz), 4.04 (2H, t, J=7 Hz), 4.28 (2H, q, J=6 Hz), 6.86 (1H, s), 7.23 (2H, s).

(4) A solution of ethyl 2-(2-amino-4-thiazolyl)-2-propoxyiminoacetate (syn isomer, 10 g.) in a mixture of tetrahydrofuran (39 ml.), methanol (39 ml.) and 1 N sodium hydroxide (75.8 ml.) was stirred at 35° to 40° C. for 5 hours.

After the resultant solution was concentrated under reduced pressure, the aqueous residue was adjusted to pH 2.5 with 10% hydrochloric acid. The precipitates were collected by filtration and dried to give 2-(2-amino-4-thiazolyl)-2-propoxyiminoacetic acid (synisomer, 6.2 g.), mp 161° C. (dec.)

I.R. $\nu_{max}^{Nujol}$: 3380, 3120 (broad), 1630, 1610, 1460 cm$^{-1}$.

N.M.R. δppm (DMSO-d$_6$): 0.89 (3H, t, J=7 Hz), 1.63 (2H, sextet, J=7 Hz), 4.05 (2H, t, J=7 Hz), 6.83 (1H, s), 6.9–8.8 (3H, broad).

(5) 2-(2-Aminothiazol-4-yl)-2-n-propoxyiminoacetic acid (syn isomer, 21.8 g.), acetic anhydride (38.8 g.) and formic acid (17.5 g.) were treated in a similar manner to that of Example F-(5), and then the obtained oil was triturated with diisopropyl ether to give 2-(2-formamidothiazol-4-yl)-2-n-propoxyiminoacetic acid (syn isomer, 19.2 g.), mp. 164° C. (dec.).

I.R. $\nu_{max}^{Nujol}$: 3200, 3120, 3050, 1700, 1550 cm$^{-1}$.

N.M.R. δ(DMSO-d$_6$, ppm): 0.92 (3H, t, J=7 Hz), 1.67 (2H, sextet, J=7 Hz), 4.12 (2H, t, J=7 Hz), 7.53 (1H, s), 8.54 (1H, s).

EXAMPLE E (1) Ethyl 2-hydroxyimino-3-oxobutyrate (syn isomer, 30 g.), iso-propyl iodode (32.5 g.), potassium carbonate (39.5 g.) and acetone (150 ml.) were treated in a similar manner to that of Example D-(1) to give ethyl 2-iso-propoxyimino-3-oxobutyrate (syn isomer, 35.4 g.), oil.

I.R. $\nu_{max}^{Film}$: 1745, 1690, 1600 cm$^{-1}$.

N.M.R. δ(CCl$_4$, ppm): 1.33 (3H, t, J=7 Hz), 1.35 (6H, d, J=6 Hz), 2.32 (3H, s), 4.1~4.7 (3H, m).

(2) Ethyl 2-iso-propoxyimino-3-oxobutyrate (syn isomer 35.4 g.), sulfuryl chloride (24.5 g.) and acetic acid (35.4 ml.) were treated in a similar manner to that of Example D-(2) to give ethyl 4-chloro-3-oxo-2-iso-propoxyiminobutyrate (syn isomer, 41.5 g.), oil.

I.R. $\nu_{max}^{Film}$: 1745, 1715, 1375 cm$^{-1}$.

(3) Ethyl 4-chloro-3-oxo-2-iso-propoxyiminobutyrate (syn isomer, 41.5 g.), thiourea (13.4 g.), sodium acetate (14.4 g.), water (110 ml.) and ethanol (110 ml.) were treated in a similar manner to that of Example D-(3) to give ethyl 2-(2-aminothiazol-4-yl)-2-iso-propoxyiminoacetate (syn isomer, 27.3 g.), mp. 162° to 164° C.

I.R. $\nu_{max}^{Nujol}$: 3460, 3430, 3260, 3150, 1725, 1615 1540 cm$^{-1}$.

N.M.R. δ(DMSO-d$_6$, ppm): 1.17 (6H, d, J=6 Hz), 1.24 (3H, t, J=7 Hz), 4~4.7 (3H, m), 6.86 (1H, s), 7.24 (2H, s).

(4) Ethyl 2-(2-aminothiazol-4-yl)-2-iso-propoxyiminoacetate (syn isomer, 26.8 g.), 1N aqueous solution of sodium hydroxide (156 ml.), methanol (156 ml.) and tetrahydrofuran (100 ml.) were treated in a similar manner to that of Example D-(4) to give 2-(2-aminothiazol-4-yl)-2-iso-propoxyiminoacetic acid (syn isomer, 15.3 g.), mp. 151° C. (dec.).

I.R. $\nu_{max}^{Nujol}$: 3610, 3580, 3080, 1650, 1610 cm$^{-1}$.

N.M.R. δ(DMSO-d$_6$, ppm): 1.22 (6H, d, J=6Hz), 4.33 (1H, quintet, J=6Hz), 6.80 (1H, s), 7.22 (2H, broad s).

(5) 2-(2-Aminothiazol-4-yl)-2-iso-propoxyiminoacetic acid (syn isomer, 4 g.), acetic anhyddride (7.6 g.) and formic acid (3.4 g.) were treated in a similar manner to that of Example F-(5) to give 2-(2-formamidothiazol-4-yl)-2-iso-propoxyiminoacetic acid (syn isomer, 3.75 g.), mp. 168° to 169° C. (dec.).

I.R. $\nu_{max}^{Nujol}$: 3200, 3130, 1710, 1600, 1560 cm$^{-1}$.

N.M.R. δ(DMSO-d$_6$, ppm): 1.26 (6H, d), 4.4 (1H, m), 7.54 (1H, s), 8.52 (1H, s), 12.56 (1H, broad s).

EXAMPLE F (1) n-Butyl iodide (46.9 g.) was added dropwise to a stirred suspension of ethyl 2-hydroxyimino-3-oxobutyrate (syn isomer, 40 g.), potassium carbonate (52.7 g.) and acetone (200 ml.) under ice-cooling over 5 minutes, and stirred at room temperature for 4 hours. The resultant solution was filtered, and washed with acetone. The filtrate and washing solution were combined together and concentrated in vacuo. After adding water (300 ml.) to the residue, the solution was extracted with methylene chloride three times. The solution was washed with a saturated aqueous solution of sodium chloride, dried over magnesium sulfate and concentrated in vacuo to give ethyl 2-n-butoxyimino-3-oxobutyrate (syn isomer, 48.8 g.), oil.

I.R. $\nu_{max}^{Film}$: 1750, 1700, 1470, 1370, 1320 cm$^{-1}$.

(2) A solution of ethyl 2-n-butoxyimino-3-oxobutyrate (syn isomer, 48.8 g.), sulfuryl chloride (31.5 g.) and acetic acid (48.8 ml.) was stirred at 40° C. for 10 minutes and further at room temperature for 5.5 hours. After water (300 ml.) was added to the resultant solution under ice cooling, the solution was extracted with methylene chloride three times. The extract was washed with water, an aqueous solution of sodium bicarbonate and a saturated aqueous solution of sodium chloride in turn, and dried over magnesium sulfate. The solution was concentrated in vacuo to give ethyl 2-n-butoxyimino-4-chloro-3-oxobutyrate (syn isomer, 52.1 g.), oil.

I.R. $\nu_{max}^{Film}$: 1740, 1710, 1470, 1370 cm$^{-1}$.

(3) A solution of ethyl 2-n-butoxyimino-4-chloro-3-oxobutyrate (syn isomer, 52.1 g.) thiourea (15.9 g.), sodium acetate 3 hydrate (28.4 g.), water (130 ml.) and ethanol (180 ml.) was stirred at 40° C. for 1.25 hours. The resultant solution was adjusted to pH 6.5 with an aqueous solution of sodium carbonate under ice cooling, and stirred for 20 minutes under ice cooling. The precipitates were collected by filtration, and washed with water and diisopropyl ether in turn to give ethyl 2-(2-aminothiazol-4-yl)-2-n-butoxyiminoacetate (syn isomer, 36.1 g.), mp 126° to 128° C.

I.R. $\nu_{max}^{Nujol}$: 3460, 3370, 3230, 1720, 1620, 1550 cm$^{-1}$.

N.M.R. δ(DMSO-d$_6$, ppm): 0.6–2.0 (6H, m), 1.28 (3H, t, J=7Hz), 4.12 (3H, t, J=6Hz), 4.31 (2H, q, J=7Hz), 6.89 (1H, s), 7.24 (2H, s).

(4) A solution of ethyl 2-(2-aminothiazol-4-yl)-2-nbutoxyiminoacetate (syn isomer, 36 g.), methanol (133 ml.), tetrahydrofuran (133 ml.) and 2 N aqueous solution of sodium hydroxide (133 ml.) was stirred at 30° C. for 5 hours. After the resultant solution was concentrated in vacuo, the residue was dissolved in water. The solution was adjusted to pH 7 with 10% hydrochloric acid and treated with activated charcoal. The solution was adjusted to pH 2.0 with 10% hydrochloric acid and stirred for 20 minutes under ice cooling. The precipitates were collected by filtration, washed with water and acetone in turn, and dried to give 2-(2-aminothiazol-4-yl)-2-n-butoxyiminoacetic acid (syn isomer, 25.4 g.).

I.R. $\nu_{max}^{Nujol}$: 3325, 3190, 1660, 1620 cm$^{-1}$.

N.M.R. δ(DMSO-d$_6$, ppm): 0.88 (3H, t, J=7Hz), 1.0–1.9 (4H, m), 4.06 (2H, t, J=7Hz), 6.81 (1H, s), 7.21 (2H, broad s).

(5) Formic acid (18.95 g.) was added dropwise to acetic anhydride (42.0 g.) under stirring at room temperature over 5 minutes, and stirred at 50° C. for an hour. 2-(2-Aminothiazol-4-yl)-2-n-butoxyiminoacetic acid (syn isomer, 25 g.) was added to the solution under ice cooling, and stirred at room temperature for 3 hours and additionally at 30° C. for an hour. After concentrating the resultant solution in vacuo, the residue was dissolved in diethyl ether. The solution was washed with water and a saturated aqueous solution of sodium chloride in turn, dried over magnesium sulfate and concentrated in vacuo. The obtained oil was triturated with a solution of n-hexane (1 part) and diisopropyl ether (1 part), and collected by filtration to give 2-(2-formamidothiazol-4-yl)-2-n-butoxyiminoacetic acid (syn isomer, 20.1 g.).

I.R. $\nu_{max}^{Nujol}$: 3350, 3160, 3050, 1700, 1680, 1570 cm$^{-1}$.

N.M.R. δ(DMSO-d$_6$, ppm): 0.91 (3H, t, J=6Hz), 1.0–2.2 (4H, m), 4.18 (2H, t, J=6Hz), 7.57 (1H, s), 8.59 (1H, s), 12.66 (1H, broad s).

EXAMPLE G (1) Ethyl 2-hydroxyimino-3-oxobutyrate (syn isomer, 40 g.), N,N-dimethylformamide (200 ml.), potassium carbonate (52.7 g.) and iso-butyl bromide (34.94 g.) were treated in a similar manner to that of Example F-(1) to give ethyl 2-iso-butoxyimino-3-oxo-butyrate (syn isomer, 42 g.).

I.R. $\nu_{max}^{Nujol}$: 1740, 1670 (broad) cm$^{-1}$.

(2) Ethyl 2-iso-biutoxyimino-3-oxobutyrate (syn isomer, 42 g.), acetic acid (42 ml.) and sulfuryl chloride (27.1 g.) were treated in a similar manner to that of Example F-(2) to give ethyl 2-iso-butoxyimino-4-chloro-3-oxobutyrate (syn isomer, 31.9 g.).

I.R. $\nu_{max}^{film}$: 1750, 1720, 1680 cm$^{-1}$.

(3) Ethyl 2-iso-butoxyimino-4-chloro-3-oxobutyrate (syn isomer, 31.9 g.), thiourea (9.72 g.), sodium acetate 3-hydrate (17.4 g.), ethanol (120 ml.) and water (80 ml.) were treated in a similar manner to that of Example F-(3) to give ethyl 2-(2-aminothiazol-4-yl)-2-iso-butoxyiminoacetate (syn isomer, 17.6 g.), mp 122° to 124° C.

I.R. $\nu_{max}^{Nujol}$: 3470, 3260, 3120, 1730, 1620, 1545 cm$^{-1}$.

N.M.R. δ(DMSO-d$_6$, ppm): 0.86 (6H, d, J=7Hz), 1.28 (3H, t, J=7Hz), 1.6–2.2 (1H, m), 3.86 (2H, d, J=7Hz), 4.28 (2H, q, J=7Hz), 6.86 (1H, s), 7.22 (2H, s).

(4) Ethyl 2-(2-aminothiazol-4-yl)-2-iso-butoxyiminoacetate (syn isomer, 19.6 g.), 2 N aqueous solution of sodium hydroxide (72.2 ml.), methanol (72.2 ml.) and tetrahydrofuran (72.2 ml.) were treated in a similar manner to that of Example F-(4) to give 2-(2-aminothiazol-4-yl)-2-iso-butoxyiminoacetic acid (syn isomer, 16.1 g.), mp 180° C. (dec.).

I.R. $\nu_{max}^{Nujol}$: 3375, 3300, 3130, 3050, 1640 cm$^{-1}$.

N.M.R. δ(DMSO-d$_6$, ppm): 0.91 (6H, d, J=7Hz), 1.5–2.3 (1H, m), 3.90 (2H, d, J=7Hz), 6.87 (1H, s), 7.26 (2H, broad s).

(5) 2-(2-Aminothiazol-4-yl)-2-iso-butoxyiminoacetic acid (syn isomer, 11.5 g.), acetic anhydride (19.3 g.) and formic acid (8.7 g.) were treated in a similar manner to that of Example F-(5) to give 2-(2-formamidothiazol-4-yl)-2-iso-butoxyiminoacetic acid (syn isomer, 11.15 g.), mp 163° C. (dec.).

I.R. $\nu_{max}^{Nujol}$: 3175, 3110, 3050, 1695, 1550 cm$^{-1}$.

N.M.R. δ(DMSO-d$_6$, ppm): 0.91 (6H, d, J=7 Hz), 1.7–2.3 (1H, m), 3.92 (2H, d, J=7 Hz), 7.52 (1H, s), 8.52 (1H, s), 12.58 (1H, broad s).

EXAMPLE H (1) Ethyl 2-hydroxyimino-3-oxobutyrate (syn isomer, 30 g.), N,N-dimethylformamide (100 ml.), potassium carbonate (39.5 g.) and cyclohexyl bromide (31.1 g.) were treated in a similar manner to that of Example F-(1) to give ethyl 2-cyclohexyloxyimino-3-oxobutyrate (syn isomer, 41.8 g.), oil.

I.R. $\nu_{max}^{Film}$: 1680 cm$^{-1}$.

(2) Ethyl 2-cyclohexyloxyimino-3-oxobutyrate (syn isomer, 41.3 g.), acetic acid (41.3 ml.) and sulfuryl chloride (23.8 g.) were treated in a similar manner to that of Example F-(2) to give ethyl 4-chloro-2-cyclohexyloxyimino-3-oxobutyrate (syn isomer, 27.8 g.), oil.

I.R. $\nu_{max}^{Film}$: 1745, 1715, 1680 cm$^{-1}$.

(3) Ethyl 4-chloro-2-cyclohexyloxyimino-3-oxobutyrate (syn isomer, 27.8 g.), thiourea (7.7 g.), sodium acetate 3-hydrate (13.7 g.), water (70 ml.) and ethanol (140 ml.) were treated in a similar manner to that of Example F-(3) to give ethyl 2-(2-aminiothiazol-4-yl)-2-cyclohexyloxyiminoacetate (syn isomer, 3.6 g.), mp. 125° to 126° C.

I.R. $\nu_{max}^{Nujol}$: 3430, 3250, 3160, 3130, 1715, 1635 cm$^{-1}$.

N.M.R. δ(DMSO-d$_6$, ppm): 1.28 (3H, t, J=7 Hz), 1.0~2.2 (10H, m), 4.22 (1H, m), 4.32 (2H, q, J=7 Hz), 6.88 (1H, s), 7.24 (2H, broad s).

(4) Ethyl 2-(2-aminothiazol-4-yl)-2-cyclohexyloxyiminoacetate (syn isomer, 3.5 g.), 2 N aqueous solution of sodium hydroxide (11.8 ml.), methanol (11.8 ml.) and tetrahydrofuran (11.8 ml.) were treated in a similar manner to that of Example F-(4) to give 2-(2-aminothiazol-4-yl)-2-cyclohexyloxyiminoacetic acid (syn isomer, 2.1 g.), mp. 148° C. (dec.).

I.R. $\nu_{max}^{Nujol}$: 3110, 1630, 1450 cm$^{-1}$.

N.M.R. δ(DMSO-d$_6$, ppm): 0.8~2.3 (10H, m), 4.14 (1H, m), 6.86 (1H, s), 7.5 (2H, broad s).

(5) 2-(2-Aminothiazol-4-yl)-2-cyclohexyloxyiminoacetic acid (syn isomer, 1.5 g.), acetic anhydride (2.27 g.) and formic acid (1.03 g.) were treated in a similar manner to that of Example F-(5), and the oil obtained was suspended in an aqueous solution of sodium bicarbonate. The suspension was adjusted to pH 3.5 with 10% hydrochloric acid. The precipitates were collected by filtration, washed with water and dried to give 2-(2-formamidothiazol-4-yl)-2-cyclohexyloxyiminoacetic acid (syn isomer, 1.0 g.), mp. above 230° C.

I.R. $\nu_{max}^{Nujol}$: 3175, 3100, 3060, 1680 cm$^{-1}$.

EXAMPLE I (1) Ethyl 2-hydroxyimino-3-oxobutyrate (syn isomer, 56.7 g.), N,N-dimethylformamide (280 ml.), potassium carbonate (72.3 g.) and propargyl bromide (43 g.) were treated in a similar manner to that of Example F-(1) to give ethyl 2-propargyloxyimino-3-oxobutyrate (syn isomer, 71.2 g.).

I.R. $\nu_{max}^{Film}$: 3280, 3220, 2120, 1735, 1670 cm$^{-1}$.

(2) Ethyl 2-propargyloxyimino-3-oxobutyrate (syn isomer, 71.2 g.), acetic acid (81 ml.) and sulfuryl chloride (50.2 g.) were treated in a similar manner to that of Example F-(2) to give ethyl 4-chloro-3-oxo-2-propargyloxyiminobutyrate (syn isomer, 61.6 g.), oil.

I.R. $\nu_{max}^{Film}$: 3300, 2130, 1745, 1720, 1675 cm$^{-1}$.

N.M.R. δ(CCl$_4$, ppm): 1.39 (3H, t, J=7 Hz), 2.57 (1H, t, J=2 Hz), 4.36 (2H, q, J=7 Hz), 4.56 (2H, s), 4.86 (2H, d, J=2 Hz).

(3) Ethyl 4-chloro-3-oxo-2-propargyloxyiminobutyrate (syn isomer, 61 g.), thiourea (20 g.), sodium acetate 3-hydrate (35.8 g.), water (150 ml.), and ethanol (180 ml.) were treated in a similar manner to that of Example F-(3) to give ethyl 2-(2-aminothiazol-4-yl)-2-propargyloxyiminoacetate (syn isomer, 35.6 g.).

I.R. $\nu_{max}^{Nujol}$: 3290, 2220, 1729 cm$^{-1}$.

N.M.R. δ(DMSO-d$_6$, ppm): 1.28 (3H, t, J=7 Hz), 3.49 (1H, t, J=3 Hz), 4.31 (2H, q, J=7 Hz), 4.76 (2H, d, J=3 Hz), 6.95 (1H, s), 7.29 (2H, s). p (4) Ethyl 2-(2-aminothiazol-4-yl)-2-propargyloxyiminoacetate (syn isomer, 2.8 g.), methanol (23 ml.), tetrahydrofuran (20 ml.) and 1 N aqueous solution of sodium hydroxide (22.17 ml.) were treated in a similar manner to that of Example F-(4) to give 2-(2-aminothiazol-4-yl)-2-propargyloxyiminoacetic acid (syn isomer, 1.924 g.).

I.R. $\nu_{max}^{Nujol}$: 2190, 1740.

N.M.R. δ(DMSO-d$_6$, ppm): 3.47 (1H, t, J=1.5 Hz), 4.74 (2H, d, J=1.5 Hz), 6.90 (1H, s).

EXAMPLE J (1) Ethyl 2-hydroxyimino-3-oxobutyrate (syn isomer, 40 g.), N,N-dimethylformaide (200 ml.), potassium carbonate (52 g.) and n-hexyl bromide (41.4 g.) were treated in a similar manner to that of Example F-(1) to give ethyl 2-n-hexyloxyimino-3-oxobutyrate (syn isomer, 60.7 g.), oil.

I.R. $\theta_{max}^{Film}$: 1740, 1705, 1700 cm$^{-1}$.

N.M.R. δ(CCl$_4$, ppm): 0.6~2.1 (14H, m), 2.37 (3H, s), 4.1~4.6 (4H, m).

(2) Ethyl 2-n-hexyloxyimino-3-oxobutyrate (syn isomer, 60.7 g.), acetic acid (61 ml.) and sulfuryl chloride (34.7 g.) were treated in a similar manner to that of Example F-(2) to give ethyl 2-n-hexyloxyimino-4-chloro-3-oxobutyrate (syn isomer, 55.6 g.).

I.R. $\nu_{max}^{Film}$: 1740, 1720, 1470 cm$^{-1}$.

N.M.R. δ(CCl$_4$, ppm): 0.6~2.2 (14H, m), 4.1~4.6 (4H, m), 4.47 (2H, s).

(3) Ethyl 2-n-hexyloxyimino-4-chloro-3-oxobutyrate (syn isomer, 55.6 g.), thiourea (15.2 g.), sodium acetate 3-hydrate (27.2 g) ethanol (280 ml.) and water (140 ml.) were treated in a similar manner to that of Example F-(3) to give ethyl 2-(2-aminothiazol-4-yl)-2-n-hexyloxyiminoacetate (syn isomer, 29.3 g.) mp 77° to 78° C.

I.R. $\nu_{max}^{Nujol}$: 3460, 3250, 3140, 1720, 1535 cm$^{-1}$.

N.M.R. δ(DMSO-d$_6$): 0.85 (3H, t, J=6 Hz), 1.0~1.9 (11H, m), 2.07 (2H, t, J=6 Hz), 2.26 (2H, q, J=7 Hz), 6.85 (1H, s), 7.22 (2H, s).

(4) Ethyl 2-(2-aminothiazol-4-yl)-2-n-hexyloxyiminoacetate (syn isomer, 29.1 g.), methanol (97.2 ml.), 2 N aqueous solution of sodium hydroxide (97.2 ml.) and tetrahydrofuran (50 ml.) were treated in a similar manner to that of Example F-(4) to give 2-(2-aminothiazol-4-yl)-2-n-hexyloxyiminoacetate acid (syn isomer, 24.0 g.), mp. 174° C. (dec.

I.R. $\nu_{max}^{Nujol}$: 1660, 1625, 1425 cm$^{-1}$.

N.M.R. δ(DMSO-d$_6$, ppm) 0.6~2.1 (11H, m), 4.07 (2H, t, J=6 Hz), 6.83 (1H, s), 7.19 (2H, s).

EXAMPLE K (1) Ethyl 2-hydroxyimino-3-oxobutyrate (syn isomer, 40 g.), N,N-dimethylformamide (200 ml.), potassium carbonate (52 g.) and pentyl bromide (37.9 g.) were treated in a similar manner to that of Example F-(1) to give ethyl 2-pentyloxyimino-3-oxobutyrate (syn isomer, 57.5 g.), oil.

I.R. $\nu_{max}^{Film}$: 1745, 1680, 1470 cm$^{-1}$.

N.M.R. δ (CCl$_4$, ppm): 0.7~2.2 (12H, m), 2.36 (3H, s), 4.1-4.6 (4H, m).

(2) Ethyl 2-pentyloxyimino-3-oxobutyrate (syn isomer, 57.5 g.), acetic acid (58.5 ml.) and sulfuryl chloride (20.9 ml.) were treated in a similar manner to that of Example F-(2) to give ethyl 2-pentyloxyimino-4-chloro-3-oxobutyrate (syn isomer, 51.1 g.) oil.

I.R. $\nu_{max}^{Film}$: 1750, 1715, 1470 cm$^{-1}$.

N.M.R. δ(CCl$_4$, ppm): 0.7~2.1 (11H, m), 4.1~4.6 (4H, m), 4.48 (2H, s).

(3) Ethyl 2-pentyloxyimino-4-chloro-3-oxobutyrate (syn isomer, 51.1 g.), thiourea (14.7 g.), sodium acetate trihydrate (26.4 g.), ethanol (175 ml.) and water (125 ml.), were treated in a similar manner to that of Example F-(3) to give ethyl 2-(2-aminothiazol-4-yl)-2-pentyloxyiminoacetate (syn isomer, 28.7 g.), mp. 86° to 88° C.

I.R. $\nu_{max}^{Nujol}$: 3450, 3250, 3130, 1715, 1535 cm$^{-1}$.

N.M.R. δ(DMSO-d$_6$, ppm): 0.6-2.0 (12H, m), 4.11 (2H, t, J=6 Hz), 4.32 (2H, q, J=7 Hz), 6.90 (1H, s), 7.25 (2H, s).

(4) Ethyl 2-(2-aminothiazol-4-yl)-2-pentyloxyiminoacetate (syn isomer, 28.6 g.), 2 N aqueous solution of sodium hydroxide (100.2 ml.), methanol (100 ml.) and tetrahydrofuran (100 ml.) were treated in a similar manner to that of Example F-(4) to give 2-(2-aminothiazol-4-yl)-2-pentyloxyiminoacetic acid (syn isomer, 22.4 g.), mp 176° C. (dec.).

I.R. $\nu_{max}^{Nujol}$: 3160, 1655, 1620, 1460 cm$^{<1}$.

N.M.R. δ(DMSO-d$_6$, ppm): 0.6-2.2 (9H, m), 4.07 (2H, t, J=6 Hz), 6.82 (1H, s), 7.20 (2H, s).

(5) 2-(2-Aminothiazol-4-yl)-2-pentyloxyiminoacetic acid (syn isomer, 15 g.), acetic anhydride (23.8 g.) and formic acid (10.7 g.) were treated in a similar manner to that of Example F-(5) to give 2-(2-formamidothiazol-4-yl)-2-pentyloxyiminoacetic acid (syn isomer, 14.7 g.), mp 125° C. (dec.).

I.R. $\nu_{max}^{Nujol}$: 3200, 3140, 1700, 1565 cm$^{-1}$.

N.M.R. δ(DMSO-d$_6$, ppm): 0.6-2.0 (9H, m), 4.13 (2H, t, J=6 Hz), 7.53 (1H, s), 7.54 (1H, s), 12.66 (1H, s).

EXAMPLE L (1) Allyl bromide (2.91 g.) was added dropwise to a stirred suspension of ethyl 2-(2-tritylaminothiazol-4-yl)-2-hydroxyiminoacetate (syn isomer, 10 g.), N,N-dimethylformamide (100 ml.) and potassium carbonate (4.54 g.) under ice cooling over 5 minutes, and stirred at the same temperature for 4 hours. After adding water (200 ml.) to the resultant solution, the solution was extracted with diethyl ether twice. The extract was washed with a saturated aqueous solution of sodium chloride and dried over magnesium sulfate. The solution was concentrated in vacuo, and the residue was triturated with a solution of n-hexane and diethyl ether. The precipitates were collected by filtration to give ethyl 2-(2-tritylaminothiazol-4-yl)-2-allyloxyiminoacetate (syn isomer, 9.4 g.), mp. 130° to 132° C.

I.R. $\nu_{max}^{Nujol}$: 3380, 1735, 1520, 1500 cm$^{-1}$.

N.M.R. δ (DMSO-d$_6$, ppm): 1.08 (3H, t, J=7 Hz), 3.96 (2H, q, J=7 Hz), 4.54 (2H, broad d, J=5 Hz), 5.0~5.5 (2H, m), 5.6~6.3 (1H, m), 6.90 (15H, broad s), 7.74 (1H, s).

(2) A solution of ethyl 2-(2-tritylaminothiazol-4-yl)-2-allyloxyiminoacetate (syn isomer, 8.7 g.), 50% formic acid (42.5 ml.) and tetrahydrofuran (42.5 ml.) was stirred at 60° C. for 40 minutes. After concentrating the resultant solution in vacuo, the residue was dissolved in ethyl acetate, washed with an aqueous solution of sodium bicarbonate and a saturated aqueous solution of sodium chloride in turn, and dried over magnesium sulfate. After concentrating the resultant solution in vacuo, the residue was subjected to column chromatography on silica gel with benzene and ethyl acetate in turn, to give ethyl 2-(2-aminothiazol-4-yl)-2-allyloxyiminoacetate (syn isomer, 3.7 g.), mp. 102° to 104° C.

I.R. $\nu_{max}^{Nujol}$: 3460, 3260, 3130, 1725, 1620, 1540, 1460 cm$^{-1}$.

N.M.R. δ (DMSO-d$_6$, ppm): 1.25 (3H, t, J=7 Hz), 4.30 (2H, q, J=7 Hz), 4.61 (2H, dd, J=5 Hz, 1 Hz), 5.0~5.5 (2H, m), 5.6~6.5 (1H, m), 6.95 (1H, s), 7.28 (2H, s).

(3) A solution of ethyl 2-(2-aminothiazol-4-yl)-2-allyloxyiminoacetate (syn isomer, 3.6 g.), 2 N aqueous solution of sodium hydroxide (14.1 ml.), tetrahydrofuran (14.1 ml.) and methanol (15 ml.) was stirred at 40° C. for 1.5 hours. The resultant solution was concentrated in vacuo, and the residue was dissolved in water. After the solution was adjusted to pH 2.8 with 10% hydrochloric acid under ice cooling, the precipitates were collected by filtration, washed with water and acetone in turn and dried to give 2-(2-aminothiazol-4-yl)-2-allyloxyiminoacetic acid (syn isomer, 1.91 g.), mp. 187° C. (dec.).

I.R. $\nu_{max}^{Nujol}$: 3350, 1630, 1580, 1460 cm$^{-1}$.

N.M.R. δ (DMSO-d$_6$, ppm): 4.61 (2H, d, J=6 Hz), 5.1~5.5 (2H, m), 5.7~6.2 (1H, m), 6.84 (1H, s), 7.25 (2H, broad s).

EXAMPLE M (1) Propargyl bromide (4.16 g.) was added to a suspension of ethyl 2-(2-tritylaminothiazol-4-yl)-2-hydroxyiminoacetate (syn isomer, 10 g.), potassium carbonate (4.84 g.) and N,N-dimethylformamide (22 ml.) under atmosphere of nitrogen gas and stirred at room temperature for 100 minutes. The insoluble substance was filtered off and washed with a little of N,N-dimethylformamide. The filtrate and washing solution were combined together, and water (400 ml.) was added to the solution. After the suspension was extracted with ethyl acetate (400 ml.), the extract was washed with a saturated aqueous solution of sodium chloride and dried over magnesium sulfate. After treating the solution with activated charcoal, the solution was concentrated in vacuo. The residue was triturated with diisopropyl ether. The precipitates were collected by filtration, and washed with diisopropyl ether to give ethyl 2-(2-tritylaminothiazol-4-yl)-2-propargyloxyiminoacetate (syn isomer, 8.34 g.).

I.R. $\nu_{max}^{Nujol}$: 3290, 2225, 1735 cm$^{-1}$.

N.M.R. δ (DMSO-d$_6$, ppm): 1.12 (3H, t, J=7 Hz), 3.47 (1H, t, J=3 Hz), 3.97 (2H, q, J=7 Hz), 4.67 (2H, d, J=3 Hz), 6.95 (1H, s), 7.26 (15H, s), 8.77 (1H, s).

(2) 50% Formic acid (41 ml.) was added to a solution of ethyl 2-(2-tritylaminothiazol-4-yl)-2-propargyloxyiminoacetate (syn isomer, 8.2 g.) and tetrahydrofuran (41 ml.), and stirred at 60° C. for an hour. The resultant solution was concentrated to a half of initial volume under reduced pressure, and the precipitates were collected by filtration and washed with diisopropyl ether. The filtrate and washing solution were combined together and concentrated in vacuo. The residue was added to ethyl acetate (200 ml.) under stirring. The insoluble substance was collected by filtration, and washed with diethyl ether to give ethyl 2-(2-aminothiazol-4-yl)-2-propargyloxyiminoacetate (syn isomer, 0.3 g.). The filtrate and ethyl acetate washing solution were combined together, washed with a saturated aqueous solution of sodium bicarbonate and a saturated aqueous solution of sodium chloride twice in turn, and dried over magnesium sulfate. The solution was treated with activated charcoal and concentrated in vacuo. The residue was dried in vacuo after adding benzene. The residue was subjected to column chromatography on silica gel with benzene and ethyl acetate in turn. The eluate was concentrated in vacuo, and the residue was triturated with diisopropyl ether. The precipitates were collected by filtration, washed with diisopropyl ether to give the same compound as mentioned above (syn isomer, 2.658 g.). The I.R. spectrum and N.M.R. spectrum are the same as those of the compound obtained in Example I-(3).

EXAMPLE N

Sodium bicarbonate (0.84 g.) was added to a suspension of 2-(2-formamidothiazol-4-yl)oxalic acid (2 g.) in water (120 ml.) to prepare a solution. Ethyl 2-aminoxyacetate hydrochloride (4.56 g.) was added to the solution and stirred at room temperature for 3 hours while adjusting to pH 6 with sodium bicarbonate. The resultant solution was adjusted to pH 1.5 with hydrochloric acid, salted out and extracted with ethyl acetate three times. The extract was dried over magnesium sulfate and concentrated in vacuo. The residue was pulverized with diethyl ether, and the precipitates were collected by filtration and dried to give 2-(2-formamidothiazol-4-yl)-2-ethoxycarbonylmethoxyiminoacetic acid (syn isomer, 1.44 g.), mp 112° C. (dec.).

I.R. $\nu_{max}^{Nujol}$: 3150, 1740, 1670, 1550 cm$^{-1}$.

N.M.R. δ(DMSO-d$_6$, ppm): 1.23 (3H, t, J=7Hz), 4.16 (2H, q, J=7Hz), 4.77 (2H, s), 7.56 (1H, s), 8.54 (1H, s).

EXAMPLE O (1) Ethyl 2-hydroxyimino-3-oxobutyrate (syn isomer, 60 g.), 1-bromo-2-chloroethane (54.1 g.), potassium carbonate (78 g.) and N,N-dimethylformamide (200 ml.) were treated in a similar manner to that of Example F-(1) to give ethyl 2-(2-chloroethoxyimino)-3-oxobutyrate (syn isomer, 83.6 g.), oil.

I.R. $\nu_{max}^{Film}$: 1740, 1680, 1430 cm$^{-1}$.

N.M.R. δ(CCl$_4$, ppm): 1.34 (3H, t, J=7Hz), 2.34 (3H, s), 3.72 (2H, t, J=6Hz), 4.28 (2H, q, J=7Hz), 4.46 (2H, t, J=6Hz).

(2) Ethyl 2-(2-chloroethoxyimino)-3-oxobutyrate (syn isomer, 83.6 g.), sulfury chloride (52.4 g.) and acetic acid (83.6 ml.) were treated in a similar manner to that of Example F-(2) to give Ethyl 2-(2-chloroethoxyimino)-3-oxo-4-chlorobutyrate (syn isomer, 68 g.), oil.

I.R. $\nu_{max}^{Film}$: 1740, 1720 cm$^{-1}$.

N.M.R. δ (CCl$_4$, ppm): 1.32 (3H, t, J=7Hz), 3.70 (2H, t, J=6Hz), 4.29 (2H, q, J=7Hz), 4.47 (2H, s), 4.48 (2H, t, J=6Hz).

(3) Ethyl 2-(2-chloroethoxyimino)-3-oxo-4-chlorobutyrate (syn isomer, 68 g.), thiourea (20.2 g.), sodium acetate trihydrate (36.2 g.), ethanol (270 ml.) and water (170 ml.) were treated in a similar manner to that of Example F-(3) to give ethyl 2-(2-aminothiazol-4-yl)-2-(2-chloroethoxyimino)acetate (syn isomer, 33.7 g.), mp 126° to 128° C.

I.R. $\nu_{max}^{Nujol}$: 3440, 3260, 3140, 1725, 1620, 1540 cm$^{-1}$.

N.M.R. δ(DMSO-d$_6$, ppm): 1.30 (3H, t, J=7Hz), 3.78 (2H, t, J=6Hz), 4.1–4.6 (4H, m), 6.96 (1H, s), 7.27 (2H, s).

(4) Ethyl 2-(2-aminothiazol-4-yl)-2-(2-chloroethoxyimino)acetate (syn isomer, 30.5 g.), 1N aqueous solution of sodium hydroxide (220 ml.), methanol (110 ml.) and tetrahydrofuran (140 ml.) were treated in a similar manner to that of Example F-(4) to give 2-(2-aminothiazol-4-yl)-2-(2-chloroethoxyimino)-acetic acid (syn isomer, 23.4 g.), mp 201° C. (dec.).

I.R. $\nu_{max}^{Nujol}$: 3210, 3100, 1640, 1620, 1580 cm$^{-1}$.

N.M.R. δ(DMSO-d$_6$, ppm): 3.83 (2H, t, J=6Hz), 4.36 (2H, t, J=6Hz), 6.92 (1H, s), 7.30 (2H, s).

(5) 2-(2-Aminothiazol-4-yl)-2-(2-chloroethoxyimino)acetic acid (syn isomer, 15 g.), acetic anhydride (24.5 g.), formic acid (11.0 g.) and tetrahydrofuran (50 ml.) were treated in a similar manner to that of Example F-(5) to give 2-(2-formamidothiazol-4-yl)-2-(2-chloroethoxyimino)acetic acid (syn isomer, 13.4 g.), mp 155° C. (dec.).

I.R. $\nu_{max}^{Nujol}$: 3100, 1740, 1690, 1660 cm$^{-1}$.

N.M.R. δ(DMSO-d$_6$, ppm): 3.87 (2H, t, J=6Hz), 4.40 (2H, t, J=6Hz), 7.60 (1H, s), 8.56 (1H, s), 12.62 (1H, broad s).

EXAMPLE P

A suspension of 2-(2-formamidothiazol-4-yl)oxalic acid (3.0 g.) in methanol (60 ml.) and water (60 ml.) was adjusted to pH 8 with 1N aqueous solution of sodium hydroxide under stirring. 2,2,2-Trifluoroethoxyamine hydrochloride (2.24 g.) was added to the solution, and the solution was adjusted to pH 2.5 to 3 with 1N aqueous solution of sodium hydroxide. After the solution was stirred at room temperature for 1.5 hours, methanol was removed from the resultant solution under reduced pressure. The concentrated aqueous solution was adjusted to pH 7 with 1N aqueous solution of sodium hydroxide and washed with ethyl acetate. Ethyl acetate was added to the aqueous solution and adjusted to pH 1.5 with 10% hydrochloric acid, and then extracted with ethyl acetate. The aqueous layer was extracted again with ethyl acetate. The extracts were combined, washed with a saturated aqueous solution of sodium chloride and dried over magnesium sulfate. The solution was concentrated in vacuo to give 2-(2-formamidothiazol-4-yl)-2-(2,2,2-trifluoroethoxyimino)acetic acid (syn isomer, 2.4 g.), mp 162° to 163° C. (dec.).

I.R. $\nu_{max}^{Nujol}$: 3200, 1700, 1600, 1560 cm$^{-1}$.

N.M.R. δ(DMSO-d$_6$, ppm): 4.83 (2H, q, J=8.5Hz), 7.65 (1H, s), 8.58 (1H, s), 12.60 (1H, broad s).

EXAMPLE Q 2-(2-Formamidothiazol-4-yl)oxalic acid (10 g.), sodium bicarbonate (4.2 g.) and tert-butyl 2-aminooxyacetate (8.1 g.) were treated in a similar manner to that of Example N to give an oil. The oil was triturated with n-hexane and the precipitates were collected by filtration and dried to give 2-(2-formamidothiazol-4-yl)-2-tert-butoxycarbonylmethoxyiminoacetic acid (syn isomer, 11.3 g.), mp 117° C. (dec.).

I.R. $\nu_{max}^{Nujol}$: 3180, 3140, 1750, 1690, 1630 cm$^{-1}$.

N.M.R. δ(DMSO-d$_6$, ppm): 1.46 (9H, s), 4.66 (2H, s), 7.56 (1H, s), 8.56 (1H, s), 12.67 (1H, broad s).

EXAMPLE 1

(1) N,N-Dimethylformamide (0.16 g.) and phosphorous oxychloride (0.34 g.) were mixed to prepare Vilsmeier reagent in a usual manner, and the resultant Vilsmeier reagent was suspended in dry ethyl acetate. To the suspension was added 2-(2-formamido-4-thiazolyl)-2-methoxyiminoacetic acid (syn isomer, 0.46 g.) under ice-cooling with stirring, and then the solution was stirred at the same temperature for 30 minutes to prepare the activated acid solution. p-Nitrobenzyl 7-amino-3-chloro-3-cephem-4-carboxylate hydrochloride (0.81 g.) was dissolved in a solution of trimethylsilylacetamide (2.10 g.) in ethyl acetate (200 ml.). To the solution was added the activated acid solution obtained above all at once at −20° C., and the solution was stirred at −20°∼−5° C. for 1.5 hours. After water and ethyl acetate (100 ml.) were added to the resultant solution at −20° C., the insoluble product was separated by filtration, washed with water and acetone in turn and then dried to give p-nitrobenzyl 7-{2-(2-formamido-4-thiazolyl)-2-methoxyiminoacetamido}-3-chloro-3-cephem-4-carboxylate (syn isomer, 0.6 g.). After ethyl acetate was removed from the above filtrate, the aqueous layer was extracted with ethyl acetate (50 ml.) twice. The ethyl acetate layer and the extract were combined together, washed with 10% hydrochloric acid, a saturated aqueous solution of sodium bicarbonate and a saturated aqueous solution of sodium chloride in turn and then dried over magnesium sulfate. After removing ethyl acetate from the solution, diethyl ether was added to the residue. The insoluble product was collected by filtration to give the same object compound (0.25 g.), m.p. 226° to 228° C. (dec.), Total yield 0.85 g.

I.R. $\nu_{max}^{Nujol}$: 3250, 1780, 1720, 1685, 1645, 1605, 1550, 1520 cm$^{-1}$.

N.M.R. δ$_{ppm}$ (DMSO-d$_6$): 3.45 (2H, broad s), 3.93 (3H, s), 5.35 (1H, d, J=5Hz), 5.50 (2H, s), 5.95 (1H, dd, J=5,8Hz), 7.43 (1H, s), 7.72 (2H, d, J=9Hz), 8.28 (2H, d, J=9Hz), 8.55 (1H, s), 9.80 (1H, d, J=8Hz).

(2) p-Nitrobenzyl 7-{2-(2-formamido-4-thiazolyl)-2-methoxyiminoacetamido}-3-chloro-3-cephem-4-carboxylate (syn isomer, 0.8 g.) was dissolved in a mixed solution of methanol (30 ml.) and tetrahydrofuran (60 ml.). After adding 10% palladium carbon (0.4 g.) to the solution, the mixture was subjected to catalytic reduction at room temperature under atmospheric pressure. The catalyst was filtered off, and the filtrate was concentrated under reduced pressure. Water (30 ml.) was added to the residue and the mixture was adjusted to pH 7.5 with an aqueous solution of sodium bicarbonate. After removing the insoluble substance from the mixture by filtration, the filtrate was washed with ethyl acetate (50 ml.). Ethyl acetate (70 ml.) was added to the solution, and the mixture was adjusted to pH 1.5 with 10% hydrochloric acid and then shaked sufficiently. After the ethyl acetate layer was removed, the aqueous layer was extracted with ethyl acetate (30 ml.) twice. The ethyl acetate layer and the extracts were combined together, washed with a saturated aqueous solution of sodium chloride, dried over magnesium sulfate and then concentrated under reduced pressure to give 7-{2-(2-formamido-4-thiazolyl)-2-methoxyiminoacetamido}-3-chloro-3-cephem-4-carboxylic acid (syn isomer 0.48 g.), m.p. 165° to 174° C. (dec.).

I.R. $\nu_{max}^{Nujol}$: 3250, 1780, 1730, 1690, 1660, 1550 cm$^{-1}$.

N.M.R. $\delta_{ppm}$ (DMSO-d$_6$): 3.57 (2H, broad s), 3.91 (3H, s), 5.30 (1H, d, J=5Hz), 5.88 (1H, dd, J=5, 8Hz), 7.44 (1H, s), 8.52 (1H, s), 9.78 (1H, d, J=8Hz), 12.60 (1H, s).

(3) 7-{2-(2-Formamido-4-thiazolyl)-2-methoxyiminoacetamido}-3-chloro-3-cephem-4-carboxylic acid(syn isomer, 0.4 g.) was suspended in methanol (15 ml.). After adding conc-hydrochloric acid (0.16 g.) to the suspension, the mixture was stirred at room temperature for 2.5 hours. Methanol was distilled off from the resultant mixture under reduced pressure, and the residue was dissolved in water (15 ml.). The solution was washed with ethyl acetate (30 ml.) and dichloromethane (30 ml.) in turn. To the acqueous layer was introduced nitrogen gas to remove the remaining organic solvent completely, and the solution was lyophilized to give 7-{2-(2-amino-4-thiazolyl)-2-methoxyiminoacetamido}-3-chloro-3-cephem-4-carboxylic acid hydrochloride (syn isomer 0.35 g.), m.p. 170° to 180° C. (dec.)

I.R. $\nu_{max}^{Nujol}$: 3300, 1780, 1730, 1670, 1630, 1545 cm$^{-1}$.

N.M.R. $\delta_{ppm}$ (DMSO-d$_6$): 3.88 (2H, AB-q, J=17Hz), 3.94 (3H, s), 5.26 (1H, d, J=5Hz), 5.80 (1H, dd, J=5, 8Hz), 6.92 (1H, s), 9.88 (1H, d, J=8Hz).

(4) 7-[2-(2-Amino-4-thiazolyl)-2-methoxyiminoacetamido]-3-chloro-3-cephem-4-carboxylic acid hydrochloride (syn-isomer: 1.5 g.) and sodium bicarbonate (0.56 g.) were dissolved in water (50 ml.) at room temperature with stirring and lyophilized. A solution of iodomethyl hexanoate (0.93 g.) in dimethylformamide (5 ml.) was added dropwise to a solution of the product obtained above in dimethylformamide (15 ml.) at −5° C. and stirred at the same temperature for 30 minutes. Ethyl acetate (50 ml.) and water (100 ml.) were added to the resultant solution and the ethyl acetate layer was separated. The aqueous layer was extracted with ethyl acetate (50 ml.) twice. The extracts were combined with the ethyl acetate layer, washed with a saturated aqueous solution of sodium bicarbonate three times and a saturated aqueous solution of sodium chloride three times in turn, dried over magnesium sulfate, treated with activated charcoal and then concentrated under reduced pressure. After washing the concentrate with n-hexane (50 ml.), n-hexane (50 ml.) and diethylether (25 ml.) were added to the residue and allowed to stand in a refrigerator overnight. The precipitating powder was collected by filtration, washed with n-hexane and dried to give a mixture (1.0 g.) of n-hexanoyloxymethyl 7-[2-(2-amino-4-thiazolyl-2-methoxyiminoacetamido]-3-chloro-3-cephem-4-carboxylate (syn-isomer) and n-hexanoyloxymethyl 7-[2-(2-amino-4-thiazolyl)-2-methoxyiminoacetamido]-3-chloro-2-cephem-4-carboxylate (syn-isomer).

(5) Thus obtained mixture (1.0 g.) was added to methylene chloride (10 ml.) To the solution were added acetic acid (7 ml.), a solution of sodium tungstate (Na$_2$WO$_4$.2H$_2$O) (20 mg.) in water (0.5 ml.), methylene chloride (5 ml.) and 35% hydrogen peroxide (180 mg.), and then stirred under ice-cooling for 4 hours. Ice-water was added to the resultant solution and extracted with methylene chloride. The extract was washed with water, dried over magnesium sulfate and concentrated under reduced pressure. The residue was pulverized with diethyl ether (20 ml.), washed with diethyl ether (10 ml.) twice and dried. The product was purified with column chromatography on silica gel (eluent: ethyl acetate) to give n-hexanoyloxymethyl 7-[2-(2-amino-4-thiazolyl)-2-methoxyiminoacetamido]-3-chloro-3-cephem-4-carboxylate-1-oxide (syn-isomer: 600 mg.)

I.R. $\nu_{max}^{Nujol}$: 3300, 1790, 1760, 1680, 1630, 1540, 1380 cm$^{-1}$.

N.M.R. $\delta$ppm (DMSO-d$_6$): 0.67–2.5 (11H, m), 3.90 (3H, s), 4.20 (2H, broad s), 5.17 (1H, d), 5.83–6.17 (3H, m), 6.88 (1H, s), 9.17 (1H, d).

(6) Phosphorus trichloride (210 mg.) was added to a solution of n-hexanoyloxymethyl 7-[2-(2-amino-4-thiazolyl)-2-methoxyiminoacetamido]-3-chloro-3-cephem-4-carboxylate-1-oxide (syn-isomer: 570 mg.) in dry dimethylformamide (10 ml.) at −30° C., and stirred at −20° to −30° C. for 50 minutes. 10% aqueous solution (50 ml.) of sodium chloride was added to the resultant solution, adjusted to pH 8.0 with a saturated aqueous solution of sodium bicarbonate and extracted with ethyl acetate. The extract was washed with a saturated aqueous solution of sodium bicarbonate and a saturated aqueous solution of sodium chloride, dried over magnesium sulfate, and then concentrated under reduced pressure. The residue (560 mg.) was purified with column chromatography on silica gel (20 g.) eluent:ethyl acetate), and the resultant residue (180 mg.) was pulverized with n-hexane (10 ml.) and diethyl ether (5 ml.) to give n-hexanoyloxymethyl 7-[2-(2-amino-4-thiazolyl)-2-methoxyiminoacetamido]-3-chloro-3-cephem-4-carboxylate (syn-isomer: 150 mg.).

I.R. $\nu_{max}^{Nujol}$: 3400 (broad), 1780 (broad), 1760 (shoulder), 1670, 1620, 1530 cm$^{-1}$.

N.M.R. $\delta$ppm (CDCl$_3$): 0.67–2.5 (11H, m), 3.67 (2H, q), 4.00 (3H, s), 5.17(1H, d), 5.90 (1H, s), 6.00 (1H, m), 6.77 (1H, s), 7.83 (1H, d).

EXAMPLE 2

(1) 2-{2-(2,2,2-Trifluoroacetamido)-4-thiazolyl}-2-methoxyiminoacetic acid (syn isomer, 0.65 g.) was added at 0° C. to Vilsmeier reagent which had been prepared from dimethylformamide and phosphorus oxychloride in ethyl acetate (10 ml.), and the mixture was stirred at the same temperature for 40 minutes to prepare the activated acid solution. The activated acid solution was added dropwise to a solution of 7-amino-2,3-dimethyl-3-cephem-4-carboxylic acid (0.5 g.) and trimethylsilylacetamide (1.73 g.) in ethyl acetate (30 ml.) at −20° C., and the mixture was stirred at the same temperature for 40 minutes. To the resultant mixture was added water (10 ml.), and the ethyl acetate layer was separated from the mixture and washed with water. Water (30 ml.) was added to the solution and the mixture was adjusted to pH 7.5 with sodium bicarbonate under ice-cooling. After shaking the mixture, the aqueous layer was separated. Ethyl acetate (50 ml.) was added to the aqueous solution, and the mixture was adjusted to pH 2 with dilute hydrochloric acid with stirring, and the ethyl acetate layer was separated, washed with water and a saturated aqueous solution of sodium chloride in turn, treated with activated charcoal, dried over magnesium sulfate and then concentrated under reduced pressure. The residue was pulverized with diisopropyl ether to give 7-[2-{2-(2,2,2-trifluoroacetamido)-4-thiazolyl}-2-methoxyiminoacetamido]-2,3-dimethyl-3-cephem-4-carboxylic acid (syn isomer, 0.9 g.).

I.R. $\nu_{max}^{Nujol}$: 3250, 1780, 1725, 1680, 1650 cm$^{-1}$.

N.M.R. $\delta_{ppm}$(DMSO-d$_6$): 1.43(3H, d, J=8 Hz), 1,92(1H, s), 3.82(3H, s), 3.98(1H, q, J=8 Hz), 5.18 (1H, d, J=6Hz), 5.73 (1H, AB-q, J=6Hz), 7.43 (1H, s), 9.63 (1H, d, J=8 Hz).

(2) 7-[2-{2-(2,2,2-Trifluoroacetamido)-4-thiazolyl}--2-methoxyiminoacetamido]-2,3-dimethyl-3-cephem-4-carboxylic acid (syn isomer, 0.86 g.) was dissolved in an aqueous solution (9 ml.) containing sodium acetate trihydrate (2.3 g.), and the solution was stirred at room temperature for 19 hours. After removing the insoluble substance from the resultant mixture by filtration, the filtrate was adjusted to around pH 2.5 with 10% hydrochloric acid under ice-cooling. The precipitates were collected by filtration, washed with water and dried to give 7-{2-(2-amino-4-thiazolyl)-2-methoxyiminoacetamido}-2,3-dimethyl-3-cephem-4-carboxylic acid (syn isomer, 0.16 g.).

I.R. $\nu_{max}^{Nujol}$: 3320, 3200, 1770 (shoulder), 1670, 1630 cm$^{-1}$.

N.M.R. $\delta_{ppm}$(DMSO-d$_6$): 1.44(3H, d, J=7 Hz), 1.98 (3H, s), 3.57 (1H, q, J=7 Hz), 3.82 (3H, s), 5.18 (1H, d, J=5 Hz), 5.73 (1H, dd, J=5, 8 Hz), 6.76 (1H, s), 9.63 (1H, d, J=8 Hz).

EXAMPLE 3

(1) A mixture of 2-{2-(2,2,2-trifluoroacetamido)-4-thiazolyl}-2-methoxyiminoacetic acid (syn isomer, 0.8 g.), dimethylformamide (0.20 g.), phosphorus oxychloride (0.41 g.) and ethyl acetate (10 ml.) was stirred for 30 minutes under ice-cooling to prepare the activated acid solution in a similar manner to that of Example 4. On the other hand, a solution of 7-amino-3-methoxy-3-cephem-4-carboxylic acid hydrochloride (0.6 g.) and trimethylsilylacetamide (3 g.) in ethyl acetate (15 ml.) was stirred at 40° C. for 3 hours. To the solution was added dropwise the activated acid solution at −10° to −20° C. in 2 minutes, and the mixture was stirred at the same temperature for 1.5 hours. After water (10 ml.) was added to the resultant mixture, the ethyl acetate layer was separated and allowed to stand. The precipitates were collected by filtration to give 7-[2-{2-(2,2,2-trifluoroacetamido)-4-thiazolyl}-2-methoxyiminoacetamido]-3-methoxy-3-cephem-4-carboxylic acid (syn isomer, 0.3 g.). The aqueous layer, which was separated from the ethyl acetate layer, was extracted with ethyl acetate, and the extract was combined with the mother liquor obtained above. The ethyl acetate solution was washed with a saturated aqueous solution of sodium chloride, dried over magnesium sulfate and then filtered. The filtrate was concentrated under reduced pressure, and the residue was washed with diethyl ether to give the same object compound (0.25 g.), Total yield 0.55 g.

I.R. $\nu_{max}^{Nujol}$: 3230, 1770, 1715, 1650, 1580 cm$^{-1}$.

N.M.R. $\delta_{ppm}$(DMSO-d$_6$): 3.62 (2H, AB-q, J=16 Hz), 3.78 (3H, s), 3.93 (3H, s), 5.17 (1H, d, J=4 Hz), 5.54 (1H, dd, J=8, 4 Hz), 7.60 (1H, s), 9.69 (1H, d, J=8 Hz).

(2) A solution of 7-[2-{2-(2,2,2-trifluoroacetamido)-4-thiazolyl}-2-methoxyiminoacetamido]-3-methoxy-3-cephem-4-carboxylic acid (syn isomer, 0.55 g.) and sodium acetate trihydrate (1,76 g.) in ethyl acetate (3 ml.), tetrahydrofuran (3 ml.) and water (5.5 ml.) was stirred at room temperature overnight. The aqueous layer was separated from the resultant mixture, washed with dichloromethane, and then evaporated under reduced pressure to remove the organic solvent. The aqueous solution was adjusted to pH 4.2 under ice-cooling, and subjected to column chromatography on Diaion HP-20 resin (Trade mark: manufactured by Mitsubishi Chemical Industries Ltd., 15 ml.). After washing the column with water, the object compound was eluted with 20% aqueous isopropyl alcohol. The eluate was concentrated under reduced pressure and the residue was lyophilized to give 7-{2-(2-amino-4-thiazolyl)-2-methoxyiminoacetamido}-3-methoxy-3-cephem-4-carboxylic acid (syn isomer 0.4 g.), m.p. 185° to 190° C. (dec.).

I.R. $\nu_{max}^{Nujol}$: 3300, 1770, 1660, 1630, 1540 cm$^{-1}$.

N.M.R. $\delta_{ppm}$(DMSO-d$_6$): 3.60 (2H, broad s), 3.75(3H, s), 3.83(3H, s), 5.12 (1H, d, J=4 Hz), 5.55(1H, dd, J=4,8 Hz), 6.82(1H, s), 9.52(1H, d, J=8 Hz).

EXAMPLE 4

(1) To a suspension of p-nitrobenzyl 7-phenylacetamido-3-cephem-4-carboxylate (10.50 g.) in dry dichloromethane (100 ml.) was added dry pyridine (2.14 g.). Phosphorus pentachloride (5.50 g.) was added to the solution at −10° C., and the mixture was stirred at −5° C. for 45 minutes and further at 10° C. for an hour. After adding methanol (520 g.) to the resultant mixture, the mixture was stirred at −20° C. for 1.5 hours. The precipitates were collected by filtration, washed with dichloromethane (120 ml.) and diethyl ether (130 ml.) in turn, and then dried to give p-nitrobenzyl 7-amino-3-cephem-4-carboxylate (7.90 g.), m.p. 182° C. (dec.).

I.R. $\nu_{max}^{Nujol}$: Nujol/max: 1790, 1730, 1638, 1600 cm$^{-1}$.

N.M.R. $\delta_{ppm}$(DMSO-d$_6$): 3.78(2H, d, J=4 Hz), 5.27(2H, dd, J=5 Hz), 5.44(2H, s), 6.78(1H, t, J=4 Hz), 7.72(2H, d, J=9 Hz), 8.26(2H, d, J=9 Hz).

(2) Vilsmeier reagent prepared from dimethylformamide (0.43 g.) and phosphorus oxychloride (0.92 g.) was suspended in dry ethyl acetate (10 ml.). To the suspension was added 2-(2-formamido-4-thiazolyl)-2-methoxyimino acetic acid (syn isomer, 1.15 g.) under ice-cooling with stirring, and the mixture was stirred at the same temperature for 30 minutes to prepare the activated acid solution. On the other hand, p-nitrobenzyl 7-amino-3-cephem-4-carboxylate hydrochloride (1.79 g.) and trimethylsilylacetamide (5.0 g.) were dissolved in ethyl acetate (40 ml.). To the solution was added the activated acid solution at −20° C. all at once, and the mixture was stirred at the same temperature for 2.5 hours. Water (60 ml.) and ethyl acetate (200 ml.) were added to the resultant solution, and the ethyl acetate layer was separated, washed with 10% hydrochloric acid (60 ml.), a saturated aqueous solution of sodium bicarbonate (60 ml.) and an aqueous solution of sodium chloride (50 ml.) in turn, dried over magnesium sulfate, treated with activated charcoal, and then evaporated under reduced pressure. Diethyl ether was added to the residue, and the precipitates were collected by filtration to give p-nitrobenzyl 7-{2-(2-formamido-4-thiazolyl)-2-methoxyimino-acetamido}-3-cephem-4-carboxylate (syn isomer, 1.30 g.), m.p. 210° to 212° C. (dec.).

I.R. $\nu_{max}^{Nujol}$: 3240, 1780, 1730, 1690, 1655 1605, 1550, 1520 cm$^{-1}$.

N.M.R. $\delta_{ppm}$DMSO-d$_6$): 3.65(2H, broad s), 3.90(3H, s), 5.20(1H, d, J=5 Hz), 5.43(2H, s), 5.95(1H, q, J=5,8 Hz), 6.68 (1H, t, J=4 Hz), 7.42 (1H, s), 7.72 (2H, d, J=9 Hz), 8.28 (2H, d, J=9 Hz), 8.46 (1H, s), 9.72 (1H, d, J=8 Hz).

(3) To a solution of p-nitrobenzyl 7-{2-(2-formamido-4-thiazolyl)-2-methoxyiminoacetamido}-3-cephem-4-carboxylate (syn isomer, 1.25 g.) in methanol (40 ml.) and tetrahydrofuran (50 ml.) was added 10% palladium carbon (0.65 g.), and the mixture was subjected to catalytic reduction at room temperature under atmospheric pressure for 3.5 hours. After removing the catalyst from the reaction mixture, the filtrate was concentrated under reduced pressure. Water (80 ml.) was added to the residue, and the mixture was adjusted to pH 7.5 with an aqueous solution of sodium bicarbonate, and then the insoluble substance was filtered off. The filtrate was washed with ethyl acetate (50 ml.), and then ethyl acetate (100 ml.) was added to the solution. After adjusting to pH 1.5 with 10% hydrochloric acid, the ethyl acetate layer was separated. The remaining aqueous layer was extracted with ethyl acetate (80 ml.) twice, and the extracts were combined with the ethyl acetate layer obtained above, washed with an aqueous solution of sodium chloride, dried over magnesium sulfate, and then concentrated under reduced pressure to give 7-{2-(2-formamido-4-thiazolyl)-2-methoxyiminoacetamido}-3-cephem-4-carboxylic acid (syn isomer, 0.60 g.), m.p. 176° to 183° C. (dec).

I.R. $\nu_{max}^{Nujol}$: 3250, 1780, 1690, 1660, 1550 cm$^{-1}$.

N.M.R. $\delta_{ppm}$ (DMSO-d$_6$): 3.63 (2H, d, J=4 Hz), 3.93 (3H, s), 5.10 (1H, d, J=5 Hz), 5.90 (1H, q, J=5,8 Hz), 6.53 (1H, t, J=4 Hz), 7.47 (1H, s), 8.57 (1H, s), 9.70 (1H, d, J=8 Hz), 12.63 (1H, s).

(4) 7-{2-(2-Formamido-4-thiazolyl)-2-methoxyiminoacetamido}-3-cephem-4-carboxylic acid (syn isomer, 95 mg.) was suspended in methanol (4 ml.). To the suspension was added conc. hydrochloric acid (110 mg.) and the solution was stirred at room temperature for 4 hours. After distilling methanol under reduced pressure, the residue was dissolved in water (30 ml.) and the aqueous solution was washed with ethyl acetate (10 ml.) and dichloromethane (15 ml.) in turn. Nitrogen gas was introduced into the aqueous solution to exclude the remaining organic solvent, and the aqueous solution was lyophilized to give 7-{2-(2-amino-4-thiazolyl)-2-methoxyiminoacetamido)-3-cephem-4-carboxylic acid hydrochloride (syn isomer, 83 mg.), m.p. 180° to 190° C. (dec.)

I.R. $\nu_{max}^{Nujol}$: 3300, 1770, 1710, 1660, 1630 cm$^{-1}$.

N.M.R. $\delta_{ppm}$ (DMSO-d$_6$) : 3.64 (2H, broad s), 3.95 (3H, s), 5.14 (1H, d, J=5 Hz), 5.82 (1H, t, J=4 Hz), 6.95 (1H, s), 9.80 (1H, d, J=8 Hz).

(5) The solution of 7-{2-(2-formamido-4-thiazolyl)-2-methoxyiminoacetamido}-3-cephem-4-carboxylic acid (syn isomer 10.8 g.), conc. hydrochloric acid (11 g.) and methanol (350 ml.) was stirred at room temperature for 4 hours. After concentrating the resultant solution under reduced pressure, ethyl acetate was added to the residue. The solution was adjusted to pH 8.0 with a saturated aqueous solution of sodium bicarbonate and the aqueous layer was separated and washed with diethyl ether. After nitrogen gas was bubbled in the aqueous solution, the aqueous solution was adjusted to pH 4.0 with 10% hydrochloric acid. The precipitates were collected by filtration and washed with water to give 7-{2-(2-amino-4-thiazolyl)-2-methoxyiminoacetamido}-3-cephem-4-carboxylic acid (syn isomer, 8.2 g.), m.p.>290° C.

IR $\nu_{max}^{Nujol}$: 3470, 3280, 3200, 1780, 1695, 1655, 1622 cm$^{-1}$.

NMR $\delta$ ppm (DMSO-d$_6$) : 3.60 (2H, broad s), 3.84 (3H, s), 5.12 (1H, dd, J=5 Hz), 5.84 (1H, dd, J=5,8 Hz), 6.52 (1H, broad t) 6.76 (1H, s), 7.26 (2H, broad s), 9.65 (1H, d, J=8 Hz).

(6) Sodium bicarbonate (1.04 g.) was added to a solution of 7-[2-(2-amino-4-thiazolyl)-2-methoxyiminoacetamido]-3-cephem-4-carboxylic acid hydrochloride (syn isomer, 2.6 g.) in water (100 ml.) under ice-cooling and stirred at room temperature. The resultant solution was lyophilized to give sodium 7-[2-(2-amino-4-thiazolyl)-2-methoxyiminoacetamido]-3-cephem-4-carboxylate (syn isomer).

I.R. $\nu_{max}^{Nujol}$: 3100, 1760, 1650, 1590, 1530 cm$^{-1}$.

N.M.R. $\delta$(D$_2$O, ppm) 3.60 (2H, broad q), 4.00 (3H, s), 5.22 (1H, d), 5.88 (1H, d) 6.35 (1H, q), 7.03 (1H, s).

(7) The product obtained above was dissolved in dry N,N-dimethylformamide (20 ml.). To the solution was dropwise added a solution of iodomethyl N-hexanoate (1.33 g.) and dry N,N-dimethylformamide (5 ml.) at −40° C. over 5 minutes, and then stirred at the same temperature for 40 minutes and then under ice-cooling for 45 minutes. The resultant solution was added to a mixed solution of ethyl acetate (60 ml.) and water (125 ml.). The ethyl acetate layer was separated, washed with a saturated sodium bicarbonate aqueous solutions and a saturated sodium chloride aqueous solution in turn dried over magnesium sulfate, and then treated with an activated charcoal. After removing ethyl acetate from the solution, the residue was triturated with diethyl ether to give N-hexanoyloxymethyl 7-[2-(2-amino-4-thiazolyl)-2-methoxyiminoacetamido]-3-cephem-4-carboxylate (syn isomer, 750 mg.).

I.R. $\nu_{max}^{Nujol}$: 3170, 1780, 1750 (shoulder), 1670, 1630, 1530 cm$^{-1}$.

N.M.R. $\delta$(CDCl$_3$, ppm) 0.68–1.84 (9H, m), 2.20–2.48 (2H, t), 3.20–3.80 (2H, m), 4.02 (3H, 2), 5.04 (1H, d), 5.60–6.20 (3H, m), 6.62 (1H, q), 6.80 (1H, s), 7.72 (1H, d).

(8) p-Nitrobenzyl 7-[2-(2-formamido-4-thiazolyl)-2-methoxyiminoacetamido]-3-cephem-4-carboxylate (syn-isomer: 1.1 g.) was suspended in a mixture of ethanol (10 ml.) and water (15 ml.) 1N Aqueous solution of potassium hydroxide (6 ml.) was added dropwise to the suspension at 5° to 7° C. over 10 minutes and stirred for 10 minutes. The resultant solution was adjusted to pH 7.5 with 10% hydrochloric acid, washed with ethyl acetate and adjusted to pH 2.5 with 10% hydrochloric acid. The precipitating crystals were collected by filtration to give the mixture of 7-[2-(2-formamido-4-thiazolyl)-2-methoxyiminoacetamido]-3-cephem-4-carboxylic acid (syn-isomer : 0.32 g.) and 7-{2-(2-amino-4-thiazolyl)-2-methoxyimino}-3-cephem-4-carboxylic acid (syn-isomer: 0.035 g.)

(9) 7-[2-(2-Amino-4-thiazolyl)-2-methoxyiminoacetamido]-3-cephem-4-carboxylic acid(syn-isomer: 5 g.) was gradually added to an aqueous solution (30 ml.) of sodium bicarbonate (1.04 g.) at 35° to 40° C., and stirred at 50° to 53° C. for 30 minutes. After removing the insoluble substance from the resultant solution, the filtrate was treated with activated charcoal (0.3 g.), and filtered. The filtrate was lyophilized to give sodium 7-[2-(2-amino-4-thiazolyl)-2-methoxyiminoacetamido]-3-cephem-4-carboxylate (syn-isomer: 4.2 g.).

I.R. $\delta_{max}^{Nujol}$: 3300–3100, 1760, 1670, 1595, 1530 cm$^{-1}$.

N.M.R. δppm (DMSO-d$_6$): 3.50 (2H, broad s), 3.83 (3H, s), 5.00 (1H, d, J=5 Hz), 5.68 (1H, dd, J=5 Hz, 8 Hz), 6.13 (1H, broad s), 6.73 (1H, s), 7.3 (2H, broad s), 9.60 (1H, d, J=8 Hz).

(10) 7-[2-(2-Aminothiazol-4-yl)-2-methoxyiminoacetamido]-3-cephem-4-carboxylic acid (syn isomer, 1.15 g.) was added to an aqueous solution of calcium hydroxide (0.111 g.) in water (100 ml.), and the solution was stirred at room temperature for 10 minutes. After the solution was filtered, the filtrate was lyophilized to give calcium 7-[2-(2-aminothiazol-4-yl)-2-methoxyiminoacetamido]-3-cephem-4-carboxylate (syn isomer, 1.2 g.).

I.R. $\nu_{max}^{Nujol}$: 3350, 1760, 1670, 1590, 1535, 1465 cm$^{-1}$.

N.M.R. δ(D$_2$O, ppm): 3.51 (1H, d, J=5 Hz), 3.59 (1H, d, J=3 Hz), 3.97 (3H, s), 5.15 (1H, d, J=5 Hz), 5.82 (1H, d, J=5 Hz), 6.33 (1H, dd, J=5 Hz, 3 Hz), 6.95 (1H, s).

(11) 7-[2-(2-Aminothiazol-4-yl)-2-methoxyiminoacetamido]-3-cephem-4-carboxylic acid (syn isomer, 1.15 g.) was added to a suspension of magnesium hydroxide (0.088 g.) in water (100 ml.), and the mixture was stirred at 70° C. for 30 minutes to give a solution. After the resultant solution was filtered, the filtrate was lyophilized to give magnesium 7-[2-(2-aminothiazol-4-yl)-2-methoxyiminoacetamido]-3-cephem-4-carboxylate (syn isomer, 1.1 g.).

I.R. $\nu_{max}^{Nujol}$: 3350, 1760, 1660, 1610, 1530, 1460 cm$^{-1}$.

N.M.R. δ(D$_2$O, ppm): 3.53 (1H, d, J=5 Hz), 3.59 (1H, d, J=3 Hz), 3.96 (3H, s), 5.16 (1H, d, J=5 Hz), 5.84 (1H, d, J=5 Hz), 6.32 (1H, dd, J=5 Hz, 3 Hz), 7.98 (1H, s).

(12) 7-[2-(2-Aminothiazol-4-yl)-2-methoxyiminoacetamido]-3-cephem-4-carboxylic acid (syn isomer, 1.15 g.) was added to a solution of arginine (0.523 g.) in water (50 ml.), and the solution was stirred at room temperature for 10 minutes. After the resultant mixture was filtered, the filtrate was lyophilized to give an arginine salt of 7-[2-(2-aminothiazol-4-yl)-2-methoxyiminoacetamido]-3-cephem-4-carboxylic acid (syn isomer, 1.35 g.).

I.R. $\nu_{max}^{Nujol}$: 3350, 3150, 1770, 1650 (broad), 1580, 1530, 1460 cm$^{-1}$.

N.M.R. δ(D$_2$O, ppm): 1.4–2.1 (4H, m), 3.22 (2H, t, J=6 Hz), 3.55 (1H, d, J=6 Hz), 3.65 (1H, d, J=3 Hz), 3.82 (1H, d, J=6 Hz), 3.97 (3H, s), 5.18 (1H, d, J=5 Hz), 5.85 (1H, d, J=5 Hz), 6.33 (1H, dd, J=6 Hz; 3 Hz), 7.00 (1H, s).

(13) Sodium 7-[2-(2-aminothiazol-4-yl)-2-methoxyiminoacetamido]-3-cephem-4-carboxylate (syn isomer, 1.21 g.) was added to a solution of lysine hydrochloride (0.55 g.) in water (12 ml.). The solution was lyophilized to give a lysine salt of 7-[2-(2-aminothiazol-4-yl)-2-methoxyiminoacetamido]-3-cephem-4-carboxylic acid (syn isomer, 1.6 g.).

I.R. $\nu_{max}^{Nujol}$: 3350, 3150, 1770, 1600(broad), 1530, 1460 cm$^{-1}$.

N.M.R. δ(D$_2$O, ppm): 1.3–2.1 (6H, m), 3.03 (2H, t, J=7Hz), 3.54 (1H, d, J=5Hz), 3.64 (1H, d, J=3Hz), 3.80 (1H, d, J=6Hz), 3.97 (3H, s), 5.17 (1H, d, J=5Hz), 5.84 (1H, d, J=5Hz), 6.32 (1H, dd, J=5Hz, 3Hz), 6.99 (1H, s).

(14) 20% Aqueous solution of sodium hydroxide was added to a suspension of 7-[2-(2-aminothiazol-4-yl)-2-methoxyiminoaceptamido]-3-cephem-4-carboxylic acid (syn isomer, 15 g.) in a mixture of ethanol (8 ml.) and water (8 ml.) at room temperature to make a solution of pH 7.5. After filtration and washing, the filtrate and washings were combined (which contained 18.3 ml. of water) and added dropwise ethanol (46 ml.) at 20° to 25° C. under stirring and stirred at the same temperature for 30 minutes. Ethanol (28 ml.) was added dropwise to the mixture over 30 minutes, and stirred at the same temperature for 2 hours. The precipitates were collected by filtration, washed with ethanol (20 ml.) and dried in vacuo at room temperature to give plates of sodium 7[2-(2-aminothiazol-4-yl)-2-methoxyiminoacetamido]-3-cephem-4-carboxylate dihydrate (syn isomer, 13.5 g.), mp 260° C. (dec.).

I.R. $\nu_{max}^{Nujol}$: 3430, 3250, 1760 (shoulder), 1745, 1650, 1630 (shoulder), 1590, 1540 cm$^{-1}$.

(15) Sodium 7-[2-(2-aminothiazol-4-yl)-2-methoxyiminoacetamido]-3-cephem-4-carboxylate (syn isomer, 15 g.) was dissolved in water (13 ml.) at 35° to 45° C. under stirring. Warmed ethanol (52 ml., 30° C.) was added dropwise to the stirred solution, and stirred at the same temperature for 5 minutes and then at room temperature for 2 hours. The precipitates were collected by filtration, washed with ethanol and dried under reduced pressure to give plates of sodium 7-[2-(2-aminothiazol-4-yl)-2-methoxyiminoacetamido]-3-cephem-4-carboxylate dihydrate (syn isomer, 13.45 g.).

(16) 4N Aqueous solution of sodium hydroxide was carefully added dropwise to a stirred suspension of 7-[2-(2-aminothiazol-4-yl)-2-methoxyiminoacetamido]-3-cephem-4-carboxylic acid (syn isomer, 52 g.) in water (100 ml.) below 5° C. to make a solution of pH 7.0 to 7.5. After filtration and washing, the combined filtrate and the washings (200 ml.) was added dropwise to ethanol (2 l.) under stirring over 30 minutes, and stirred at room temperature for 15 minutes and then at 5° to 10° C. for an hour. The precipitates were collected by filtration, washed with ethanol (200 ml.) and dried in vacuo at 30° C. to give amorphous sodium 7-[2-(2-aminothiazol-4-yl)-2-methoxyiminoacetamido]-3-cephem-4-carboxylate (syn isomer, 46.3 g.).

I.R. $\nu_{max}^{Nujol}$: 3400, 3300, 3170, 1750, 1650, 1580 cm$^{-1}$.

(17) A suspension of sodium 7-[2-(2-aminothiazol-4-yl)-2-methoxyiminoacetamido]-3-cephem-4-carboxylate (syn isomer, 10 g.) in methanol (250 ml.) was treated with a supersonic apparatus to make a clear solution. The solution was allowed to stand at room temperature, and then stirred at the same temperature for 3 hours. The precipitates were collected by filtration and washed with methanol to give amorphous sodium 7-[2-(2-aminothiazol-4-yl)-2-methoxyiminoacetamido]-3-cephem-4-carboxylate (syn isomer)

(18) The crystals obtained in the above Example were dried over P$_2$O$_5$ in vacuo for one day at room temperature to give another plates of sodium 7-[2-(2-aminothiazol)-2-methoxyiminoacetamido]-3-cephem-4-carboxylate (syn isomer).

EXAMPLE 5

(1) Vilsmeier reagent prepared from dimethylformamide (0.22 g.) and phosphorus oxychloride (0.46 g.) was suspended in dry ethyl acetate (20 ml.). 2-(2-Formamido-4-thiazolyl)-2-methoxyiminoacetic acid (anti isomer, 0.62 g.) was added to the suspension undericecooling with stirring, and the mixture was stirred at the same temperature for 30 minutes to prepare the activated acid solution. The solution was added all at once to a solution of p-nitrobenzyl 7-amino-3-chloro-3-cephem-4-carboxylate (1 g.) and trimethylsilylacetamide (2.58 g.) in ethyl acetate (20 ml.) at −20° C. with stirring, and the mixed solution was stirred at −10° to −20° C. for 1.5 hours. To the resultant solution was added water (20 ml.), and the solution was stirred at −20° C. After separating the ethyl acetate layer, the aqueous layer was extracted with ethyl acetate (20 ml.). The ethyl acetate layer and the extract were combined together, washed with 10% hydrochloric acid (20 ml.) twice, water (20 ml.) once, a 5% aqueous solution of sodium bicarbonate (20 ml.) three times, and an aqueous solution of sodium chloride (20 ml.) once in turn, dried, and then concentrated under reduced pressure. The residue was washed with diethyl ether (50 ml.) to give p-nitrobenzyl 7-{2-(2-formamido-4-thiazolyl)-2-methoxyiminoacetamido}-3-chloro-3-cephem-4-carboxylate (anti isomer, 1.27 g.), m.p. 135° to 145° C. (dec.).

I.R. $\nu_{max}^{Nujol}$: 3150 to 3300 (braod), 1780, 1730, 1670 to 1690 (broad) cm$^{-1}$.

N.M.R. $\delta_{ppm}$ (DMSO-d$_6$): 3.83 (2H, AB-q, J=17Hz), 3.97 (3H, s), 5.23 (1H, d, J=5Hz), 5.41 (2H, s), 5.9 (1H, dd J=5,8Hz), 7.62 (2H, d, J=8Hz), 8.0 (1H, s) 8.2 (2H, d, J=8Hz), 8.42 (1H, s), 9.55 (1H, d, J=8Hz), 12.43 (1H, s).

(2) 10% Palladium carbon (0.6 g.) was added to a solution of p-nitrobenzyl 7-{2-(2-formamido-4-thiazolyl)-2-methoxyiminoacetamido}-3-chloro-3-cephem-4-carboxylate (anti isomer, 1.16 g.) in methanol (20 ml.) and tetrahydrofuran (40 ml.), and the mixture was subjected to catalytic reduction at room temperature under atmospheric pressure for 5 hours. After removing the catalyst from the reaction mixture, the filtrate was concentrated under reduced pressure. Water (30 ml.) and ethyl acetate (60 ml.) were added to the residue, and the mixture was adjusted to pH 7.5 with an aqueous solution of sodium bicarbonate and shaked sufficiently. The aqueousl layer was separated and ethyl acetate (90 ml.) was added to the aqueous solution. The aqueous layer was adjusted to pH 2.5 with 10% hydrochloric acid with stirring under ice-cooling, and the ethyl acetate layer was separated. The remaining aqueous layer was extracted with ethyl acetate (30 ml.), and the extract and the ethyl acetate layer were combined together, washed with an aqueous solution of sodium chloride, dried and then concentrated under reduced pressure. The residue was washed with diisopropyl either to give 7-{2-(2-formamido-4-thiazolyl)-2-methoxyiminoacetamido}-3-chloro-3-cephem-4-carboxylic acid (anti isomer, 0.47 g.). The compound was colored at 210° C. and decomposed at above than 250° C.

I.R. $\nu_{max}^{Nujol}$: 3250, 1780, 1720 (shoulder), 1670 to 1690 cm$^{-1}$.

N.M.R. $\delta_{ppm}$ (DMSO-d$_6$): 3.8 (2H, AB-q, J=17Hz), 4.0 (3H, s), 5.21 (1H, d, J=5Hz), 5.83 (1H, dd, J=5,8Hz), 8.05 (1H, s), 8.47 (1H, s), 9.55 (1H, d, J=8Hz), 12.55 (1H, broad s).

(3) 7-{2-(2-Formamido-4-thiazolyl)-2-methoxyiminoacetamido}-3-chloro-3-cephem-4-carboxylic acid (anti isomer, 0.4 g.) was suspended in methanol (15 ml.). Conc. hydrochloric acid (0.16 g.) was added to the suspension and the mixture was stirred at room temperature for 5 hours. The precipitates were collected by filtration, washed with a mixed solvent of methanol and diethyl ether (1:1), and dried to give 7-{2-(2-amino-4-thiazolyl)-2-methoxyiminoacetamido}-3-chloro-3-cephem-4-carboxylic acid hydrochloride (anti isomer, 0.31 g.), m.p. above than 250° C.

I.R. $\nu_{max}^{Nujol}$: 3250, 3200, 1788, 1720, 1680, 1640 cm$^{-1}$.

N.M.R. $\delta_{ppm}$ (DMSO-d$_6$) : 3.81 (2H, AB-q, J=17Hz), 4.08 (3H, s), 5.22 (1H, d, J=5Hz), 5.7 (1H, dd, J=5,8 Hz), 7.59 (1H, s), 9.5 (1H, d, J=8Hz).

EXAMPLE 6

(1) A solution of Vilsmeier reagent was prepared from dry dimethylformamide (0.39 g.), dry ethyl acetate (1.2 ml.) and phosphorus oxychloride (0.84 g.) in a usual manner. To the solution was added a solution of 2-(1,2,3-thiadiazol-4-yl)-2-methoxyiminoacetic acid (syn isomer, 0.93 g.) in ethyl acetate (10 ml.) at −15° C. to prepare the activated acid solution. On the other hand, a p-nitrobenzyl 7-amino-3-cephem-4-carboxylate (1.5 g.), trimethylsilylacetamide (4.6 g.) and bis(trimethylsilyl)acetamide (1 ml.) in dry ethyl acetate (50 ml.) was stirred at 45° C. for 5 hours to give a solution. To the solution was added all at once the activated acid solution obtained above at −10° C. with stirring, and the mixed solution was stirred at −5° C. for 1.5 hours. Water as added to the reaction mixture, and the insoluble product was separated by filtration, washed with ethyl acetate and water in turn, and then dried to give pale yellow powder of p-nitrobenzyl 7-{2-(1,2,3-thiadiazol-4-yl)-2-methoxyiminoacetamido}-3-cephem-4-carboxylate (syn isomer, 1.9 g.), m.p. 243° to 245° C. (dec.).

I.R. $\nu_{max}^{Nujol}$: 3250, 1782, 1725, 1655, 1630, 1600, 1520, 1345 cm$^{-1}$.

N.M.R. $\delta_{ppm}$ (DMSO-d$_6$): 3.69 (2H, AB-q, J=14Hz), 4.00 (3H, s), 5.24 (1H, d, J=5Hz), 5.46 (2H, s), 6.00 (1H, dd, J=5,8Hz), 6.68 (1H, t, J=4Hz), 7.7 to 8.4 (4H, m), 9.44 (1H, s), 9.88 (1H, k, J=8Hz).

(2) 10% Palladium carbon (0.85 g.) was added to a solution of p-nitrobenzyl 7-{2-(1,2,3-thiadiazol-4-yl)-2-methoxyiminoacetamido}-3-cephem-4-carboxylate (syn isomer, 1.65 g.) in methanol (70 ml.) and tetrahydrofuran (90 ml.), and the mixture was subjected to catalytic reduction at room temperature under atmospheric pressure for 3.5 hours. After removing the catalyst from the reaction mixture by filtration, the filtrate was concentrated under reduced pressure. Water was added to the residue, and the mixture was adjusted to pH 7 to 8 with sodium bicarbonate, washed with ethyl acetate, adjusted to pH 1.5 with 10% hydrochloric acid, and then extracted with ethyl acetate. The extract was washed with a saturated aqueous solution of sodium chloride, dried over magnesium sulfate, and then filtered. The filtrate was concentrated under reduced pressure, and the residue was pulverized with diethyl ether. The precipitates were collected by filtration and the dried to give yellow powder of 7-{(2-(1,2,3-thiadiazol-4-yl)-2-methoxyiminoacetamido}-3-cephem-4-carboxylic acid (syn isomer, 0.3 g.), m.p. 200° to 210° C. (dec.).

I.R. $\nu_{max}^{Nujol}$: 3250, 2550 to 2600, 1785, 1715, 1655, 1630, 1600 cm$^{-1}$.

N.M.R. $\delta_{ppm}$ (DMSO-d$_6$): 3.58 (2H, AB-q, J=14Hz), 4.00 (3H, s), 5.15 (1H, d, J=5Hz), 5.90 (1H, dd, J=5,8Hz), 6.52 (1H, t, J=5Hz), 9.38 (1H, s), 9.84 (1H, d, J=8Hz).

EXAMPLE 7

7-Amino-3-cephem-4-carboxylic acid (1.7 g.) and sodium bicarbonate (2.84 g.) were dissolved in a mixture of water (35 ml.) and acetone (35 ml.). On the other hand, phosporus oxychloride (1.95 ml.) was added dropwise to a suspension of 2-(2-amino-4-thiazolyl)-2-methoxyiminoacetic acid (syn-isomer: 3.42 g.) in dry ethyl acetate (34 ml.) over 10 minutes at 0° to 6° C., and the mixture was stirred at the same temperature for 30 minutes. To the solution was added dropwise a solution of trimethylsilylacetamide (2.39 g.) in ethyl acetate (5ml.) at 0° to 6° C. over 20 minutes, and the mixture was stirred for 20 minutes. After phosphorus oxychloride (19.5 ml.) was added dropwise to the mixture at the above temperature over 10 minutes, the mixture obtained thus was stirred for 30 minutes. And further, dimethylformamide (1.29 ml.) was added dropwise to the mixture over 10 minutes at the same temperature and stirred for one hour to give a clear solution. The solution was added dropwise to the solution of 7-amino-3-cephem-4-carboxylic acid at −5° to 5° C., over 30 minutes, at pH 6.5 to 7.5, and the reaction mixture was stirred for one hour at the same temperature. Ethyl acetate (200 ml.) was added to the resultant solution, and the aqueous layer was separated, washed with methylene chloride, bubbled with nitrogen gas and adjusted to pH 4 with acetic acid. The solution was subjected to column chromatography on macroporous, non-ionic adsorption resin "Diaion HP-20" (Trade mark: manufactured by Mitsubishi Chemical Industries Ltd.) and eluted with 20% aqueous solution of isopropyl alcohol. The eluate was concentrated under reduced pressure and lyophilized to give 7-[2-(2-amino-4-thiazolyl)-2-methoxyiminoacetamido]-3-cephem-4-carboxylic acid (syn-isomer: 2.0 g.) The product was identified with the authentic sample by IR and NMR spectrum.

EXAMPLE 8

(1) Phosphorus oxychloride (1.2 g.) was added all at once to a suspension of 2-(2-amino-4-thiazolyl)-2-methoxyiminoacetic acid (syn-isomer: 1.23 g.) in ethyl acetate (12 ml.) at 5° C. and stirred at 4° to 6° C. for 30 minutes. Trimethylsilylacetamide (1.0 g.) was added to the solution and stirred at 4° to 6° C. for 30 minutes. Phosphorus oxychloride (1.2 g.) was added again to the solution and stirred for 15 minutes. And further, dimethylformamide (0.5 g.) was added all at once to the solution at 4° to 6° C. and stirred for 40 minutes to give a clear solution. On the other hand, p-nitrobenzyl 7-amino-3-cephem-4-carboxylate hydrochloride (1.9 g.) was added to a mixture of tetrahydrofuran (30 ml.) and acetone (10 ml.), and an aqueous solution (20 ml.) of sodium bicarbonate (0.6 g.) was added to the mixture. To the solution was added dropwise the solution obtained above at 0° to 5° C., pH 8.0. After stirring the mixture at −2° to 2° C., at pH 8.0 for 30 minutes, the insoluble substance was filtered out. The filtrate was extracted with ethyl acetate, and the extract was washed with a saturated aqueous solution of sodium chloride, dried over magnesium sulfate and then concentrated under reduced pressure. The residue was pulverized with diisopropyl ether to give p-nitrobenzyl 7-[2-(2-amino-4-thiazolyl)-2-methoxyiminoacetamido]-3-cephem-4-carboxylate (syn-isomer: 1.6 g.).

I.R. $\delta_{max}^{Nujol}$: 3300, 1780, 1730, 1670, 1520 cm$^{-1}$.

N.M.R. δppm (DMSO-d$_6$) : 3.60 (2H, m), 3.81 (3H, s), 5.12 (1H, d, J=5Hz), 5.85 (1H, dd, J=5Hz, 10Hz), 6.64 (1H, m), 6.70 (1H, s), 7.20 (2H, s), 7.65 (2H, d, J=10Hz), 8.19 (2H, d, J=10Hz), 9.60 (1H, d, J=10Hz).

(2) p-Nitrobenzyl 7-[2-(2-amino-4-thiazolyl)-2-methoxyiminoacetamido]-3-cephem-4-carboxylate (syn-isomer: 7.8 g.) was suspended in a mixture of ethanol (60 ml.) and water (60 ml.) 1N Aqueous solution of potassium hydroxide (45 ml.) was added dropwise to the stirred suspension under ice-cooling over 10 minutes and stirred at 5° C. for 15 minutes. The resultant solution was adjusted to pH 7.0 with conc. hydrochloric acid, washed with ethyl acetate and the concentrated under reduced pressure to half of its initial volume. The concentrated solution was adjusted to pH 5.0 and subjected to column chromatography on macroporous, non-ionic adsorption resin "Diaion HR-20" (Trade mark; manufactured by Mitsubishi Chemical Industries Ltd.; 80 ml.) and eluted with 5% aqueous solution of isopropyl alcohol. The fractions containing the object compound were collected and adjusted to pH 3.2 with 10% hydrochloric acid. The precipitating crystals were collected by filtration, and dried to give 7-[2-(2-amino-4-thiazolyl)-2-methoxyiminoacetamido]-3-cephem-4-carboxylic acid (syn-isomer: 2.3 g.).

EXAMPLE 9 p-Nitrobenzyl 7-amino-3-cephem-4-carboxylate (3.4 g.) was suspended in tetrahydrofuran (60 ml.) and an aqueous solution (20 ml.) of sodium bicarbonate (1.2 g.) was added to the suspension. 1N Aqueous sodium hydroxide (30 ml.) was added dropwise to the solution at 3° to 4° C. and stirred for 20 minutes. The resultant solution was adjusted to pH 7.0 with 10% hydrochloric acid and concentrated under reduced pressure. The insoluble substance was filtered out and the filtrate was washed with ethyl acetate. Acetone (30 ml.) was added to the filtrate and cooled to −5° C. A solution prepared from phosphorus oxychloride, dimethylformamide, trimethylsilylacetamide and 2-(2-amino-4-thiazolyl)-2-methoxyiminoacetic acid (syn-isomer: 2.2 g.) in a similar manner to Example 7 was added to the solution obtained above at −5° to 0° C., at pH 7.5 to 8.5. The mixture was stirred at 3° to 7° C., at pH 7.5 to 8.5 for 2 hours, and the insoluble substance was filtered out. The aqueous layer was separated from the filtrate, washed with ethyl acetate and adjusted to pH 3.0 to give 7-[2-(2amino-4-thiazolyl)-2-methoxyiminoacetamido]-3-cephem-4-carboxylic acid (syn-isomer: 1.1 g.).

EXAMPLE 10

(1) Phosphoryl chloride (1.764 g.) was added to a suspension of 2-(2-amino-4-thiazolyl)-2-ethoxyiminoacetic acid (syn isomer, 1.0 g.) in tetrahydrofuran (10 ml.) below 5° C. and stirred at the same temperature for 20 minutes. To the solution were added trimethylsilylacetamide (0.4 g.) and N,N-dimethylformamide (0.4 g.), and the solution was stirred below 5° C. for 40 minutes [Solution A]. On the other hand, trimethylsilylacetamide (3.5 g.) was added to a suspension of 4-nitrobenzyl 7-amino-3-cephem-4-carboxylate (1.5 g.) in tetrahydrofuran (15 ml.), and stirred at room temperature for 1.5 hours. To the solution was added all at once the above Solution A at −20° C., and the solution was stirred at −5° to 0° C. for an hour. Water (20 ml.) was added to the resultant solution at −20° C., and the solution was adjusted to pH 7.5 with an aqueous solution of sodium bicarbonate. Tetrahydrofuran (70 ml.) and a saturated aqueous solution of sodium chloride (50 ml.) were added to the solution, and the solution was shaken sufficiently. The aqueous layer was separated and extracted with tetrahydrofuran. The tetrahydrofuran layer and extract were combined and washed with a saturated aqueous solution of sodium chloride. The solution was dried over magnesium sulfate and concentrated under reduced pressure. The residue was triturated with diisopropyl ether to give 4-nitrobenzyl 7-[2-(2-amino-4-thiazolyl)-2-ethoxyiminoacetamido]-3-cephem-4-carboxylate (syn isomer, 2.5 g.).

I.R. $\nu_{max}^{Nujol}$: 3330, 1780, 1730, 1680, 1640, 1610 cm$^{-1}$. N.M.R. δppm (DMSO-d$_6$): 1.17 (3H, J=7Hz), 3.50 (2H, m), 4.05 (2H, q, J=7Hz), 5.10 (1H, d, J=5Hz), 5.85 (1H, dd, J=5Hz, 8Hz), 6.67 (1H, s), 7.17 (2H, m), 7.63 (2H, d, J=8Hz), 8.18 (2H, d, J=8Hz), 10.13 (1H, d, J=8Hz).

(2) Palladium on carbon (1.0 g.) moistened with water (8 ml.) was added to a solution of 4-nitrobenzyl 7-[2-(2-amino-4-thiozolyl)-2-ethoxyiminoacetamido]-3-cephem-4-carboxylate (syn isomer, 2.3 g.) in a mixture of tetrahydrofuran (30 ml.), methanol (15 ml.) and acetic acid (0.3 ml.), and the suspension was subjected to catalytic reduction at room temperature under ordinary pressure for 2 hours. After removing the catalyst from the resultant mixture by filtration, the filtrate was concentrated under reduced pressure. Ethyl acetate was added to the residue, and the solution was adjusted to pH 7.5 with an aqueous solution of sodium bicarbonate. After removing the insoluble substance by filtration, the aqueous solution was separated, washed with ethyl acetate, adjusted to pH 5.5 and then treated with activated charcoal. The aqueous solution was adjusted to pH 3.2, and the precipitates were collected by filtration and dried to give 7-[2-(2-amino-4-thiazolyl)-2-ethoxyiminoacetamido]-3-cephem-4-carboxylic acid (syn isomer, 0.6 g.).

I.R. $\nu_{max}^{Nujol}$: 3500, 3300, 3200, 1785, 1625, 1600 cm$^{-1}$.

N.M.R. δppm(DMSO-d$_6$): 1.20 (3H, t, J=7Hz), 3.57 (2H, m), 4.08 (2H, q, J=7Hz), 5.08 (1H, d, J=5Hz), 5.83 (1H, dd, J=5Hz, 8Hz), 6.47 (1H, m), 6.73 (1H, s), 7.20 (2H, m), 9.58 (1H, d, J=8Hz).

EXAMPLE 11

(1) Triethylamine (2.37 g.), dimethylaniline (7.12 g.) and trimethylsilyl chloride (3.93 g.) were added to a stirred suspension of 4-nitrobenzyl 7-(2-phenylacetamido)-3-hydroxy-3-3-cephem-4-carboxylate (10 g.) in methylene chloride (200 ml.) in turn, and the solution was stirred at room temperature for an hour. Phosphorus pentachloride (4.88 g.) was added to the solution at −30° to −25° C. and stirred at −25° to −20° C. for 3 hours. Methanol (42 ml.) was added to the solution at −25° to −20° C., and stirred for an hour. To the solution was added water (35 ml.) at −25 to −20° C., and the solution was stirred at room temperature. The precipitates were collected by filtration, washed with methylene chloride and diethyl ether in turn, and dried to give 4-nitrobenzyl 7-amino-3-hydroxy-3-cephem-4-carboxylate (5.2 g.), mp 148° C. (dec.).

I.R. $\nu_{max}^{Nujol}$: 3440, 3300, 1760, 1740 cm$^{-1}$.

N.M.R. δppm (DMSO-d$_6$): 2.8–3.7 (2H, m), 4.90 (1H, t, J=4Hz), 5.29 (1H, d, J=4Hz), 5.38 (2H, s), 7.71 (2H, d, J=8Hz), 8.26 (2H, d, J=8Hz). (2) Phosphoryl chloride (2.87 g.) was dropwise added to a solution of N,N-dimethylformamide (1.37 g.) in ethyl acetate (10 ml.) at 5° to 10° C. Ethyl acetate (40 ml.) was added to the solution, and stirred under ice cooling for 40 minutes. To the solution was added 2-(2-formamido-4-thiazolyl)-2-methoxyiminoacetic acid (syn isomer, 3.58 g.), and the solution was stirred at 0° to 5° C. for 40 minutes. The resultant solution was added all at once to a mixture of 4-nitrobenzyl 7-amino-3-hydroxy-3-cephem-4-carboxylate (5 g.), ethyl acetate (50 ml.), trimethylsilylacetamide (14.3 g.) and bis(trimethylsilyl)acetamide (5.8 g.) at −15° C., and stirred at −20° to −15° C. for 1.2 hours. Water (50 ml.) was added to the resultant solution at −25° to −20° C., and stirred until the temperature rise 5° C. The aqueous layer was separated and extracted with ethyl acetate. The ethyl acetate layer and extract were combined, washed with a saturated aqueous solution of sodium chloride and dried over magnesium sulfate. After the solution was concentrated to a volume of 50 ml. under reduced pressure, the precipitates were collected by filtration and washed with ethyl acetate to give 4-nitrobenzyl 7-[2-(2-formamido-4-thiazolyl)-2-methyoxyiminoacetamido]-3-hydroxy-3-cephem-4-carboxylate (syn isomer, 3.5 g.), mp 163° C. (dec.).

I.R. $\nu_{max}^{Nujol}$: 3210, 3160, 3050, 1780, 1665 cm$^{-1}$.

N.M.R. δppm (DMSO-d$_6$): 3.0–4.2 (2H, m), 3.95 (3H, s), 5.28 (1H, d, J=4Hz), 5.41 (2H, s), 5.64 (1H, dd, J=4Hz, 9Hz), 7.49 (1H, s) 7.67 (2H, d, J=8Hz), 8.21 (2H, d, J=8Hz), 8.50 (1H, t, J=9Hz).

(3) A solution of the compound obtained above (1 g.) in methanol (15 ml.), tetrahyrofuran (5 ml.) and conc. hydrochloric acid (0.72 g.) was stirred at room temperature for an hour. Diethyl ether (100 ml.) was added to the resultant solution and then triturated. The crystals were collected by filtration to give 4-nitrobenzyl 7-[2-(2-aminothiazol-4-yl)-2-methoxyiminoacetamido]-3-hydroxy-3-cephem-4-carboxylate hydrochloride (syn isomer, 0.65 g.).

I.R. $\nu_{max}^{Nujol}$: 3180, 1780, 1680, 1670, 1640 cm$^{-1}$.

N.M.R. δppm (DMSO-d$_6$): 3.2–4.0 (2H, m), 3.97 (3H, s), 5.27 (1H, d, J=4Hz), 5.41 (2H, s), 5.60 (1H, dd, J=4Hz, 8Hz), 7.10 (1H, s), 7.66 (2H, d, J=9Hz), 8.25 (2H, d, J=9Hz), 9.73 (1H, d, J=8Hz).

EXAMPLE 12

(1) Phosphoryl chloride (1.76 g.) and trimethylsilylacetamide (0.4 g.) were added to a stirred suspension of 2-(2-amino-4-thiazolyl)-2-ethoxyiminoacetic acid (syn isomer, 1.0 g) in tetrahydrofuran (10. ml.) below 5° C., and stirred at the same temperature for 30 minutes. N,N-Dimethylformamide (0.4 g.) was added to the solution and stirred below 5° C. for 20 minutes [Solution A]. Trimethylsilylacetamide (4.8 g.) was added to a stirred suspension of 4-nitrobenzyl 7-amino-3-chloro-3-cephem-4-carboxylate hydrochloride (1.9 g.) in tetrahydrofuran (15 ml.), and the solution was stirred at room temperature for an hour. To the solution was added the above Solution A all at once at −20° C., and the solution was stirred at 0° C. for an hour. Water (50 ml.) was added to the resultant solution at −20° C., and adjusted to pH 8.0 with an aqueous solution of sodium bicarbonate. Tetrahydrofuran (50 ml.) and a saturated aqueous solution of sodium chloride (50 ml.) were added to the solution. The organic layer was separated, washed with a saturated aqueous solution of sodium chloride and dried over magnesium sulfate. After concentrating the solution under reduced pressure, the residue was triturated with diisopropyl ether and the precipitates were collected by filtration to give 4-nitrobenzyl 7-[2-(2-amino-4-thiazolyl)-2-ethoxyiminoacetamido]-3-chloro-3-cephem-4-carboxylate (syn isomer, 2.0 g.).

I.R. $\nu_{max}^{Nujol}$: 3200, 1780, 1730, 1670 cm$^{-1}$.

N.M.R. δppm (DMSO-d$_6$): 1.23 (3H, t, J=7Hz), 3.96 (2H, s), 4.13 (2H, q, J=7Hz), 5.31 (1H, d, J=5Hz), 5.88 (1H, dd, J=5Hz, 8Hz), 6.77 (1H, s), 7.67 (2H, d, J=8Hz), 8.25 (2H, d, J=8Hz), 10.30 (1H, d, J=8Hz).

(2) A suspension of palladium on carbon (0.8 g.) in water (5 ml.) was added to a mixture of 4-nitrobenzyl 7-[2-(2-amino-4-thiazolyl)-2-ethoxyiminoacetamido]-3-chloro-3-cephem-4-carboxylate (syn isomer, 2.0 g.), acetic acid (0.6 ml.) and tetrahydrofuran (60 ml.), and the suspension was subjected to catalytic reduction under ordinary pressure at room temperature for 3 hours. After removing the catalyst by filtration, the filtrate was concentrated under reduced pressure. After adding ethyl acetate (50 ml.) to the residue, the solution was adjusted to pH 7.5 with an aqueous solution of sodium bicarbonate, and the insoluble substance was filtered out. The aqueous layer was separated and adjusted to pH 6.0 with 10% hydrochloric acid, and then the organic solvent was removed under reduced pressure. The aqueous solution was subjected to column chromatography on macroporous, nonionic adsorption resin "Diaion HP-20" (Trademark, manufactured by Mitsubishi Chemical Industries Ltd.) (30 ml.). The column was washed with water and eluted with 5% aqueous isopropyl alcohol. The eluate was lyophilized to give sodium 7-[2-(2-amino-4-thiazolyl)-2-ethoxyiminoacetamido]-3-chloro-3-cephem-4-carboxylate (syn isomer, 0.3 g.).

I.R. $\nu_{max}^{Nujol}$: 3350, 3200, 1770, 1675, 1620 cm$^{-1}$.

N.M.R. δppm (D$_2$O): 1.33 (3H, t, J=7Hz), 3.76 (2H, q, J=18Hz), 4.30 (2H, q, J=7Hz), 5.33 (1H, d, J=5Hz), 5.83 (1H, d, J=5Hz), 7.06 (1H, s).

EXAMPLE 13

(1) Phosphoryl chloride (4.6 g.), trimethylsilylacetamide (0.95 g.) and N,N-dimethylformamide (1.2 g.) were added to a stirred suspension of 2-(2-amino-4-thiazolyl)-2-isopropoxyiminoacetic acid (syn isomer, 2.8 g.) in tetrahydrofuran (25 ml.) below 5° C. for 30 minutes [Solution A]. On the other hand, trimethylsilylacetamide (10.5 g.) was added to a suspension of 4-nitrobenzyl 7-amino-3-cephem-4-carboxylate (3.9 g.) in tetrahydrofuran (50 ml.), and stirred at room temperature for 1.5 hours. To the solution was added the above solution A at −20° C. all at once, and the solution was stirred at −5° to 0° C. for 40 minutes. Water (70 ml.) and tetrahydrofuran (100 ml.) were added to the resultant solution at −20° C. The solution was adjusted to pH 7.5 with an aqueous solution of sodium bicarbonate and stirred for an hour. After a saturated aqueous solution of sodium chloride (200 ml.) was added, the organic layer was separated. The remaining aqueous layer was extracted with tetrahydrofuran, and the extract and the above organic layer were combined, washed with a saturated aqueous solution of sodium chloride, dried over magnesium sulfate and then concentrated under reduced pressure. The residue was triturated with diisopropyl ether and the precipitates were collected by filtration to give 4-nitrobenzyl 7-[2-(2-amino-4-thiazolyl)-2-isopropoxyiminoacetamido]-3-cephem-4-carboxylate (syn isomer, 6.0 g.).

I.R. $\nu_{max}^{Nujol}$: 3320, 3270, 1775, 1730, 1670, 1630 cm$^{-1}$.

N.M.R. δppm (DMSO-d$_6$): 1.17 (6H, d, J=6Hz), 3.63 (2H, m), 4.33 (1H, q, J=6Hz), 5.17 (1H, d, J=5Hz), 5.42 (2H, s), 5.92 (1H, dd, J=5Hz, 8Hz), 6.67 (1H, m), 6.70 (1H, s), 7.22 (2H, m), 7.70 (2H, d, J=8Hz), 8.25 (2H, d, J=8Hz), 10.13 (1H, d, J=8Hz).

(2) Acetic acid (1ml.) and a suspension of 10% palladium on carbon (2.0 g.) in water (8 ml) were added to a solution of 4-nitrobenzyl 7-[2-(2-amino-4-thiazolyl)-2-isopropoxyiminoacetamido]-3-cephem-4-carboxylate (syn isomer, 5.0 g.) in tetrahydrofuran (150 ml.), and the suspension was subjected to catalytic reduction at room temperature under ordinary pressure. After removing the catalyst by filtration, the filtrate was concentrated under reduced pressure. Ethylacetate (80 ml.) was added to the residue, and adjusted to pH 7.5 with an aqueous solution of sodium bicarbonate. The organic layer was separated and extracted with an aqueous solution of sodium bicarbonate. The extract and the aqueous layer obtained above were combined, adjusted to pH 3.0 with conc. hydrochloric acid and extracted with tetrahydrofuran. The extract was washed with a saturated aqueous solution of sodium chloride, dried over magnesium sulfate and concentrated under reduced pressure.

The precipitating crystals were collected by filtration and dried to give 7-[2-(2-amino-4-thiazolyl)-2-isopropoxyiminoacetamido]-3-cephem-4-carboxylic acid (syn isomer, 0.8 g.).

I.R. $\nu_{max}^{Nujol}$: 3320, 1780, 1670, 1635 cm$^{-1}$.

N.M.R. δppm (DMSO-d$_6$): 1.20 (6H, d, J=6Hz), 3.55 (2H, m), 4.30 (1H, q, J=6Hz), 5.08 (1H, d, J=5Hz), 5.82 (1H, dd, J=5Hz, 8Hz), 6.45 (1H, m), 6.68 (1H, s), 7.10 (2H, m), 10.08 (1H, d, J=8Hz).

EXAMPLE 14

(1) Phosphoryl chloride (4.6 g.), trimethylsilylacetamide (0.95 g.) and N,N-dimethylformamide (1.2 g.) were added to a stirred suspension of 2-(2-amino-4-thiazolyl)-2-propoxyiminoacetic acid (syn isomer, 2.8 g.) in tetrahydrofuran (25 ml.) below 5° C., and stirred for 20 minutes. The solution was dropwise added to a suspension of 4-nitrobenzyl 7-amino-3-cephem-4-carboxylate (3.9 g.) in a mixture of tetrahydrofuran (20 ml.), water (20 ml.) and acetone (20 ml.) at −5° to 5° C. while keeping the pH value at 6.9 to 7.1 with 20% aqueous solution of sodium carbonate. The solution was stirred at −5° to 5° C. for 30 minutes and further at 10° C. for an hour, and adjusted to pH 7.5. After tetrahydrofuran (100 ml.) and a saturated aqueous solution of sodium chloride (200 ml.) were added to the resultant solution, the insoluble substance was filtered out. The organic layer was separated from the filtrate, washed with a saturated aqueous solution of sodium chloride, dried over magnesium sulfate and then concentrated under reduced pressure. The residue was triturated with diisopropyl ether and the precipitates were collected by filtration to give 4-nitrobenzyl 7-[2-(2-amino-4-thiazolyl)-2-propoxyiminoacetamido]-3-cephem-4-carboxylate (syn isomer, 5.8 g.).

I.R. $\nu_{max}^{Nujol}$: 3300, 1780, 1730, 1670, 1640 cm$^{-1}$.

N.M.R. δppm (DMSO-d$_6$): 0.93 (3H, t, J=6Hz), 1.70 (2H, m), 3.70 (2H, m), 4.08 (2H, t, J=6Hz), 4.5 (2H, m), 5.23 (1H, d, J=5Hz), 5.50 (2H, s), 5.97 (1H, dd, J=5Hz, 8Hz), 6.73 (1H, m), 6.80 (1H, s), 7.75 (2H, d, J=9Hz), 8.30 (2H, d, J=9Hz), 9.65 (1H, d, J=8Hz).

(2) 4-Nitrobenzyl 7-[2-(2-amino-4-thiazolyl)-2-propoxyiminoacetamido]-3-cephem-4-carboxylate (syn isomer, 5.0 g.) was treated in a similar manner to that of Example 13 -(2) to give 7-[2-(2-amino-4-thiazolyl)-2-propoxyiminoacetamido]-3-cephem-4-carboxylic acid (syn isomer, 0.9 g.)

I.R. $\nu_{max}^{Nujol}$: 3250, 1770, 1650, 1660, 1620 cm$^{-1}$.

N.M.R. δppm (DMSO-d$_6$): 0.93 (3H, t, J=7Hz), 1.67 (2H, sextet, J=7Hz), 3.60 (2H, m), 4.03 (2H, t, J=7Hz), 5.13 (1H, d, J=5Hz), 5.83 (1H, dd, J=5Hz, 8Hz), 6.48 (2H, t, J=4Hz), 6.70 (1H, s), 7.18 (2H, m), 9.53 (1H, d, J=8Hz).

EXAMPLE 15

(1) Phosphoryl chloride (13.2 g.) was added dropwise to a stirred solution of N,N-dimethylformamide (6.3 g.) and tetrahydrofuran (24.7 ml.) at −5° C., and stirred at the same temperature for 30 minutes. Tetrahydrofuran (120 ml.) and 2-(2-formamidothiazol-4-yl)-2-n-butoxyiminoacetic acid (syn isomer, 19.5 g.) were added to the solution at −5° C., and stirred at the same temperature for 30 minutes. The solution was added dropwise a stirred suspension of 4-nitrobenzyl 7-amino-3-cephem-4-carboxylate (24.7 g.), tetrahydrofuran (120 ml.), acetone (60 ml.) and water (60 ml.) at −5° to 5° C. over 15 minutes while adjusting to pH 7 to 7.5 with 20% aqueous solution of sodium carbonate, and then the solution was stirred for 30 minutes. The insoluble substance was filtered off, and a saturated aqueous solution of sodium chloride was added to the filtrate. The solution was extracted with tetrahydrofuran twice. The extract was washed with a saturated aqueous solution of sodium chloride, dried over magnesium sulfate and concentrated in vacuo. The residue was triturated with diisopropyl ether to give 4-nitrobenzyl 7-[2-(2-formamidothiazol-4-yl)-2-n-butoxyiminoacetamido]-3-cephem-4-carboxylate (syn isomer, 34.6 g.).

I.R. $\nu_{max}^{Nujol}$: 3240, 3050, 1780, 1730, 1695, 1660 cm$^{-1}$.

N.M.R. δ(DMSO-d$_6$, ppm): 0.92 (3H, t, J=7 Hz), 0.8∼2.2 (4H, m), 3.67 (2H, d, J=4 Hz), 4.16 (2H, t, J=7 Hz), 5.23 (1H, d, J=5 Hz), 5.46 (2H, s), 5.99 (1H, dd, J=5 Hz, 8 Hz), 6.71 (1H, t, J=5 Hz), 7.43 (1H, s), 7.76 (2H, d, J=9 Hz), 8.30 (2H, d, J=9 Hz), 8.58 (1H, s), 9.72 (1 H, d, J=8 Hz), 12.66 (1H, s).

(2) A mixture of 4-nitrobenzyl 7[2-(2-formamidothiazol-4-yl)-2-n-butoxyiminoacetamido]-3-cephem-4-carboxylate (syn isomer, 34.5 g.), tetrahydrofuran (345 ml.), 10% palladium carbon (14 g.), methanol (140 ml.), acetic acid (2.5 ml.) and water (50 ml.) was subjected to catalytic reduction under ordinary pressure at room temperature for 3 hours. The resultant mixture was filtered, and washed with tetrahydrofuran. The filtrate was concentrated in vacuo, and the residue was dissolved in a mixture of ethyl acetate and an aqueous solution of sodium bicarbonate. The insoluble substance was removed by filtration. After the ethyl acetate layer was separated and extracted with an aqueous solution of sodium bicarbonate, the aqueous layer and the aqueous extract were combined. After the aqueous solution was washed with ethyl acetate and diethyl ether in turn, the solution was adjusted to pH 2.0 with 10% hydrochloric acid and stirred for 30 minutes. The precipitates were collected by filtration, washed with water and dried over magnesium sulfate to give 7-[2-(2-formamidothiazol-4-yl)-2-butoxyiminoacetamido]-3-cephem-4-carboxylic acid (syn isomer, 18.3 g.).

I.R. $\nu_{max}^{Nujol}$: 3330, 3040, 1780, 1725, 1695, 1655 cm$^{-1}$.

N.M.R. δ(DMSO-d$_6$, ppm): 0.90 (3H, t, J=7 Hz), 1.1∼1.9 (4H, m), 3.58 (2H, d, J=5 Hz), 4.12 (2H, t, J=7 Hz), 5.13 (1H, d, J=5 Hz), 5.86 (1H, dd, J=5 Hz, 8 Hz), 6.46 (1H, t, J=4 Hz), 7.40 (1H, s), 8.50 (1H, s), 9.63 (1H, d, J=8 Hz), 12.57 (1H, broad s).

(3) A mixture of 7-[2-(2-formamidothiazol-4-yl)-2-n-butoxyiminoacetamido]-3-cephem-4-carboxylic acid (syn isomer, 12.7 g.), conc. hydrochloric acid (9.6 ml.), methanol (9.5 ml.) and tetrahydrofuran (9.5 ml.) was stirred at room temperature for 3 hours. The resultant solution was concentrated in vacuo, and the residue was suspended in water. The suspension was adjusted to pH 3.5 with sodium bicarbonate under ice cooling, and stirred at same temperature for 30 minutes. The precipitates were collected by filtration and dried over magnesium sulfate to give the powder (10 g.). The powder was suspended in water (300 ml.) and adjusted to pH 7.0 with sodium bicarbonate. The solution was adjusted to pH 6.0 with 10% hydrochloric acid and subjected to column chromatography on nonionic adsorption resin (Diaion HP-20:trademark, manufactured by Mitsubishi Chemical Industries Ltd.) (300 ml.) with 10% aqueous solution of isopropyl alcohol. The eluate was adjusted to pH 3.5 with 10% hydrochloric acid under ice cooling, and the precipitates were collected by filtration, washed with water and dried to give 7-[2-(2-aminothiazol-4-yl)-2-n-butoxyiminoacetamido]-3-cephem-4-carboxylic acid (syn isomer, 7.2 g.).

I.R. $\nu_{max}^{Nujol}$: 3320, 1775, 1660 cm$^{-1}$.

N.M.R. δ(DMSO-d$_6$, ppm): 0.88 (3H, t, J=7 Hz), 1.1∼1.9 (4H, m), 3.58 (2H, broad s), 4.05 (2H, t, J=7 Hz), 5.08 (1H, d, J=5 Hz), 5.80 (1H, dd, J=5 Hz, 8 Hz), 6.44 (1H, broad s), 7.18 (2H, s), 9.51 (1H, d, J=8 Hz).

EXAMPLE 16

(1) 2-(2-Formamidothiazol-4-yl)-2-iso-butoxyiminoacetic acid (syn isomer, 6.48 g.), N,N-dimethylformamide (2.10 g.), phosphoryl chloride (4.40 g.), tetrahydrofuran (110 ml.), 4-nitrobenzyl 7-amino-3-cephem-4-carboxylate (8.23 g.), acetone (16 ml.) and water (16 ml.) were treated in a similar manner to that of Example 15-(1) to give 4-nitrobenzyl 7-[2-(2formamidothiazol-4-yl)-2-iso-butoxyiminoacetamido]-3-cephem-4-carboxylate (syn isomer, 12.8 g.).

I.R. $\nu_{max}^{Nujol}$: 3240, 3050, 1780, 1720, 1700, 1655 cm$^{-1}$.

N.M.R. δ(DMSO-d$_6$, ppm): 0.92 (6H, d, J=7 Hz), 1.7∼2.2 (1H, m), 3.67 (2H, broad s), 3.91 (2H, d, J=7 Hz), 5.21 (1H, d, J=5 Hz), 5.95 (1H, dd, J=5 Hz, 9 Hz), 6.67 (1H, t, J=4 Hz), 7.37 (1H, s), 7.72 (2H, d, J=8 Hz), 8.24 (2H, d, J=8 Hz), 8.52 (1H, s), 9.68 (1H, d, J=9 Hz), 12.58 (1H, broad s).

(2) 4-Nitrobenzyl 7-[2-(2-formamidothiazol-4-yl)-2-isobutoxyiminoacetamido]-3-cephem-4-carboxylate (syn isomer, 14.2 g.), 10% palladium carbon (5.7 g.), methanol (57 ml.), tetrahydrofuran (142 ml.), acetic acid (1 ml.) and water (10 ml.) were treated in a similar manner to that of Example 15-(2) to give 7-[2-(2-formamidothiazol-4-yl)-2-isobutoxyiminoacetamido]-3-cephem-4-carboxylic acid (syn isomer, 4.25 g.).

I.R. $\nu_{max}^{Nujol}$: 3260, 1790, 1725, 1670 cm$^{-1}$.

N.M.R. δ(DMSO-d$_6$, ppm): 0.92 (6H,. d, J=6 Hz), 1.6∼2.3 (1H, m), 3.61 (2H, d, J=4 Hz), 3.91 (2H, d, J=6 Hz), 5.14 (1H, d, J=5 Hz), 5.88 (1H, dd, J=5 Hz, 8 Hz), 6.50 (1H, t, J=5 Hz), 7.40 (1H, s), 8.56 (1H, s), 9.64 (1H, d, J=8 Hz).

(3) 7-[2-(2-formamidothiazol-4-yl)-2-iso-butoxyiminoacetamido]-3-cephem-4-carboxylic acid (syn isomer, 4.1 g.), conc. hydrochloric acid (3.65 g.) and methanol (61.5 ml.) were treated in a similar manner to that of Example 15-(3) to give 7-[2-(2-aminothiazol-4-yl)-2- iso-butoxyiminoacetamido]-3-cephem-4-carboxylic acid (syn isomer, 2.4 g.).

I.R. $\nu_{max}^{Nujol}$: 3330, 1780, 1665, 1630, 1545 cm$^{-1}$.

N.M.R. δ(DMSO-d$_6$, ppm): 0.89 (6H, d, J=7 Hz), 1.6~2.2 (1H, m), 3.58 (2H, broad s), 3.84 (2H, d, J=7 Hz), 5.10 (1H, d, J=5 Hz), 5.82 (1H, dd, J=5 Hz, 9 Hz), 6.46 (1H, broad s), 6.68 (1H, s), 7.20 (2H, s), 9.53 (1H, d, J=9 Hz).

EXAMPLE 17

(1) 2-(2-Formamidothiazol-4-yl)-2-cyclohexyloxyiminoacetic acid (syn isomer, 0.9 g.), N,N-dimethylformamide (266 mg.), phosphoryl chloride (557 mg.), tetrahydrofuran (20 ml.), 4-nitrobenzyl 7-amino-3-cephem-4-carboxylate (1.05 g.), acetone (3 ml.) and water (3 ml.) were treated in a similar manner to that of Example 15-(1) to give 4-nitrobenzyl 7-[2-(2-formamidothiazol-4-yl)-2-cyclohexyloxyiminoacetamido]-3-cephem-4-carboxylate (syn isomer, 1.69 g.).

I.R. $\nu_{max}^{Nujol}$: 3260, 3170, 3070, 1785, 1725, 1700, 1655 cm$^{-1}$.

N.M.R. δ(DMSO-d$_6$, ppm): 0.8~2.2 (10H, m), 3.66 (2H, broad s), 4.10 (1H, m), 5.16 (1H, d, J=5 Hz), 5.42 (2H, s), 5.95 (1H, dd, J=5 Hz, 9 Hz), 6.66 (1H, broad s), 7.37 (1H, s), 7.70 (2H, d, J=8 Hz), 8.22 (2H, d, J=8 Hz), 8.50 (1H, s), 9.63 (1H, d, J=9 Hz), 12.60 (1H, broad s).

(2) 4-Nitrobenzyl 7-[2-(2-formamidothiazol-4-yl)-2-cyclohexyloxyiminoacetamido]-3-cephem-4-carboxylate (syn isomer, 2.0 g.), 10% palladium carbon (0.8 g.), methanol (8 ml.), tetrahydrofuran (20 ml.), acetic acid (0.14 ml.) and water (1.4 ml.) were treated in a similar manner to that of Example 15-(2) to give 7-[2-(2-formamidothiazol-4-yl)-2-cyclohexyloxyiminoacetamido]-3-cephem-4-carboxylic acid (syn isomer, 0.77 g.).

I.R. $\nu_{max}^{Nujol}$: 3275, 3070, 1780, 1675 cm$^{-1}$.

N.M.R. δ(DMSO-d$_6$, ppm): 0.8~2.2 (10H, m), 3.62 (2H, broad s), 4.12 (1H, m), 5.13 (1H, d, J=5 Hz), 5.87 (1H, dd, J=5 Hz, 9 Hz), 6.47 (1H, broad s), 7.37 (1H, s), 8.50 (1H, s), 9.58 (1H, d, J=9 Hz), 12.61 (1H, broad s).

(3) 7-[2-(2-Formamidothiazol-4-yl)-2-cyclohexyloxyiminoacetamido]-3-cephem-4-carboxylic acid (syn isomer, 0.72 g.), methanol (10.8 ml.) and conc. hydrochloric acid (0.61 g.) were treated in a similar manner to that of Example 15-(3) to give 7-[2-(2-aminothiazol-4-yl)-2-cyclohexyloxyiminoacetamido]-3-cephem-4-carboxylic acid (syn isomer, 0.28 g.).

I.R. $\nu_{max}^{Nujol}$: 3350, 1775, 1665, 1620, 1540 cm$^{-1}$.

N.M.R. δ(DMSO-d$_6$, ppm): 0.8~2.2 (10H, m), 3.60 (2H, broad s), 4.04 (1H, m), 5.09 (1H, d, J=5 Hz), 5.83 (1H, dd, J=5 Hz, 9 Hz), 6.45 (1H, t, J=4Hz), 6.67 (1H, s), 7.19 (2H, s), 9.48 (1H, d, J=9 Hz).

EXAMPLE 18

Phosphoryl chloride (0.84 g.) was added dropwise to a stirred suspension of 2-(2-aminothiazol-4-yl)-2-allyloxyiminoacetic acid (syn isomer, 1.0 g.), tetrahydrofuran (10 ml.) and water (0.05 ml.) at 5° C., and stirred at the same temperature for 20 minutes. Trimethylsilylacetamide (0.66 g.), phosphoryl chloride (0.84 g.) and N,N-dimethylformamide (0.45 g.) were added to a solution, and stirred at 5° C. for an hour to prepare the activated acid solution. On the other hand, trimethylsilylacetamide (4.0 g.) was added to a suspension of 7-amino-3-cephem-4-carboxylic acid (0.88 g.) in tetrahydrofuran (10 ml.) at 40° C., and stirred for 30 minutes. To the solution was added all at once the activated acid solution obtained above at −20° C., and stirred at 0° C. for an hour. After water (20 ml.) was added to the resultant solution at −20° C., the solution was adjusted to pH 7.5 with an aqueous solution of sodium bicarbonate. Ethyl acetate was added to the solution, and the aqueous layer was separated. The solution was washed with ethyl acetate and diisopropyl ether in turn, adjusted to pH 5.0 and treated with activated charcoal. After the solution was adjusted to pH 3.0, the precipitates were collected by filtration, washed with water and dried over phosphorus pentoxide to give 7-[2-(2-aminothiazol-4-yl)-2-allyloxyiminoacetamido]-3-cephem-4-carboxylic acid (syn isomer, 0.8 g.).

I.R. $\nu_{max}^{Nujol}$: 3300, 1780, 1660, 1630 cm$^{-1}$.

N.M.R. δ(DMSO-d$_6$, ppm): 3.67 (2H, d, J=4 Hz), 4.67 (2H, m), 5.17 (1H, d, J=5 Hz), 5.25 (1H, m), 5.50 (1H, m), 5.90 (1H, dd, J=5 Hz, 8 Hz), 6.03 (1H, m), 6.55 (1H, m), 6.80 (1H, s), 7.50 (2H, m), 9.68 (1H, d, J=8 Hz).

EXAMPLE 19

Phosphoryl chloride (1.4 g.) was added dropwise to a suspension of 2-(2-aminothiazol-4-yl)-2-propargyloxyiminoacetic acid (syn isomer, 1.7 g.) in tetrahydrofuran (15 ml.) below 7° C., and stirred at the same temperature for 10 minutes. Phosphoryl chloride (1.4 g.), trimethylsilylacetamide (1.3 g.) and N,N-dimethylformamide (0.76 g.) were added to a solution, and stirred for 20 minutes to prepare the activated acid solution. On the other hand, trimethylsilylacetamide (7.8 g.) was added to a suspension of 7-amino-3-cephem-4-carboxylic acid (1.5 g.) in tetrahydrofuran (20 ml.), and stirred at 40° C. for 30 minutes. To the solution was added all at once the activated acid solution obtained above at −20° C., and stirred for 30 minutes at 0° C. After adding water (20 ml.) to the resultant solution at −20° C., the solution was adjusted to pH 7.5 with an aqueous solution of sodium bicarbonate. The aqueous layer was separated, washed with ethyl acetate and diisopropyl ether in turn, and treated with activated charcoal at pH 5.5. The solution was adjusted to pH 3.0, and the precipitates were collected by filtration and dried over phosphorus pentoxide under reduced pressure to give 7-[2-(2-aminothiazol-4-yl)-2-propargyloxyiminoacetamido]-3-cephem-4-carboxylic acid (syn isomer, 1.47 g.).

I.R. $\nu_{max}^{Nujol}$: 3500, 3300, 1780, 1720, 1660, 1630 cm$^{-1}$.

N.M.R. δ(DMSO-d$_6$, ppm): 3.48 (1H, m), 3.67 (2H, m), 4.80 (2H, d, J=2 Hz), 5.17 (1H, d, J=5 Hz), 5.88 (1H, dd, J=5 Hz, 8 Hz), 6.55 (1H, m), 6.85 (1H, s), 7.33 (2H, m), 9.73 (1H, d, J=8 Hz).

EXAMPLE 20

(1) N,N-Dimethylformamide (3 drops) was added to a suspension of 2-(2-formamidothiazol-4-yl)-2-methoxyiminoacetic acid (syn isomer, 23 g.), and stirred at 60° C. for 5 minutes. After concentrating the solution in vacuo, benzene was added to the residue. The precipitates were collected by filtration, washed with benzene (30 ml.) three times and diethyl ether in turn to give 2-(2-formamidothiazol-4-yl)-2-methoxyiminoacetyl chloride (anti isomer, 18 g.). On the other hand, trimethylsilylacetamide (46 g.) was added to a suspension of 4-nitrobenzyl 7-amino-3-cephem-4-carboxylate (16.8 g.) in methylene chloride (168 ml.), and stirred at 40° C. for an hour. To the suspension was gradually added 2-(2-formamidothiazol-4-yl)-2-methoxyiminoacetyl chloride (anti isomer, 13.6 g.) at −5° to 0° C., and stirred at the same temperature for an hour. Water (150 ml.) was added to the resultant solution and stirred for 15 minutes. The precipitates were collected by filtration, washed with water and dried over phosphorus pentoxide under reduced pressure to give 4-nitrobenzyl 7-[2-(2-formamidothiazol-4-yl)-2-methoxyiminoacetamido]-3-cephem-4-carboxylate (anti isomer, 25.7 g.).

I.R. $\nu_{max}^{Nujol}$: 3300 (broad), 1780, 1730, 1680, 1520 cm$^{-1}$.

N.M.R. δ(DMSO-d$_6$, ppm): 3.70 (2H, broad s), 4.07 (3H, s), 5.19 (1H, d, J=5 Hz), 9.57 (1H, d, J=8 Hz), 6.00 (1H, dd, J=5 Hz, 8 Hz, 5.30 (2H, s), 6.70 (1H, t, J=4 Hz), 7.71, 8.25 (4H, A$_2$B$_2$, J=9 Hz), 8.07 (1H, s), 8.50 (1H, s), 12.55 (1H, broad s).

(2) A suspension of 4-nitrobenzyl 7-[2-(2-formamidothiazol-4-yl)-2-methoxyiminoacetamido]-3-cephem-4-carboxylate (anti isomer, 4.2 g.), 10% palladium carbon (1.7 g.), acetic acid (0.63 ml.), water (6.3 ml.), methanol (4.2 ml.), and tetrahydrofuran (84 ml.) was subjected to catalytic reduction in a hydrogen atmosphere at room temperature for 2 hours. After removing the catalyst by filtration, the filtrate was concentrated to a volume of about 15 ml. under reduced pressure. Water (30 ml.) and ethyl acetate (50 ml.) were added to the concentrated solution, and the solution was adjusted to pH 8.0 with sodium bicarbonate under stirring. The insoluble substance was removed by filtration, and the aqueous layer was separated and washed with ethyl acetate (50 ml.). The solution was treated with activated charcoal, and adjusted to pH 2.2 with 10% hydrochloric acid under ice cooling. The precipitates were collected by filtration and washed with water to give 7-[2-(2-formamidothiazol-4-yl)-2-methoxyiminoacetamido]-3-cephem-4-carboxylic acid (anti isomer, 2.52 g.).

I.R. $\nu_{max}^{Nujol}$: 3300 (broad), 1780, 1680, 1670, 1550 cm$^{-1}$.

N.M.R. δ(DMSO-d$_6$, ppm)- 3.63 (2H, broad s), 4.08 (3H, s), 5.15 (1H, d, J=5 Hz), 5.87 (1H, dd, J=5 Hz, 8 Hz), 6.55 (1H, t, J=4 Hz), 8.09 (1H, s), 8.52 (1H, s), 9.46 (1H, d, J=8 Hz).

(3) A suspension of 7-[2-(2-formamidothiazol-4-yl)-2-methoxyiminoacetamido]-3-cephem-4-carboxylic acid (anti isomer, 2.5 g.), conc. hydrochloric acid (2.5 ml.) and methanol (38 ml.) was stirred at room temperature for two hours. After treating the resultant solution with activated charcoal, the solution was concentrated in vacuo. The residue was crystallized out with diisopropyl ether (100 ml.), and the precipitates were collected by filtration, and washed with diisopropyl ether (30 ml.) to give 7-[2-(2-aminothiazol-4-yl)-2-methoxyiminoacetamido]-3-cephem-4-carboxylic acid hydrochloride (anti isomer, 2.1 g.). The crystals were added to water (20 ml.) and adjusted to pH 6.0 with sodium bicarbonate. The solution was subjected to column chromatography on nonionic adsorption resin "Diaion HP-20" [Trademark: manufactured by Mitsubishi Chemical Industries Ltd.] (75 ml.) with 10% diisopropyl ether. The eluate was adjusted to pH 3.5 with 10% hydrochloric acid, and the precipitates were collected by filtration and dried to give 7-[2-(2-aminothiazol-4-yl)-2-methoxyiminoacetamido]-3-cephem-4-carboxylic acid (anti isomer, 0.7 g.).

I.R. $\nu_{max}^{Nujol}$: 3400~3200 (broad), 1770, 1680, 1640, 1520 cm$^{-1}$.

N.M.R. δ(DMSO-d$_6$, ppm): 3.60 (2H, d, J=5 Hz), 4.00 (3H, s), 5.10 (1H, d, J=5 Hz), 5.82 (1H, dd, J=5 Hz, 8 Hz), 6.48 (1H, t, J=4 Hz), 7.13 (2H, broad), 7.47 (1H, s), 9.42 (1H, d).

EXAMPLE 21

(1) The Vilsmeier reagent was prepared from N,N-dimethylformamide (0.4 g.) and phosphoryl chloride (0.86 g.) in a usual manner. After the reagent was suspended in ethyl acetate (10 ml.), 2-(2-formamidothiazol-4-yl)-2-n-propoxyiminoacetic acid (syn isomer, 1.3 g.) was added to the stirred suspension under ice cooling and stirred at the same temperature for 30 minutes. The solution was added to a solution of 4-nitrobenzyl 7-amino-3-chloro-3-cephem-4-carboxylate hydrochloride (2.0 g.), trimethylsilylacetamide (5.2 g.) and ethyl acetate (40 ml.) at −25° C., and stirred at −20° to −10° C. for 1.5 hours. After adding water into the resultant solution, the solution was extracted with ethyl acetate (60 ml.). The aqueous layer was extracted with ethyl acetate (50 ml.). The extracts were combined together, washed with a saturated aqueous solution of sodium bicarbonate and a saturated aqueous solution of sodium chloride in turn, and dried over magnesium sulfate. The solution was concentrated in vacuo, and the residue was triturated with diethyl ether. The precipitates were collected by filtratation, washed and dried to give 4-nitrobenzyl 7-[2-(2-formamidothiazol-4-yl)-2-n-propoxyiminoacetamido]-3-chloro-3-cephem-4-carboxylate (syn isomer, 2.55 g.).

I.R. $\nu_{max}^{Nujol}$: 3250~3150, 1780, 1730, 1690, 1660, 1610, 1550, 1520 cm$^{-1}$.

N.M.R. δ(DMSO-d$_6$, ppm): 0.87 (3H, t, J=7 Hz), 1.63 (1H, m), 3.88 (2H, q, J=17 Hz), 3.97 (2H, q, J=7 Hz), 5.30 (1H, d, J=5 Hz), 5.40 (2H, s), 5.92 (1H, dd, J=5 Hz, 8 Hz), 7.33 (1H, s), 7.65 (2H, d, J=9 Hz), 8.20 (2H, d, J=9 Hz), 8.47 (1H, s), 9.70 (1H, d, J=8 Hz), 12.40 (1H, s).

(2) A suspension of 4-nitrobenzyl 7-[2-(2-formamidothiazol-4-yl)-2-n-propoxyiminoacetamido]-3-chloro-3-cephem-4-carboxylate (syn isomer, 2.4 g.), 10% palladium carbon (1.0 g.), methanol (24 ml.), water (3.6 ml.) and tetrahydrofuran (48 ml.) was subjected to catalytic reduction under ordinary pressure at room temperatures. After removing insoluble substance by filtration, the filtrate was concentrated in vacuo. Water and ethyl acetate were added to the residue, and adjusted to pH 8 with a saturated aqueous solution of sodium bicarbonate. The insoluble substance was removed by filtration, and the aqueous layer was separated. Ethyl acetate was added to the solution, adjusted to pH 2.0 with hydrochloric acid and extracted with ethyl acetate. The ethyl acetate solution and extract were combined together, washed with a saturated aqueous solution of sodium chloride and dried over magnesium sulfate. The solution was concentrated in vacuo, and the residue was triturated with diethyl ether and collected by filtration to give 7-[2-(2-formamidothiazol-4-yl)-2-n-propoxyiminoacetamido]-3-chloro-3-cephem-4-carboxylic acid (syn isomer, 1.6 g.).

I.R. $\nu_{max}^{Nujol}$: 3300~3150, 1780, 1720, 1685, 1650, 1540 cm$^{-1}$.

N.M.R. δ(DMSO-d$_6$, ppm): 0.93 (3H, t, J=7 Hz), 1.72 (1H, m), 3.88 (2H, q, J=18 Hz), 4.08 (2H, q, J=7 Hz), 5.33 (1H, d, J=5 Hz), 5.92 (1H, dd, J=5 Hz, 8 Hz). 7.43 (1H, s), 8.57 (1H, s), 9.73 (1H, d, J=8Hz).

(3) A suspension of 7-[2-(2-formamidothiazol-4-yl)-2-n-propoxyiminoacetamido]-3-chloro-3-cephem-4-carboxylic acid (syn isomer, 1.5 g.), conc. hydrochloric acid (0.7 ml.) and methanol (30 ml.) was stirred at room temperature for 1.5 hours. After removing methanol from the resultant solution in vacuo, water (30 ml.) was added to the residue. After the solution was adjusted to pH 7.5 with a saturated aqueous solution of sodium bicarbonate, the insoluble substance was removed by filtration. The filtrate was adjusted to pH 3 with 10% hydrochloric acid. The precipitates were collected by filtration and dried over phosphorus pentoxide to give 7-[2-(2-aminothiazol-4-yl)-2-n-propoxyiminoacetamido]-3-chloro-3-cephem-4-carboxylic acid (syn isomer, 0.6 g.).

I.R. $\nu_{max}^{Nujol}$: 3300, 1780, 1670, 1630, 1530 cm$^{-1}$.

N.M.R. $\delta$(DMSO-d$_6$, ppm): 0.92 (3H, t, J=7 Hz), 1.67 (1H, m), 3.70 (2H, q, J=18 Hz), 4.00 (2H, q, J=7 Hz), 5.25 (1H, d, J=5 Hz), 5.83 (1H, dd, J=5 Hz, 8 Hz,), 6.75 (1H, s), 9.63 (1H, d, J=8 Hz).

EXAMPLE 22

2-(2-Aminothiazol-4-yl)-2-n-hexyloxyiminoacetic acid (syn isomer, 3 g.), water (0.15 g.), phosphoryl chloride (3.8 g.), trimethylsilyacetamide (10.7 g.), N,N-dimethylformamide (1.0 g.), tetrahydrofuran (50 ml.) and 7-amino-3-cephem-4-carboxylic acid (2.0 g.) were treated in a similar manner to that of Example 18 to give 7-[2-(2-aminothiazole-4-yl)-2-n-hexyloxyiminoacetamido]-3-cephem-4-carboxylic acid (syy isomer, 1.1 g.).

I.R. $\nu_{max}^{Nujol}$ 3250, 1760, 1640, 1600 cm$^{-1}$.

N.M.R. $\delta$(DMSO-d$_6$, ppm): 1.88 (3H, m), 1.1~1.9 (8H, m), 3.60 (2H, m), 4.06 (2H, t, J=6 Hz), 5.10 (1H, d, J=5 Hz), 5.82 (1H, dd, J=5Hz, 8 Hz), 6.46 (1H, m), 6.70 (1H, s), 7.26 (2H, m), 9.56 (1H, d, J=8 Hz).

EXAMPLE 23

2-(2-formamidothiazol-4-yl)-2-propargyloxyiminoacetic acid (syn isomer, 0.506 g.), N,N-dimethylformamide (0.161 g.), phosphoryl chloride (0.337 g. and ethyl acetate (7.9 ml.) were treated in a similar manner to that of Example 15 to give the activated acid solution.

On the other hand, trimethylsilylacetamide (1.85 g.) and bis(trimethylsilyl)acetamide (1.60 g.) were added to a suspension of 4-nitrobenzyl 7-amino-3-hydroxy-3-cephem-4-carboxylate (0.703 g.) in ethyl acetate (10 ml.) and stirred at room temperature for an hour. To the solution was added the activated acid solution obtained above at $-10°$ C. all at once, and stirred at the same temperature for an hour. Water (20 ml.) and ethyl acetate (20 ml.) were added to the solution. The organic layer was separated, washed with a saturated aqueuos solution of sodium bicarbonate (8 ml.) and an aqueous solution of sodium chloride (15 ml.), and dried over magnesium sulfate. After the solution was concentrated in vacuo, the residue was pulverized with diethyl ether and the precipitates were collected by filtration to give 4-nitrobenzyl 7-[2-(2-formamidothiazol-4-yl)-2-propargyloxyiminoacetamido]-3-hydroxy-3-cephem-4-carboxylate (syn isomer, 0.71 g.).

I.R. $\nu_{max}^{Nujol}$: 3270, 1770, 1740, 1670 cm$^{-1}$.

N.M.R. $\delta$ (DMSO-d$_6$, ppm): 3.39 (1H, m), 3.63 (2H, broad s), 4.90 (2H, broad s), 5.25–590 (4H, m), 7.57 (1H, s), 7.83 (2H, d, J=9Hz), 8.40 (2H, d, J=9 Hz), 8.67 (1H, s), 9.80 (1H, d, J=8 Hz, 12.83 (1H, broad s).

EXAMPLE 24

2-(2-Formamidothiazol-4-yl)-2-propoxyiminoacetic acid (syn isomer, 0.515 g.), N,N-dimethylformamide (0.161 g.), phosphoryl chloride (0.337 g.) and ethyl acetate (7.9 ml.) were treated in a similar manner to that of Example 15 to give the activated acid solution. On the other hand, trimethylsilylacetamide (1.85 g.) and bis(trimethylsilyl)acetamide (1.60 g.) were added to a suspension of 4-nitrobenzyl 7-amino-3-hydroxy-3-cephem-4-carboxylate (0.703 g.) in ethyl acetate (10 ml.), and stirred at room temperature for an hour. To the solution was added the activated acid solution obtained above at $-10°$ C. all at once, and stirred at the same temperature for an hour. To the resultant solution were added water (20 ml.) and ethyl acetate (20 ml.). The organic layer was separated, washed with a saturated aqueous solution of sodium bicarbonate (8 ml.) and water (14 ml.) and dried over magnesium sulfate. After the solution was concentrated in vacuo, the residue was pulverized with diethyl ether, and the precipitates were collected by filtration to give 4-nitrobenzyl 7-[2-(2-formamidothiazol-4-yl)-2-propoxyiminoacetamido]-3-hydroxy-3-cephem-4-carboxylate (syn isomer, 0.75 g.).

I.R. $\nu_{max}^{Nujol}$: 3250, 1765, 1740, 1670 cm$^{-1}$.

N.M.R. $\delta$ (DMSO-d$_6$, ppm): 0.90 (3H, t, J=8 Hz), 1.67 (2H, m), 3.40 (2H, AB-q, J=20 Hz), 4.08 (2H, q, J=8Hz), 5.03–5.83 (4H, m), 7.40 (1H, s), 7.70 (2H, d, J=9Hz), 8.27 (2H, d, J=9Hz), 8.53 (1H, s), 9.50 (1H, d, J=8Hz, 12.60 (1H, broad s).

EXAMPLE 25

2-(2-Formamidothiazol-4-yl)-2-isobutoxyiminoacetic acid (syn isomer, 0.54 g.), N,N-dimethylformamide (0.16 g.), phosphoryl chloride (0.34 g.) and ethyl acetate (10 ml.) were treated in a similar manner to that of Example 15 to give the activated acid solution. On the other hand, trimethylsilyacetamide (1.85 g.) and bis(-trimethylsilyl)acetamide (1.62 g.) were added to a suspension of 4-nitrobenzyl 7-amino-3-hydroxy-3-cephem-4-carboxylate (0.7 g.) in ethyl acetate (10 ml.) and stirred at 40° C. for 30 minutes. The activated acid solution obtained above was added to the solution at $-20°$ C. all at once, and stirred at the same temperature for an hour. Water (10 ml.) was added to the resultant solution, and the organic layer was separated, washed with water, an aqueous solution of sodium bicarbonate and a saturated aqueous solution of sodium chloride, and then dried. After the solution was concentrated in vacuo, the residue was pulverized with diisopropyl ether. The precipitates were collected by filtration, washed with diisopropyl ether and dried to give 4-nitrobenzyl 7-[2-(2-formamidothiazol-4-yl)-2-isobutoxyiminoacetamido]-3-hydroxy-3-cephem-4-carboxylate (syn isomer, 1.09 g.).

I.R. $\nu_{max}^{Nujol}$: 3250, 3050, 1750, 1650, 1610 cm$^{-1}$.

N.M.R. $\delta$ (DMSO-d$_6$, ppm): 0.97 (6H, d, J=6Hz),=2.0 (1H, m), 3.60 (2H, AB-q, J=18Hz), 3.95 (2H, d, J=6Hz), 5.1–5.8 (4H, m), 7.53 (1H, s), 7.63 (2H, d, J=8Hz), 8.18 (2H, d, J=8Hz), 8.58 (1H, s), 9.47 (1H, d, J=9Hz), 12.77 (1H, broad s).

EXAMPLE 26

N,N-Dimethylformamide (0.114 g.), phosphoryl chloride (0.240 g.) and ethyl acetate (0.5 ml.) were reacted in a conventional manner to give a Vilsmeier reagent. Ethyl acetate (5 ml.) and 2-(2-formamidothiazol-4-yl)-2-ethoxyiminoacetic acid (syn isomer, 0.35 g.) were added at the same temperature for 30 minutes to give the activated acid solution. On the other hand, trimethylsilylacetamide (1.31 g.) and bis(trimethylsilyl)acetamide (1.14 g.) were added to a suspension of 4-nitrobenzyl 7-amino-3-hydroxy-3-cephem-4-carboxylate (0.50 g.) in ethyl acetate (7.5 ml.) and stirred at room temperature for an hour. To the solution was added the activated acid solution obtained above all at once at −10° C., and stirred at the same temperature for 30 minutes. Water (15 ml.) and ethyl acetate (15 ml.) were added to the resultant solution. The organic layer was separated, washed with a saturated aqueous solution of sodium bicarbonate (15 ml.) and water (10 ml.), dried over magnesium sulfate and concentrated in vacuo. The residue was pulverized with diethyl ether and the precipitates were collected by filtration to give 4-nitrobenzyl 7-[2-(2-formamidothiazol-4-yl)-2-ethoxyiminoacetamido]-3-hydroxy-3-cephem-4-carboxylate (syn isomer, 0.634 g.).

I.R. $\nu_{max}^{Nujol}$: 3220, 1760, 1740, 1670 cm$^{-1}$.

N.M.R. $\delta$ (DMSO-d$_6$, ppm): 1.24 (3H, t, J=8Hz), 3.36 (2H, AB-q, J=20Hz), 4.15 (2H, q, J=8Hz), 5.10–5.60 (4H, m), 7.37 (1H, s), 7.65 (2H, d, J=9Hz), 8.22 (2H, d, J=9Hz), 8.48 (1H, s), 9.52 (1H, d, J=8Hz), 12.58 (1H, broad s).

EXAMPLE 27

(1) 2-(2-Formamidothiazol-4-yl)-2-pentyloxyiminoacetic acid (syn isomer, 4.14 g.), 4-nitrobenzyl 7-amino-3-cephem-4-carboxylate (4.5 g.), N,N-dimethylformamide (1.41 g.), phosphoryl chloride (2.96 g.), tetrahydrofuran (72 ml.), acetone (15 ml.) and water (15 ml.) were treated in a similar manner to that of Example 15 -(1) to give 4-nitrobenzyl 7-[2-(2-formamidothiazol-4-yl)-2-pentyloxyiminoacetamido]-3-cephem-4-carboxylate (syn isomer, 8.1 g.).

I.R. $\nu_{max}^{Nujol}$: 3240, 3050, 1780, 1730, 1655 cm$^{-1}$.

N.M.R. $\delta$ (DMSO-d$_6$, ppm): 0.6–2.0 (9H, m), 3.66 (2H, s), 4.10 (2H, t, J=6Hz), 5.19 (1H, d, J=5Hz), 5.42 (2H, s), 5.95 (1H, dd, J=5Hz, 8Hz), 6.16 (1H, broad s), 7.38 (1H, s), 7.72 (2H, d, J=9Hz), 8.26 (2H, d, J=9Hz), 8.54 (1H, s), 9.69 (1H, d, J=8Hz), 12.69 (1H, broad s).

(2) 4-Nitrobenzyl 7-[2-(2-formamidothiazol-4-yl)-2-pentyloxyiminoacetamido]-3-cephem-4-carboxylate (syn isomer, 8 g.), 10% palladium carbon (3.6 g.), methanol (36 ml.), tetrahydrofuran (90 ml.), acetic acid (0.63 g.) and water (6.3 ml.) were treated in a similar manner to that of Example 15 -(2) to give 7-[2-(2-formamidothiazol-4-yl)-2-pentyloxyiminoacetamido]-3-cephem-4-carboxylic acid (syn isomer, 3.4 g.).

I.R. $\nu_{max}^{Nujol}$: 3275, 3075, 1795, 1700, 1660, 1630 cm$^{-1}$.

N.M.R. $\delta$ (DMSO-d$_6$, ppm):0.6–2.0 (9H, m), 3.60 (2H, d, J=4Hz), 4.12 (2H, t, J=6Hz), 5.14 (1H, d, J=5Hz), 5.87 (1H, dd, J=5Hz, 9Hz), 6.49 (1H, t, J=3Hz), 7.40 (1H, s), 8.53 (1H, s), 9.64 (1H, d, J=9Hz), 12.68 (1H, s).

(3) 7-[2-(2-Formamidothiazol-4-yl)-2-pentyloxyiminoacetamido]-3-cephem-4-carboxylic acid (syn isomer, 3.3 g.), conc. hydrochloric acid (2.80 g.), tetrahydrofuran (20 ml.) and methanol (50 ml.) were treated in a similar manner to that of Example 15-(3) to give 7-[2-(2-aminothiazol-4-yl)-2-pentyloxyiminoacetamido]-3-cephem-4-carboxylic acid (syn isomer, 2.3 g.)

I.R. $\nu_{max}^{Nujol}$: 3300, 1775, 1650, 1540 cm$^{-1}$.

N.M.R. $\delta$ (DMSO- d$_6$, ppm): 0.6–2.0 (9H, m), 3.56 (2H, d, J=2Hz), 4.03 (2H, t, J=6Hz), 5.08 (1H, d, J=5Hz), 5.81 (1H, dd, J=5Hz, 8Hz), 6.46 (1H, t, J=4Hz), 6.69 (1H, s), 7.20 (2H, s), 9.15 (1H, d, J=8Hz).

EXAMPLE 28

(1) Triethylamine (3.41 g.), N,N-dimethylphenylamine (10.3 g.) and trimethylchlorosilan (5.64 g.) were added to a stirred solution of 7-phenylacetamido-3-tosyloxy-3-cephem-4-carboxylic acid (15 g.) in methylene chloride (150 ml.) at room temperature in turn, and the solution was stirred at room temperature for an hour. Phosphorus pentachloride (7.03 g.) was added to the solution at −35° C. and stirred at −25° to −20° C. for 1.5 hours. Methanol (61 ml.) was added to the solution and stirred at the same temperature for 40 minutes. To the resultant solution was added water (50 ml.) at −20° to −10° C. The organic layer was separated and washed with water twice. The aqueous layer and the washings were combined, and washed with methylene chloride twice and diethyl ether in turn. After the solution was adjusted to pH 4.7 with 10% aqueous sodium hydroxide under cooling, the precipitates were collected by filtration, washed with water, acetone and diethyl ether in turn, and then dried over phosphorus pentoxide to give 7-amino-3-tosyloxy-3-cephem-4-carboxylic acid (5.01 g.), mp 172° C. (dec.).

I.R. $\nu_{max}^{Nujol}$: 3210, 1800, 1653, 1620 cm$^{-1}$.

N.M.R. $\delta$ (D$_2$O+NaHCO$_3$, ppm): 2.45 (3H, s), 3.51 (2H, q, J=18Hz), 5.08 (1H, d, J=5Hz), 5.51 (1H, d, J=5Hz), 7.48 (2H, d, J=9Hz), 7.84 (2H, d, J=9Hz).

(2) 2-(2-Aminothiazol-4-yl)-2-methoxyiminoacetic acid (syn isomer, 0.76 g.), N,N-dimethylformamide (0.33 g.), phosphoryl chloride (1.46 g.), trimethylsilylacetamide (0.5 g.) and ethyl acetate (10 ml.) were treated to give the activated acid solution in a conventional manner.

On the other hand, trimethylsilylacetamide (2.7 g.) was added to a suspension of 7-amino-3-tosyloxy-3-cephem-4-carboxylic acid (1.0 g.) in ethyl acetate (15 ml.) and stirred at room temperature.

To the solution was added the activated acid solution obtained above at −15° C. all at once, and stirred at −5°–5° C. for an hour. After the resultant solution was chilled to −20° C., water (30 ml.) was added to the chilled solution and adjusted to pH 6.5 with an aqueous solution of sodium bicarbonate. The insoluble substance was removed by filtration. The aqueous layer was separated and adjusted to pH 3.0 with hydrochloric acid. The precipitates were collected by filtration and dried to give 7-[2-(2-aminothiazol-4-yl)-2-methoxyiminoacetamido]-3-tosyloxy-3-cephem-4-carboxylic acid (syn isomer, 1.0 g.).

I.R. $\nu_{max}^{Nujol}$: 3350, 1780, 1670, 1630 cm$^{-1}$.

N.M.R. $\delta$ (DMSO-d$_6$, ppm): 2.17 (3H, s), 3.71 (2H, m), 3.92 (3H, s), 5.32 (1H , d, J=5Hz), 5.87 (1H, dd, J=5Hz, 8Hz), 6.82 (1H, s), 7.50 (2H, d, J=8Hz), 7.92 (2H, d, J=8Hz), 9.73 (1H, d, J=8Hz).

EXAMPLE 29

(1) 2-(2-Formamidothiazol-4-yl)-2-ethoxycarbonylmethoxyiminoacetic acid (syn isomer, 1.35 g.), 4-nitrobenzyl 7-amino-3-cephem-4-carboxylate (1.54 g.), N,N-dimethylformamide (393 mg.), phosphoryl chloride (825 mg.), tetrahydrofuran (21.2 ml.), acetone (3.9 ml.) and water (3.9 ml.) were treated in a similar manner to that of Example 15- (1) to give 4-nitrobenzyl 7-[2-(2-formamidothiazol-4-yl)-2-ethoxycarbonylmethoxyiminoacetamido]-3-cephem-4-carboxylate (syn isomer 2.52 g.).

I.R. $\nu_{max}^{Nujol}$: 3250, 1790, 1730, 1690, 1640 cm$^{-1}$.

N.M.R. $\delta$ (DMSO-d$_6$, ppm): 1.23 (3H, t, J=7Hz), 3.66 (2H, s), 4.13 (2H, q, J=7Hz), 4.74 (2H, s), 5.22 (1H, d, J=5Hz), 5.42 (2H, s), 5.98 (1H, dd, J=5Hz, 9Hz), 6.49 (1H, broad s), 7.43 (1H, s), 7.71 (2H, d, J=9Hz), 8.23 (2H, d, J=9Hz), 8.52 (1H, s), 9.68 (1H, d, J=9Hz), 12.66 (1H, s).

(2) 4-Nitrobenzyl 7-[2-(2-formamidothiazol-4-yl)-2-ethoxycarbonylmethoxyiminoacetamido]-3-cephem-4- carboxylate (syn isomer, 2.52 g.), 10% palladium carbon (1.3 g.) ethanol (13 ml.), tetrahydrofuran (25 ml.), acetic acid (0.22 ml.) and water (2.2 ml.) were treated in a similar manner to that of Example 15-(2) to give 7-[2-(2-formamidothiazol-4-yl)-2-ethoxycarbonylmethoxyiminoacetamido]-3-cephem-4-carboxylic acid (syn isomer, 0.4 g.).

I.R. $\nu_{max}^{Nujol}$: 3250, 3060, 1780, 1750, 1690, 1660 cm$^{-1}$.

N.M.R. $\delta$ (DMSO-d$_6$, ppm): 1.23 (3H, t, J=7 Hz), 3.61 (2 H, broad s), 4.15 (2H, q, J=7 Hz), 4.73 (2H, s), 5.13 (1H, d, J=5 Hz), 5.87 (1 H, dd, J=5 Hz, 9 Hz), 6.48 (1H, broad s), 7.43 (1H, s), 8.50 (1H, s), 9.62 (1H, d, J=9 Hz), 12.58 (1H, s).

(3) A solution of 7-[2-(2-formamidothiazol-4-yl)-2-ethoxycarbonylmethoxyiminoacetamido]-3-cephem-4-carboxylic acid (syn isomer, 0.35 g.), conc.hydrochloric acid (0.39 g.), ethanol (5.3 ml.) and tetrahydrofuran (8 ml.) was stirred at room temperature for 4.5 hours. After the resultant solution was concentrated in vacuo, the residue was dissolved in an aqueous solution of sodium bicarbonate, treated with activated charcoal and filtered. The filtrate was adjusted to pH 3.5 with 10% hydrochloric acid under ice cooling. The precipitates were collected by filtration, washed with water and dried to give 7-[2-(2-aminothiazol-4-yl)-2-ethoxycarbonylmethoxyiminoacetamido]-3-cephem-4-carboxylic acid (syn isomer, 0.1 g.).

I.R. $\nu_{max}^{Nujol}$: 3250, 3050, 1775, 1720, 1660, 1630, 1550 cm$^{-1}$.

N.M.R. $\delta$ (DMSO-d$_6$, ppm): 1.21 (3H, t, J=7 Hz), 3.59 (2H, s), 4.14 (2H, q, J=7 Hz), 4.66 (2H, s), 5.10 (1H, d, J=5 Hz), 5.83 (1H, dd, J=5 Hz, 8 Hz), 6.47 (1H, broad s), 6.78 (1H, s), 7.23 (2H, s), 9.52 (1H, d, J=8 Hz).

EXAMPLE 30

(1) The Vilsmeier reagent was prepared from N,N-dimethylformamide (0.32 g.) and phosphoryl chloride (0.67 g.) in a conventional manner. After the reagent was suspended in ethyl acetate (10 ml.), 2-(2-formamidothiazol-4-yl)-2-(2,2,2-trifluoroethoxyiminoacetic acid (syn isomer, 1.2 g.) was added to the stirred suspension under ice cooling and stirred at the same temperature for 30 minutes. The solution was added to a solution of 7-amino-3-cephem-4-carboxylic acid (0.8 g.), and trimethylsilylacetamide (4.2 g.) in ethyl acetate (20 ml.) at $-25°$ C., and stirred at $-20°$ to $-10°$ C. for an hour. Water and ethyl acetate were added to the resultant solution, and ethyl acetate layer was separated. The aqueous layer was extracted again with ethyl acetate. Water was added to the combined extract and adjusted to pH 7.5 with a saturated aqueous solution of sodium bicarbonate, and then the aqueous layer was separated. Ethyl acetate was added to the aqueous layer, adjusted to pH 1.5 with hydrochloric acid and the ethyl acetate layer was separated. The aqueous layer was extracted again with ethyl acetate. The extracts were combined, washed with a saturated aqueous solution of sodium chloride and dried over magnesium sulfate. After concentrating the solution in vacuo, the residue was triturated with diethyl ether, and the precipitates were collected by filtration and dried to give 7-[2-(2-formamidothiazol-4-yl)-2-(2,2,2-trifluoroethoxyiminoacetamido]-3-cephem-4-carboxylic acid (syn isomer, 1.55 g.).

I.R. $\nu_{max}^{Nujol}$: 3250, 1790, 1690, 1660, 1630, 1605, 1580, 1550 cm$^{-1}$.

N.M.R. $\delta$ (DMSO-d$_6$, ppm): 3.67 (2H, broad s), 4.78 (2H, q, J=8.5 Hz), 5.17 (1H, d, J=5 Hz), 5.92 (1H, dd, J=5 Hz, 8 Hz), 6.53 (1H, t, J=4 Hz), 7.52 (1H, s), 8.52 (1H, s), 9.83 (1H, d, J=8 Hz), 12.67 (1 H, broad s).

(2) A suspension of 7-[2-(2-formamidothiazol-4-yl)-2-(2,2,2-trifluoroethoxyimino)acetamido]-3-cephem-4-carboxylic acid (syn isomer, 1.5 g.), conc. hydrochloric acid (1.3 ml.), tetrahydrofuran (10 ml.) and methanol (30 ml.) was treated in a similar manner to that of Example 21-(3) to give 7-[2-(2-aminothiazol-4-yl)-2-(2,2,2-trifluoroethoxyimino)acetamido]-3-cephem-4-carboxylic acid (syn isomer, 1.1 g.).

I.R. $\nu_{max}^{Nujol}$: 3450, 3300, 1780, 1660, 1625, 1590, 1550 cm$^{-1}$.

N.M.R. $\delta$ (DMSO-d$_6$, ppm): 3.60 (2H, broad s), 4.70 (2H, q, J=8.5 Hz), 5.13 (1H, d, J=5 Hz), 5.87 (1H, dd, J=5 Hz, 8 Hz), 6.52 (1H, t, J=4 Hz), 6.87 (1H, s), 9.80 (1H, d, J=8 Hz).

EXAMPLE 31

(1) A solution of 2-(2-formamidothiazol-4-yl)-2-(2-chloroethoxyimino)acetic acid (syn isomer, 3.47 g.), N,N-dimethylformamide (1.1 g.) and phosphoryl chloride (2.3 g.) in ethyl acetate (35 ml.), and a solution of 7-amino-3-cephem-4-carboxylic acid (2.5 g.) and bis(trimethylsilyl)acetamide (12.7 g.) in ethyl acetate (25 ml.) were treated in a similar manner to that of Example 15-(1) to give 7-[2-(2-formamidothiazol-4-yl)-2-(2-chloroethoxyimino)acetamido]-3-cephem-4-carboxylic acid (syn isomer, 1.85 g.).

I.R. $\nu_{max}^{Nujol}$: 3250, 3050, 1780, 1695, 1685, 1655, 1625 cm$^{-1}$.

N.M.R. $\delta$ (DMSO-d$_6$, ppm): 3.62 (2H, d, J=4 Hz), 3.86 (2H, t, J=6 Hz), 4.37 (2H, t, J=6 Hz), 5.16 (1H, d, J=5 Hz), 5.90 (1H, dd, J=5 Hz, 9 Hz), 6.52 (1H, t, J=4 Hz), 7.50 (1H, s), 8.53 (1H, s), 9.68 (1H, d, J=9 Hz), 12.72 (1H, broad s).

(2) 7-[2-(2-Formamidothiazol-4-yl)-2-(2-chloroethoxyimino)acetamido]-3-cephem-4-carboxylic acid (syn isomer, 1.8 g.), conc. hydrochloric acid (1.6 g.), methanol (27 ml.) and tetrahydrofuran (40 ml.) were treated in a similar manner to that of Example 15-(3) to give 7-[2-(2-aminothiazol-4-yl)-2-(2-chloroethoxyimino)acetamido]-3-cephem-4-carboxylic acid (syn isomer, 1.4 g.).

I.R. $\nu_{max}^{Nujol}$: 3440, 3300, 3070, 1780, 1660, 1625, 1555 cm$^{-1}$.

N.M.R. $\delta$ (DMSO-d$_6$, ppm): 3.60 (2H, s), 3.80 (2H, t, J=6 Hz), 4.30 (2H, t, J=6 Hz), 5.10 (1H, d, J=5 Hz), 5.83 (1H, dd, J=5 Hz, 9 Hz), 6.47 (1H, s), 6.78 (1H, s), 7.24 (2H, s), 9.58 (1H, d, J=9 Hz).

EXAMPLE 32

(1) A solution of 2-(2-formamidothiazol-4-yl)-2-(tert-butoxycarbonylmethoxyimino)acetic acid (syn isomer, 3.2 g.), N,N-dimethylformamide (0.852 g.) and phosphoryl chloride (1.79 g.) in ethyl acetate (34 ml.) and a solution of 7-amino-3-cephem-4-carboxylic acid (1.95 g.) and bis(trimethylsilyl)acetamide (9.9 g.) in ethyl acetate (19.5 ml.) were treated in a similar manner to that of Example 15-(1) to give 7-[2-(2-formamidothiazol-4-yl)-2-(tert-butoxycarbonylmethoxyimino)acetamido]-3-cephem-4-carboxylic acid (syn isomer, 2.9 g.).

I.R. $\nu_{max}^{Nujol}$: 3260, 3180, 3060, 1785, 1730, 1690, 1640 cm$^{-1}$.

N.M.R. $\delta$(DMSO-d$_6$, ppm): 1.44 (9H, s), 3.63 (2H, s), 4.62 (2H, s), 5.12 (1H, d, J=5 Hz), 5.87 (1H, dd, J=5

Hz, 9 Hz), 6.48 (1H, broad s), 7.42 (1H, s), 8.50 (1H, s), 9.57 (1H, d, J=9 Hz), 12.62 (1H, broad s).

(2) A mixture of 7-[2-(2-formamidothiazol-4-yl)-2-(tert-butoxycarbonylmethoxyimino)acetamido]-3-cephem-4-carboxylic acid (syn isomer, 2.8 g.), anisole (2.8 ml.) and trifluoroacetic acid (11.2 ml.) was stirred at room temperature for an hour. Ethyl acetate and water were added to the resultant solution and adjusted to pH 7.0 with sodium bicarbonate. The aqueous layer was separated, and the ethyl acetate layer was extracted with water. The aqueous extracts were combined, washed with ethyl acetate and diethyl ether in turn, and then adjusted to pH 2.0 with 10% hydrochloric acid under ice cooling. The precipitates were collected by filtration, washed with water and dried to give 7-[2-(2-formamidothiazol-4-yl)-2-carboxymethoxyiminoacetamido]-3-cephem-4-carboxylic acid (syn isomer, 1.43 g.).

I.R. $\nu_{max}^{Nujol}$: 3270, 3120, 3070, 1760, 1720, 1690, 1660, 1620 cm$^{-1}$.

N.M.R. δ (DMSO-d$_6$, ppm): 3.60 (2 H, s), 4.63 (2H, s), 5.11 (1H, d, J=5 Hz), 5.88 (1 H, dd, J=5 Hz, 9 Hz), 6.48 (1 H, t, J=4 Hz), 7.44 (1H, s), 8.52 (1H, s), 9.59 (1H, d, J=9 Hz), 12.64 (1H, broad s).

(3) A mixture of 7-[2-(2-formamidothiazol-4-yl)-2-carboxymethoxyiminoacetimido]-3-cephem-4-carboxylic acid (syn isomer, 1.35 g.), conc. hydrochloric acid (3.926 g.), methanol (20 ml.), water (10 ml.) and tetrahydrofuran (40 ml.) was stirred at 30° C. for 6 hours. The resultant solution was concentrated in vacuo in order to evaporate the methanol, and the aqueous solution obtained was adjusted to pH 4.2 with 10% aquoeus solution of sodium hydroxide. The solution was adjusted to pH 3.0 with 10% hydrochloric acid. The precipitates were collected by filtration and dried to give 7-[2-(2-aminothiazol-4-yl)-2-carboxymethoxyiminoacetamido]-3-cephem-4-carboxylic acid (syn isomer, 0.8 g.).

I.R. $\nu_{max}^{Nujol}$: 3300 (broad), 3200 (broad), 1775, 1670, 1635 cm$^{-1}$.

N.M.R. δ(DMSO-d$_6$, ppm): 3.64 (2H, s), 4.64 (2H, s), 5.13 (1H, d, J=5 Hz), 5.86 (1H, dd, J=5 Hz, 7 Hz), 6.49 (1H, t, J=4 Hz), 6.82 (1H, s), 7.33 (2H, s), 9.57 (1H, d, J=9 Hz).

EXAMPLE 33

(1) A solution of 2-(2-formamidothiazol-4-yl)-2-(2,2,2-trifluoroethoxyimino)acetic acid (syn isomer, 0.9 g.), N,N-dimethylformamide (0.24 g.) and phosphoryl chloride (0.5 g.) in ethyl acetate (10 ml.) and a solution of 4-nitrobenzyl 7-amino-3-chloro-3-cephem-4-carboxylate hydrochloride (1.23 g.) and trimethylsilylacetamide (2.8 g.) in ethyl acetate (20 ml.) were treated in a similar manner to that of Example 21-(1) to give 4-nitrobenzyl 7-[2-(2-formamidothiazol-4-yl)-2-(2,2,2-trifluoroethoxyimino)acetamido]-3-chloro-3-cephem-4-carboxylate (syn isomer, 1.9 g.).

I.R. $\nu_{max}^{Nujol}$: 3250, 1790, 1740, 1700, 1660, 1610, 1530 cm$^{-1}$.

N.M.R. δ(DMSO-d$_6$, ppm): 3.92 (2H, q, J=17 Hz), 4.77 (2H, q, J=8.5 Hz), 5.35 (1H, d, J=5 Hz), 5.48 (2H, s), 5.95 (1H, dd, J=5 Hz, 8 Hz), 7.50 (1H, s), 7.70 (2H, d, J=9 Hz), 8.27 (2H, d, J=9 Hz), 8.53 (1H, s), 9.92 (1 Hz, d, J=8 Hz), 12.67 (1H, broad s).

(2) A suspension of 4-nitrobenzyl 7-[2-(2-formamidothiazol-4-yl)-2-(2,2,2-trifluoroethoxyimino)acetamido]-3-chloro-3-cephem-4-carboxylate (syn isomer, 1.8 g.) and 10% palladium carbon (0.9 g.) in methanol (20 ml.) and tetrahydrofuran (20 ml.) was treated in a similar manner to that of Example 21-(2) to give 7-[2-(2-formamidothiazol-4-yl)-2-(2,2,2-trifluoroethoxyimino)acetamido]-3-chloro-3-cephem-4-carboxylic acid (syn isomer, 1.0 g.).

I.R. $\nu_{max}^{Nujol}$: 3250, 1780, 1690, 1655, 1530 cm$^{-1}$.

N.M.R. δ(DMSO-d$_6$, ppm): 3.86 (2 H, q, J=17 Hz), 4.80 (2H, q, J=8.5 Hz), 5.33 (1H, d, J=5 Hz), 5.92 (1H, dd, J=5 Hz, 8 Hz), 7.53 (1H, s), 8.53 (1H, s), 9.93 (1H, d, J=8 Hz), 12.70 (1H, broad s).

(3) 7-[2-(2-Formamidothiazol-4-yl)-2-(2,2,2-trifluoroethoxyimino)acetamido]-3-chloro-3-cephem-4-carboxylic acid (syn isomer, 0.7 g.), conc.hydrochloric acid (0.43 ml.) and methanol (16 ml.) were treated in a similar manner to that of Example 21-(3) to give 7-[2-(2-aminothiazol-4-yl)-2-(2,2,2-trifluoroethoxyimino)acetamido]-3-chloro-3-cephem-4-carboxylic acid (syn isomer, 0.65 g.).

I.R. $\nu_{max}^{Nujol}$: 3320, 3150, 1775, 1720, 1660, 1645, 1600, 1545 cm$^{-1}$.

N.M.R. δ(DMSO-d$_6$, ppm): 3.87 (2H, q, J=18 Hz), 4.80 (2H, q, J=8.5 Hz), 5.30 (1H, d, J=5 Hz), 5.83 (1H, dd, J=5 Hz, 8 Hz), 7.05 (1H, s), 10.00 (1H, d, J=8 Hz).

EXAMPLE 34

(1) A solution of 2-(2-formamidothiazol-4-yl)-2-butoxyiminoacetic acid (syn isomer, 1.5 g.), N,N-dimethylformamide (440 mg.) and phosphoryl chloride (920 mg.) in ethyl acetate (12 ml.) and a solution of 4-nitrobenzyl 7-amino-3-chloro-3-cephem-4-carboxylate (2.03 g.), trimethylsilylacetamide (7 g.) and bis(trimethylsilyl)acetamide (2 ml.) in ethyl acetate (25 ml.) were treated in a similar manner to that of Example 21-(1) to give 4-nitrobenzyl 7-[2-(2-formamidothiazol-4-yl)-2-butoxyiminoacetamido]-3-chloro-3-cephem-4-carboxylate (syn isomer, 2.8 g.), yellow powder.

I.R. $\nu_{max}^{Nujol}$: 3200-3250, 1780, 1730, 1690, 1655, 1605, 1530, 1350 cm$^{-1}$.

N.M.R. δ(DMSO-d$_6$, ppm): 0.90 (3H, m), 1.2-1.6 (4H, m), 3.88 (2H, AB-q, J=19 Hz), 4.0-4.2 (2H, m), 5.32 (1H, d, J=4 Hz), 5.44 (2H, s), 5.92 (1H, d,d, J=4 Hz, 8 Hz), 7.36 (1H, s), 7.68 (2H, d, J=8 Hz), 8.22 (2H, d, J=8 Hz), 8.50 (1H, s), 9.72 (1H, d, J=8 Hz), 12.56 (1H, s).

(2) A mixture of 4-nitrobenzyl 7-[2-(2-formamidothiazol-4-yl)-2-butoxyiminoacetamido]-3-chloro-3-cephem-4-carboxylate (syn isomer, 2.7 g.), 10% palladium carbon (1.3 g.), water (4 ml.), acetic acid (0.4 ml.), methanol (27 ml.) and tetrahydrofuran (54 ml.) was treated in a similar manner to that of Example 21-(2) to give 7-[2-(2-formamidothiazol-4-yl)-2-butoxyiminoacetamido]-3-chloro-3-cephem-4-carboxylic acid (syn isomer, 1.4 g.), pale yellow powder.

I.R. $\nu_{max}^{Nujol}$: 3250, 2400-2600, 1780, 1700, 1690, 1650, 1610 cm$^{-1}$.

N.M.R. δ (DMSO-d$_6$, ppm): 0.90 (3H, m), 1.2-1.70 (4H, m), 3.88 (2H, ABq, J=19 Hz), 4.0-4.25 (2H, m), 5.32 (1H, d, J=5 Hz), 5.90 (1H, d,d, J=5 Hz, 9 Hz), 7.42 (1H, s), 8.50 (1H, s), 9.73 (1H, d, J=8 Hz), 12.60 (1H, s).

(3) A mixture of 7-[2-(2-formamidothiazol-4-yl)-2-butoxyiminoacetamido]-3-chloro-3-cephem-4-carboxylic acid (syn isomer, 1.3 g.), conc. hydrochloric acid (1.3 ml.) and methanol (20 ml.) was treated in a similar manner to that of Example 21-(3) to give 7-[2-(2-aminothiazol-4-yl)-2-butoxyiminoacetamido]-3-chloro-3-cephem-4-carboxylic acid (syn isomer, 1.2 g.), pale yellow powder.

I.R. $\nu_{max}^{Nujol}$: 3300, 2500–2600, 1785, 1730, 1655, 1630 cm$^{-1}$.

N.M.R. δ (DMSO-d$_6$, ppm): 0.90 (3H, m), 1.2–1.75 (4H, m), 3.88 (2H, AB-q, J=19 Hz), 5.17 (2H, m), 5.33 (1H, d, J=5 Hz), 5.83 (1H, d,d, J=5 Hz, 8 Hz), 6.93 (1H, s), 9.50 (2H, broad s), 9.85 (1H, d, J=8 Hz).

EXAMPLE 35

(1) A solution of 2-(2-formamidothiazol-4-yl)-2-butoxyiminoacetic acid (syn isomer, 1.09 g.), N,N-dimethylformamide (322 mg.) and phosphoryl chloride (675 mg.) in ethyl acetate (9.2 ml.) and a solution of 4-nitrobenzyl 7-amino-3-methoxy-3-cephem-4-carboxylate hydrochloride (1.5 g.), trimethylsilylacetamide (5 g.) and bis(trimethylsilyl)acetamide (2 ml.) in ethyl acetate (30 ml.) were treated in a similar manner to that of Example 3-(1) to give 4-nitrobenzyl 7-[2-(2-formamidothiazol-4-yl)-2-butoxyiminoacetamido]-3-methoxy-3-cephem-4-carboxylate (syn isomer, 1.8 g.).

I.R. $\nu_{max}^{Nujol}$: 3300, 3220, 1770, 1715, 1690, 1650, 1610, 1540, 1350 cm$^{-1}$.

N.M.R. δ (DMSO-d$_6$, ppm): 0.90 (3H, m), 1.2–1.7 (4H, m), 3.72 (2H, broad s), 3.96 (3H, s), 4.10 (2H, m), 5.22 (1H, d, J=4 Hz), 5.32 (2H, s), 5.75 (1H, d,d, J=4 Hz, 8 Hz), 7.43 (1H, s), 7.64 (2H, d, J=9 Hz), 8.20 (2H, d, J=9 Hz), 8.48 (1H, s), 9.56 (1H, d, J=8 Hz), 12.59 (1H, s).

(2) A mixture of 4-nitrobenzyl 7-[2-(2-formamidothiazol-4-yl)-2-butoxyiminoacetamido]-3-methoxy-3-cephem-4-carboxylate (syn isomer, 1.7 g.), 10% palladium carbon (1 g.), water (3 ml.), acetic acid (0.3 ml.), methanol (20 ml.) and tetrahydrofuran (35 ml.) was treated in a similar manner to that of Example 15-(2) to give 7-[2-(2-formamidothiazol-4-yl)-2-butoxyiminoacetamido]-3-methoxy-3-cephem-4-carboxylic acid (syn isomer, 1 g.), yellow powder.

I.R. $\nu_{max}^{Nujol}$: 3200–3250, 2600, 1775, 1700, 1690, 1650 cm$^{-1}$.

N.M.R. δ (DMSO-d$_6$, ppm): 1.0 (3H, m), 1.2–1.75 (4H, m), 3.67 (2H, broad s), 3.86 (3H, s), 4.0–4.3 (2H, m), 5.23 (1H, d, J=4 Hz), 5.68 (1H, d,d, J=4 Hz, 8 Hz), 7.50 (1H, s), 8.58 (1H, s), 9.63 (1H, d, J=8 Hz).

(3) A mixture of 7-[2-(2-formamidothiazol-4-yl)-2-butoxyiminoacetamido]-3-methoxy-3-cephem-4-carboxylioc acid (syn isomer, 0.9 g.), conc. hydrochloric acid (0.8 ml.) and methanol (13.5 ml.) was treated in a similar manner to that of Example 15-(3) to give 7-[2-(2-aminothiazol-4-yl)-2-butoxyiminoacetamido]-3-methoxy-3-cephem-4-carboxylic acid (syn isomer, 0.4 g.), yellowish white powder.

I.R. $\nu_{max}^{Nujol}$: 3200–3300, 2600, 1770, 1705, 1670, 1620 cm$^{-1}$.

N.M.R. δ (DMSO-d$_6$, ppm): 0.90 (3H, m), 1.2–1.65 (4H, m), 3.60 (2H, s), 3.96 (3H, s), 4.0–4.16 (2H, m), 5.12 (1H, d, J=4 Hz), 5.55 (1H, d,d, J=4 Hz, 8 Hz), 6.80 (1H, s), 7.2–7.6 (2H, broad s), 9.50 (1H, d, J=8 Hz).

EXAMPLE 36

(1) 4-Nitrobenzyl 7-amino-3-cephem-4-carboxylate (5 g.) was dissolved in a solution of trimethylsilylacetamide (13.8 g.) and bis(trimethylsilyl)acetamide (10 ml.) in dry ethyl acetate (50 ml.) and stirred at 45° C. for 1.5 hours. A solution of bromine (2.88 g.) in methylene chloride (7 ml.) was added dropwise to a solution of diketene (1.5 g.) in methylene chloride (7 ml.) at −40° C. over 20 minutes and stirred at −30° C. for 1 hour. The solution obtained thus was added to dropwise to the above solution of 4-nitrobenzyl 7-amino-3-cephem-4-carboxylate under cooling at −15° C. and then stirred at the same temperature for 30 minutes. Water (50 ml.) was added to the resultant solution and extracted with ethyl acetate. The ethyl acetate extract was washed with water, dried over magnesium sulfate and concentrated under reduced pressure to give oily 4-nitrobenzyl 7-[2-(2-bromoacetyl)acetamido]-3-cephem-4-carboxylate (6.15 g.)

I.R. $\nu_{max}^{Nujol}$: 1780, 1740, 1630 cm$^{-1}$.

N.M.R. δ ppm (DMSO-d$_6$): 3.62 (2H, broad s), 4.37 (2H, s), 5.08 (1H, d, J=5 Hz), 5.40 (2H, s), 5.77–6.05 (m), 6.67 (1H, t, J=5 Hz), 7.68, 8.04 (4H, m, J=9 Hz), 9.07 (1H, d, J=8 Hz).

(2) 4-Nitrobenzyl 7-[2-(2-bromoacetyl)acetamido]-3-cephem-4-carboxylate (8.40 g.) was suspended in a mixture of tetrahydrofuran (150 ml.) and water (30 ml.) To the suspension were added acetic acid (50 ml.) and a solution of sodium nitrite (1.20 g.) in water (15 ml.) under ice-cooling, and stirred at 20° to 22° C. for 1.5 hours. The resultant solution was poured into ice-water (300 ml.) and stirred for 20 minutes. The precipitating substance was collected by filtration, washed with water, dried and then recrystallized from ethyl acetate to give 4-nitrobenzyl 7-[2-(2-bromoacetyl)-2-hydroxyiminoacetamido]-3-cephem-4-carboxylate (syn-isomer: 3.1 g.), mp 153° to 162° C.

I.R. $\nu_{max}^{Nujol}$: 3250, 1780, 1720, 1705, 1650, 1610, 1600 (shoulder), 1550, 1520 cm$^{-1}$.

N.M.R. δ ppm (DMSO-d$_6$): 3.67 (2H, d, J=4 Hz), 4.63 (1.5H, s), 4.88 (0.5H, s), 5.18 (1H, d, J=5 Hz), 5.45 (2H, s), 5.93 (1H, dd, J=5 Hz, 8 Hz, 6.72 (1H, t, J=4 Hz), 7.73 (2H, d, J=9 Hz), 8.28 (2H, d, J=9 Hz), 9.38 (1H, d, J=8 Hz), 11.27 (1H, s).

(3) A solution of diazomethane in diethyl ether was added little by little to a solution of 4-nitrobenzyl 7-[2-(2-bromoacetyl)-2-hydroxyiminoacetamido]-3-cephem-4-carboxylate (0.9 g.) in tetrahydrofuran (30 ml.) under ice-cooling until the reaction terminated, and then acetic acid was added to the resultant solution to decompose excess diazomethane. The resultant solution was concentrated under reduced pressure to give the foamy product of 4-nitrobenzyl 7-[2-(2-bromoacetyl)-2-methoxyiminoacetamido]-3-cephem-4-carboxylate (syn-isomer: 0.9 g.).

(4) Thiourea (0.14 g.) was added to a solution of 4-nitrobenzyl 7-[2-(2-bromoacetyl)-2-methoxyiminoacetamido]-3-cephem-4-carboxylate (syn-isomer: 0.8 g.) in ethanol (20 ml.) and water (5 ml.), and stirred at room temperature for 3.5 hours. The resultant solution was concentrated under reduced pressure, and to the residue were added water and ethyl acetate. The ethyl acetate layer was separated, washed with water, dried over magnesium sulfate and concentrated under reduced pressure to give the crude product (0.6 g.). The product was purified by column chromatography on silica gel (eluent:benzene and ethyl acetate (8:2) to give 4-nitrobenzyl 7-[2-(2-amino-4-thiazolyl)-2-methoxyiminoacetamido]-3-cephem-4-carboxylate (syn-isomer:0.21 g.), mp 165° to 170° C. (dec.).

I.R. $\nu_{max}^{Nujol}$:3350–3200, 1770, 1720, 1665, 1615, 1515 cm$^{-1}$.

N.M.R. δ ppm (DMSO-d$_6$):3.60 (2H, broad s), 3.81 (3H, s), 5.12 (1H, d, J=5 Hz), 5.36 (2H, s), 5.83 (1H, dd, J=5 Hz, 8 Hz), 6.64 (1H, t, J=4 Hz), 6.70 (1H, s), 7.20 (2H, s), 7.65 (2H, d, J=9 Hz), 8.19 (2H, d, J=9 Hz, 9.60 (1H, d, J=8 Hz).

EXAMPLE 37

(1) A solution of bromine (43.0 g.) in methylene chloride (30 ml.) was dropwise added to a solution of diketene (22.6 g.) in methylene chloride (30 ml.) at −30° C. over 35 minutes, and stirred at the same temperature for 30 minutes. The solution was dropwise added to a stirred solution of 4-nitrobenzyl 7-amino-3-cephem-4-carboxylate (75.1 g.) and bis(trimethylsilyl)acetamide (68.4 g,) in tetrahydrofuran (1.5 l) at −15° C. over 10 minutes, and the solution was stirred at the same temperature for 50 minutes. Water (35 ml.) and an aqueous solution (35 ml.) of sodium nitrite (18.6 g.) were added to the resultant solution while keeping at pH 2.0, and the solution was stirred at 10° to 15° C. for 15 minutes. After the solution was adjusted to pH 4.5 with a saturated aqueous solution of sodium bicarbonate, an aqueous solution (150 ml.) of thiourea (17.1 g.) was added to the solution, adjusted to pH 6.0 with a saturated aqeuous solution of sodium bicarbonate, and stirred for 20 minutes. The organic layer was separated and concentrated under reduced pressure. The residue was dissolved in ethyl acetate (1.5 l), and washed with water three times. The solution was dried over magnesium sulfate, treated with activated charcoal and concentrated under reduced pressure. After the residue was triturated with diethyl ether (200 ml.), the precipitates were collected by decantation and washed with ether acetate (300 ml.), a mixture of tetrahydrofuran (500 ml.) and ethyl acetate (1 l) at 60° C. and then with ethyl acetate (100 ml.) three times, and dried to give 4-nitrobenzyl 7-[2-(2-amino-4-thiazolyl)-2-hydroxyiminoacetamido]-3-cephem-4-carboxylate (syn isomer, 55.5 g.).

I.R. $\nu_{max}^{Nujol}$:1760, 1710, 1660, 1630 cm$^{-1}$.

N.M.R. δ ppm (DMSO-d$_6$):3.60 (2H, d, J=5 Hz), 5.12 (1H, d, J=5 Hz), 5.39(2H, s), 5.88 (1H, dd, J=8 Hz, 5 Hz), 6.63 (1H, s), 6.53–6.77 (1H, m), 7.08 (2H, broad s), 7.68 (2H, d, J=9 Hz), 8.22 (2H, d, J=9 Hz), 9.47 (1H, d, J=8 Hz), 11.33 (1H, s).

(2) 10% Palladium carbon (0.35 g.) was added to a solution of 4-nitrobenzyl 7-[2-(2-amino-4-thiazolyl)-2-hydroxyiminoacetamido]-3-cephem-4-carboxylate (syn-isomer:0.7 g.) in methanol (70 ml.), and the mixture was subjected to catalytic reduction at room temperature under atmospheric pressure for 1.5 hours. The resultant mixture was filtered, and the filtrate was concentrated under reduced pressure. To the residue was added an aqueous solution of sodium bicarbonate and the insoluble substance was filtered out. The filtrate was washed with ethyl acetate and methylene chloride in turn, bubbled with nitrogen gas and then lyophilized. The residue was dissolved in water (30 ml.) and adjusted to pH 3.8 with 10% hydrochloric acid. The solution was subjected to column chromatography on macroporous, non-ionic adsorption resin "Diaion HP-20" (Trade mark; manufactured by Mitsubishi Chemical Industries Ltd.; 20 ml.) washed with water, and then eluted with 40% aqueous acetone. After acetone was removed from the eluate under reduced pressure, the residue was lyophilized to give 7-[2-(2-amino-4-thiazolyl)-2-hydroxyiminoacetamido]-3-cephem-4-carboxylic acid (syn-isomer:0.25 g.).

I.R. $\nu_{max}^{Nujol}$:3350 to 3200, 1770, 1670, 1630 cm$^{-1}$.

N.M.R. δ ppm (DMSO-d$_6$):3.60 (2H, broad s), 5.10 (1H, d, J=5 Hz), 5.83 (1H, dd, J=5 Hz, 8 Hz), 6.47 (1H, t, J=4 Hz), 6.67 (1H, s), 9.47 (1H, d, J=8 Hz).

EXAMPLE 38

(1) Thiourea (0.18 g.) was added to a suspension of 4-nitrobenzyl 7-[2-(2-bromoacetyl-2-hydroxyiminoacetamido]-3-cephem-4-carboxylate (syn-isomer:1.05 g.) in ethanol (25 ml.), tetrahydrofuran (25 ml.) and water (5 ml.), and stirred at room temperature for 4 hours. The resultant solution was concentrated under reduced pressure and cooled. The residue was crystallized by treating with a mixture of tetrahydrofuran and ethyl acetate, and collected by filtration to give 4-nitrobenzyl 7-[2-(2-amino-4-thiazolyl)-2-hydroxyiminoacetamido]-3-cephem-4-carboxylate (syn-isomer:0.95 g.), colorless crystals, mp 172° to 175° C. (dec.)

I.R. $\nu_{max}^{Nujol}$:3350–3200, 1770, 1725, 1670, 1625, 1520 cm$^{-1}$.

N.M.R . δ ppm (DMSO-d$_6$):3.68 (2H, d, J=4 Hz), 5.20 (1H, d, J=5 Hz), 5.43 (2H, s), 5.90 (1H, dd, J=8 Hz, 5 Hz), 6.70 (1H, t, J=4 Hz), 6.88 (1H, s), 7.70 (2H, d, J=9 Hz), 8.23 (2H, d, J=9 Hz), 9.68 (1H, d, J=8 Hz).

(2) A solution of diazomethane in diethyl ether was added little by little to a solution of 4-nitrobenzyl 7-[2-(2-amino-4-thiazolyl)-2-hydroxyiminoacetamido]-3-cephem-4-carboxylate (syn-isomer:0.3 g.) in methanol (30 ml.) until the reaction terminated. The resultant solution was concentrated under reduced pressure, and the residue was pulverized with diethyl ether, collected by filtration and dried to give 4-nitrobenzyl 7-[2-(2-amino-4-thiazolyl)-2-methoxyiminoacetamido[-3-cephem-4-carboxylate (syn-isomer:0.26 g.). This product was identified with the authentic sample.

EXAMPLE 39

7-Amino-3-cephem-4-carboxylic acid (2.54 g.) was dissolved in a solution of trimethylsilylacetamide (11.7 g.) and bis(trimethylsilyl)acetamide (15 ml.) in dried ethyl acetate (50 ml.) A solution of bromine (2.43 g.) in dried methylene chloride (10 ml.) was added dropwise to a solution of diketene (1.28 g.) in dried methylene chloride (25 ml.) at −30° C. over 10 minutes and stirred at the same temperature for 1.5 hours. The solution was added to the above solution containing 7-amino-3-cephem-4-carboxylic acid at −15° C. over 10 minutes, and stirred at −15° to −10° C. for 1.5 hours. Water (50 ml.) was added to the resultant solution. The ethyl acetate layer was separated, and extracted with aqueous solution of sodium bicarbonate. The aqueous extract was adjusted to pH 2.0 with 10% hydrochloric acid and extracted with ethyl acetate. The ethyl acetate extract was washed with water, dried over magnesium sulfate and concentrated under reduced pressure to give 7-[2-(2-bromoacetyl)acetamido]-3-cephem-4-carboxylic acid (2.82 g.)

I.R. $\nu_{max}^{Nujol}$: 1760, 1660 cm$^{-1}$.

N.M.R. δ ppm (DMSO-d$_6$):3.58 (2H, d, J=4 Hz), 3.65 (2H, s), 4.40 (2H, s), 5.06 (1H, d, J=5 Hz), 5.73 (1H, dd, J=8 Hz, 5 Hz), 6.50 (1H, t, J=4 Hz), 9.08 (1H, d, J=8 Hz).

EXAMPLE 40

The following compounds can be prepared in a similar manner to that of Example 36.

(1) 4-Nitrobenzyl 7-[2-(2-aminothiazol-4-yl)-2-ethoxyimino-acetamido]-3-cephem-4-carboxylate (syn isomer)

(2) 4-Nitrobenzyl 7-[2-(2-aminothiazol-4-yl)-2-propoxyimino-acetamido]-3-cephem-4-carboxylate (syn isomer)

(3) 4Nitrobenzyl 7-[2-(2-aminothiazol-4-yl)-2-isopropoxy-iminoacetamido]-3-cephem-4-carboxylate (syn isomer)

EXAMPLE 41

The following compounds can be prepared in a similar manner to that of Example 38- (2).

(1) 4-Nitrobenzyl 7-[2-(2-aminothiazol-4-yl)-2-ethoxyimino-acetamido]-3-cephem-4-carboxylate (syn isomer)

(2) 4-Nitrobenzyl 7-[2-(2-aminothiazol-4-yl)-2-propoxyimino-acetamido]-3-cephem-4-carboxylate (syn isomer)

(3) 4-Nitrobenzyl 7-[2-(2-aminothiazol-4-yl)-2-isopropoxyimino-acetamido]-3-cephem-4-carboxylate (syn isomer)

EXAMPLE 42

(1) Sodium boron hydride (160 mg.) was added to a suspension of 4-nitrobenzyl 7-[2-(2-formamido-4-thiazolyl)-2-methoxyiminoacetamido]-3-hydroxy-3-cephem-4-carboxylate (syn isomer, 1 g.) in tetrahydrofuran (10 ml.), acetic acid (3 ml.) and water (1 ml.) at 0° C. over 10 minutes, and stirred at 0° to 3° C. for 55 minutes. After water was added to the resultant solution, the solution was extracted with ethyl acetate. The extract was washed with a saturated aqueous solution of sodium chloride, a saturated aqueous solution of sodium bicarbonate and a saturated aqueous solution of sodium chloride in turn, and dried over magnesium sulfate. The solution was concentrated under reduced pressure, and the residue was pulverized with diethyl ether to give 4-nitrobenzyl 7-[2-(2-formamido-4-thiazolyl)-2-methoxyiminoacetamido]-3-hydroxycepham-4-carboxylate (syn isomer, 0.77 g.), mp 172° to 175° C. (dec.).

I.R. $\nu_{max}^{Nujol}$: 3250, 1775, 1745, 1660 cm$^{-1}$.

N.M.R. δ ppm (DMSO-d$_6$):2.76 (1H, dd, J=14 Hz, 3Hz), 3.17 (1H, dd, J=14 Hz, 13 Hz),3.92 (3H, s), 4.03 (1H, m), 4.72 (1H, d, J=6 Hz), 5.24 (1H, d, J=4 Hz), 5.37 (2H, s), 5.56 (1H, dd, J=9 Hz, 4 Hz), 6.07 (1H, d, J=4 Hz), 7.44 (1H, s), 7.72 (2H, d, J=8 Hz), 8.27 (2H, d, J=8 Hz), 8.54 (1H, s), 9.67 (1H, d, J=9 Hz).

(2) Mesyl chloride (0.406 g.) was dropwise added to a stirred mixture of 4-nitrobenzyl 7-[2-(2-formamido-4-thiazolyl)-2-methoxyiminoacetamido]-3-hydroxycepham-4-carboxylate (syn isomer, 1 g.), N,N-dimethylformamide (10 ml.) and potassium carbonate (0.732 g.) at 0° to 5° C. over 2 minutes, and the solution was stirred at room temperature for 2.5 hours. After ethyl acetate and water were added to the resultant solution, the solution was extracted with ethyl acetate. The remaining aqueous layer was extracted again with ethyl acetate. The ethyl acetate extract solution was washed with a saturated aqueous solution of sodium chloride, dried over magnesium sulfate, and concentrated under reduced pressure. The residue was subjected to column chromatography on silica gel (30 g.) and eluted with a mixture of chloroform and ethyl acetate. The eluate was concentrated under reduced pressure to give 4-nitrobenzyl 7-[2-(2-formamido-4-thiazolyl)-2-methoxyiminoacetamido]-3-cephem-4-carboxylate (syn isomer, 0.12 g.), mp 224° C. (dec.).

EXAMPLE 43

Phosphoryl chloride (704 mg.) was added dropwise to a solution of N,N-dimethylformamide (336 mg.) in ethyl acetate (8 ml.) below 5° C. and stirred at the same temperature for 30 minutes. 2-(2-Formamidothiazol-4-yl)-2-methoxyiminoacetic acid (syn isomer, 1 g.) was added to the solution and stirred at 5° to 10° C. for an hour. The solution was added dropwise to a solution of 7-amino-3-hydroxycepham-4-carboxylic acid (872 mg.) and trimethylsilylacetamide (1.05 g.) in ethyl acetate (20 ml.) at −20° C. over 5 minutes, and stirred at −20° to −25° C. for an hour. Water (50 ml.) was added to the resultant solution and adjusted to pH 7.0 with sodium bicarbonate. The aqueous layer was separated, and the ethyl acetate layer was extracted again with water (10 ml.). The aqueous extracts were combined, adjusted to pH 6 and absorbed on macroporous nonionic adsorption resin Diaion HP-20 (50 ml., Trademark, manufactured by Mitsubishi Chemical Industries). The column was washed with water (50 ml.) and eluted with 30% aqueous isopropyl alcohol. The eluate containing the object compound was adjusted to pH 6.5 and concentrated under reduced pressure. The residue was lyophilized to give sodium 7-[2-(2-formamidothiazol-4-yl)-2-methoxyiminoacetamido]-3-hydroxycepham-4-carboxylate (syn isomer, 1.1 g.).

N.M.R. δ D$_2$O, ppm): 2.72–3.18 (2H, m), 4.02 (3H, s), 4.02–4.28 (1H, m), 4.54 (1H, d, J=4 Hz), 5.28 (1H, d, J=4 Hz), 5.53 (1H, d, J=4 Hz), 7.50 (1H, s), 8.53 (1H, s).

EXAMPLE 44

Thionyl chloride (0.423 g.) was dropwise added to a stirred solution of 4-nitrobenzyl 7-[2-(2-formamido-4-thiazolyl)-2-methoxyiminoacetamido]-3-hydroxy-3-cephem-4-carboxylate (syn isomer, 1 g.) in N,N-dimethylformamide (10 ml.) under ice cooling over 2 minutes, and the solution was stirred at room temperature for 1.1 hours. Ethyl acetate (40 ml.) and water (30 ml.) were added to the resultant solution and shaken sufficiently. The aqueous layer was extracted with ethyl acetate, and the extract was combined with the ethyl acetate layer separated above. The ethyl acetate solution was washed with a saturated aqueous solution of sodium chloride, dried over magnesium sulfate and then concentrated under reduced pressure. The residue was subjected to column chromatography on silica gel (30 g.) and eluted with chloroform and then a mixture of chloroform and ethyl acetate (7:3). The latter eluate was concentrated under reduced pressure to give 4-nitrobenzyl 7-[2-(2-formamido-4-thiazolyl)-2-methoxyiminoacetamido]-3-chloro-3-cephem-4-carboxylate (syn isomer, 0.2 g.), mp 216° C. (dec.).

I.R. $\nu_{max}^{Nujol}$: 3230 (shoulder), 3110, 3050, 1785, 1725, 1690, 1655 cm$^{-1}$.

N.M.R. δ ppm (DMSO-d$_6$): 3.93 (3H, s), 3.93 (2H, q, J=18 Hz), 5.36 (1H, d, J=5 Hz), 5.50 (2H, s), 5.97 (1H, dd, J=5 Hz, 9 Hz), 7.45 (1H, z), 7.73 (2H, d, J=9 Hz), 8.29 (2H, d, J=9 Hz), 8.56 (1H, s), 9.78 (1H, d, J=9 Hz).

EXAMPLE 45

The following compounds can be prepared in a similar manner to that of Example 44.

(1) 4-Nitrobenzyl 7-[2-(2-formamidothiazol-4-yl)-2-propoxyiminoacetamido]-3-chloro-3-cephem-4-carboxylate (syn isomer)

(2) 4-Nitrobenzyl 7-[2-(2-formamidothiazol-4-yl)-2-(2,2,2-trifluoroethoxyimino)acetamido]-3-chloro-3-cephem-4-carboxylate (syn isomer)
(3) 4-Nitrobenzyl 7-[2-(2-formamidothiazol-4-yl)-2-butoxyiminoacetamido]-3-chloro-3-cephem-4-carboxylate (syn isomer)

EXAMPLE 46

Fermentation:
Pre-culture medium: Trypticase soy broth (BBL)
Main culture medium:
  glycerin: 3 g
  peptone: 1 g
  corn steep liquor: 1 g
  dry yeast: 2 g
  sodium carbonate: 0.1 g
  $KH_2PO_4$: 0.55 g
  $Na_2HPO_4 \cdot 12H_2O$: 2.15 g
(The above components were dissolved in water so as to become 100 ml in total, and the medium was adjusted to pH 7.2.)

A main culture broth (100 ml.) was placed in Sakaguchi-flask (500 ml) and sterilized at 120° C. for 20 minutes. Into this medium, there was inoculated a culture broth (1 ml.) of each of microorganisms as given below, which were cultured in a pre-culture medium, respectively.

Reaction:
Into above cultured broth, there was added the Substrate (0.1 g) as given below suspended in 0.1 M phosphate buffer (pH 7.2, 1 ml.), and then the mixture was shaken at 30° C. for 48 hours.

Identification and assay:
After the reaction, in order to identify the generated product the reaction mixture as obtained above was chromatographed on Eastman chromatogram 6065 cellulose at room temperature. As a developing agent, there was used (A) the upper layer of a mixture of n-butanol, ethanol and water (4:1:5 by volume) and (B) a mixture of n-propanol and water (7:3 by volume). Rf value was determined by index of antimicrobial activity against a sensitive strain of Escherichia coli ES 111, and as the result only one spot showing each of Product I and II was observed on the Eastman chromatogram 6065 cellulose without showing any spot of each of Substrate I and II. Rf value are shown in the following table.

|  | Developping Solvent | |
| --- | --- | --- |
|  | A | B |
| Reaction Mixture (Product I) | 0.85 | 0.90 |
| Reference (Substrate I) | 0.39 | 0.60 |
| Reaction Mixture (Product II) | 0.90 | 0.92 |
| Reference (Substrate II) | 0.36 | 0.54 |

16 Note:
Substrate I: 4-nitrobenzyl 7-[2-formamido-4-thiazolyl)-2-methoxyiminoacetamido]-3-cephem-4-carboxylate (syn isomer)
Product I: 7-[2-(2-formamido-4-thiazolyl)-2-methoxyimino-acetamido]-3-cephem-4-carboxylic acid (syn isomer)
Substrate II: 4-nitrobenzyl 7-[2-amino-4-thiazolyl)-2-methoxyiminoacetamido]-3-cephem-4-carboxylate (syn isomer)
Product II: 7-[2-(2-amino-4-thiazolyl)-2-methoxyimino-acetamido]-3-cephem-4-carboxylic acid (syn isomer)

The product generated in the reaction mixture as obtained above was assayed by paper disk-plate method using a sensitive strain of Escherichia coli ES 111 (culture: 37° C., 16 hours) and the yield thereof was calculated. The results are shown in the following.

| Microorganism used for enzymatic hydrolysis | Yield (%) | |
| --- | --- | --- |
|  | Product I | Product II |
| Bacillus subtilis IAM 1069 | 75 | 60 |
| Bacillus sphaericus IAM 1286 | 75 | 20 |
| Bacillus subtilis IAM 1107 | 75 | 95 |
| Bacillus subtilis IAM 1214 | 85 | 20 |
| Corynebacterium equi IAM 1038 | 95 | 95 |
| Micrococcus varians IAM 1314 | 70 | 20 |
| Flavobacterium rigens IAM 1238 | 85 | 90 |
| Salmonella typhimurium IAM 1406 | 90 | 20 |
| Staphylococcus epidermidis IAM 1296 | 90 | 95 |
| Microbacterium flavum IAM 1642 | 90 | 95 |

The following are examples of pharmaceutical compositions prepared in accordance with this invention and containing 7-[2-(2-amino-4-thiazolyl)-2-methoxyiminoacetamido]-3-cephem-4-carboxylic acid (syn isomer, Compound A) as the active substance.

EXAMPLE 47 (lyophlized preparation for injection)

Sodium salt of compound A (20 g. potency) was dissolved in water (200 ml.), and the solution (5 ml.) was filled in each 10 ml. vial. These vials are frozen and dried in a vacuum (lyophilization).

EXAMPLE 48 (suspension for injection)

Compound A: 25 g.
Methyl cellurose: 0.5 g.
Methyl 4-oxobenzoate: 0.1 g.
Polysolvate 80: 0.1 g.
Lidocaine hydrochloride: 0.5 g.
Water for injection to make 100 ml.

This aqueous suspension is suitable for intramuscular injection.

EXAMPLE 49 (tablets for oral use)

Compound A: 500 mg.
Lactose: 375.5 mg.
Hydroxypropylcellurose: 2 mg.
Magnesium stearate: 22.5 mg.

This mixture provides a tablet for oral use in the treatment of infectious diseases caused by pathogenic bacteria.

EXAMPLE 50 (capsule for oral use)

Compound A: 500 mg.
Magnesium stearate: 10 mg.

This mixture provides a capsule for oral use in the treatment of infectious diseases caused by pathogenic bacteria.

EXAMPLE 51

(1) A solution of 2-(2-formamidothiazol-4-yl)-2-n-hexyloxyiminoacetic acid (syn isomer, 3.24 g.), N,N-dimethylformamide (0.951 g.), and phosphoryl chloride (2.00 g.) in ethyl acetate (20 ml.), and a solution of 4-nitrobenzyl 7-amino-3-chloro-3-cephem-4-carboxylate hydrochloride (4 g.) in a mixture of acetone (20 ml.), water (20 ml.) and tetrahydrofuran (400 ml.) were treated in a similar manner to that of Example 21-(1) to give 4-nitrobenzyl 7-[2-(2-formamidothiazol-4-yl)-2-n-hexyloxyiminoacetamido]-3-chloro-3-cephem-4-carboxylate (syn isomer, 5.78 g.).

I.R. $\nu_{max}^{Nujol}$: 3240, 3200, 3050, 1780, 1730, 1695, 1660 cm$^{-1}$.

N.M.R. δ (DMSO-d$_6$, ppm): 0.6~2.1 (11H, m), 3.96 (2H, q, J=19 Hz), 4.15 (2H, t, J=6 Hz), 5.37 (1H, d, J=5 Hz), 5.50 (2H, s), 5.97 (1H, d, d, J=5 Hz, 8 Hz), 7.42 (1H, s), 7.72 (2H, d, J=9 Hz), 8.28 (2H, d, J=9 Hz), 8.54 (1H, s), 9.74 (1H, d, J=8 Hz), 12.73 (1H, broad s).

(2) A mixture of 4-nitrobenzyl 7-[2-(2-formamidothiazol-4-yl)-2-n-hexyloxyiminoacetamido]-3-chloro-3-cephem-4-carboxylate (syn isomer, 5.6 g.), acetic acid (0.4 ml.), 10% palladium carbon (2.24 g.), water (4 ml.), methanol (23 ml.) and tetrahydrofuran (56 ml.) was treated in a similar manner to that of Example 21-(2) to give 7-[2-(2-formamidothiazol-4-yl)-2-n-hexyloxyiminoacetamido]-3-chloro-3-cephem-4-carboxylic acid (syn isomer, 2.5 g.).

I.R. $\nu_{max}^{Nujol}$: 3225, 1785, 1690, 1650 cm$^{-1}$.

N.M.R. δ (DMSO-d$_6$, ppm): 0.6~2.0 (11H, m), 3.86 (2H, q, J=18 Hz), 4.13 (2H, t, J=6 Hz), 5.30 (1H, d, J=5 Hz), 5.88 (1H, d, d, H=5 Hz, 8 Hz), 7.41 (1H, s), 8.54 (1H, s), 9.70 (1H, d, J=8 Hz), 12.68 (1H, s).

(3) A mixture of 7-[2-(2-formamidothiazol-4-yl)-2-n-hexyloxyiminoacetamido]-3-chloro-3-cephem-4-carboxylic acid (syn isomer, 2.4 g.), conc. hydrochloric acid (1.84 g.), methanol (36 ml.) and tetrahydrofuran (30 ml.) was stirred at 30° C. for 2 hours. The resultant solution was concentrated in vacuo. Water (60 ml.) was added to the residue and the precipitates were collected by filtration, washed with water and dried over phosphorus pentoxide to give 7-[2-(2-aminothiazol-4-yl)-2-n-hexyloxyiminoacetamido]-3-chloro-3-cephem-4-carboxylic acid (syn isomer, 1.86 g.).

I.R. $\nu_{max}^{Nujol}$: 3300, 1780, 1665, 1535 cm$^{-1}$.

N.M.R. δ (DMSO-d$_6$, ppm): 0.6~2.0 (11H, m), 3.84 (2H, q, J=18 Hz), 4.08 (2H, t, J=7 Hz), 5.28 (1H, d, J=5 Hz), 5.82 (1H, d, d, J=5 Hz, 8 Hz), 6.77 (1H, s), 9.66 (1H, d, J=8 Hz), 6.0~8.0 (2H, broad s).

EXAMPLE 52

(1) 2-(2-Formamidothiazol-4-yl)-2-propargyloxyiminoacetic acid (syn isomer, 1.27 g.), N,N-dimethylformamide (402 mg.), phosphoryl chloride (843 mg.) and ethyl acetate (11.2 ml.) were treated in a conventional manner to prepare an activated acid solution. On the other hand, a mixture of 7-amino-3-methoxy-3-cephem-4-carboxylic acid hydrochloride (1.33 g.), trimethylsilylacetamide (4 g.), bis(trimethylsilyl)acetamide (2 ml.) and ethyl acetate (20 ml.) was stirred at 40° to 45° C. for an hour. To the solution was added the activated acid solution obtained above all at once at −15° C., and then stirred at −5° to −10° C. for 1.5 hours. Water (30 ml.) was added to the resultant solution, filtered and the organic layer was separated. The insoluble substance filtered out was dissolved in a saturated aqueous solution of sodium bicarbonate, and the solution was added to the organic layer. The solution was adjusted to pH 7.5 and the aqueous solution was separated, and then extracted with ethyl acetate of pH 2.0. The extract was washed with water, dried over magnesium sulfate and filtered. The filtrate was concentrated in vacuo to give 7-[2-(2-formamidothiazol-4-yl)-2-propargyloxyiminoacetamido]-3-methoxy-3-cephem-4-carboxylic acid (syn isomer, 1.0 g.), yellow powder.

I.R. $\nu_{max}^{Nujol}$: 3200~3300, 2500~2600, 2120, 1770, 1710, 1690, 1670 cm$^{-1}$.

N.M.R. δ (DMSO-d$_6$, ppm): 3.50 (1H, m), 3.65 (2H, s), 3.82 (3H, s), 4.80 (2H, d, J=2 Hz), 5.20 (1H, d, J=4 Hz), 5.62 (1H, d,d, J=4 Hz, 8 Hz), 7.52 (1H, s), 8.55 (1H, s), 9.68 (1H, d, J=8 Hz), 12.65 (1H, broad s).

(2) A mixture of 7[2-(2-formamidothiazol-4-yl)-2-propargyloxyiminoacetamido]-3-methoxy-3-cephem-4-carboxylic acid (syn isomer, 0.9 g.), conc. hydrochloric acid (0.9 ml.) and methanol (13.5 ml.) was stirred at room temperature for 4 hours. After concentrating the resultant solution in vacuo at 35° C., the residue was dissolved in water and washed with ethyl acetate. The aqueous solution was adjusted to pH 7.0 with sodium bicarbonate and washed with ethyl acetate and diethyl ether. After removing the organic solvent by bubbling nitrogen gas, the solution was adjusted to pH 3.0 with 10% hydrochloric acid and stirred under ice cooling. The precipitates were collected by filtration, washed with water and dried to give 7-[2-(2-aminothiazol-4-yl)-2-proparglyoxyiminoacetamido]-3-methoxy-3-cephem-4-carboxylic acid (syn isomer, 0.25 g.), whitish yellow powder.

I.R. $\nu_{max}^{Nujol}$: 3300, 2500~2600, 2120, 1775, 1710, 1670, 1620 cm$^{-1}$.

N.M.R. δ (DMSO-d$_6$, ppm): 3.52 (1H, m), 3.82 (3H, s), 4.77 (2H, d, J=2 Hz), 5.17 (1H, d, J=4 Hz), 5.58 (1H, d,d, J=4 Hz, 8 Hz), 6.93 (1H, s), 7.1~7.3 (2H, broad s), 9.67 (1H, d, J=8 Hz).

EXAMPLE 53

(1) 2-(2-Formamidothiazol-4-yl)-2-propargyloxyiminoacetic acid (syn isomer, 1.27 g.), N,N-dimethylformamide (400 mg.), phosphoryl chloride (850 mg.) and ethyl acetate (11.2 ml.) were treated in a conventional manner to give the activated acid solution. The activated acid solution was added to a solution of 7-amino-3-chloro-3-cephem-4-carboxylic acid hydrochloride (2 g.), trimethylsilylacetamide (6 g.) and bis(trimethylsilyl)acetamide (3 ml.) in ethyl acetate (40 ml.) at −15° C. all at once, and stirred at −5° to −10° C. for 1.5 hours. After adding water (30 ml.) to the resultant solution, the ethyl acetate layer was separated and extracted with a saturated aqueous solution of sodium bicarbonate. Ethyl acetate was added to the aqueous extract, adjusted to pH 2.0 with 10% hydrochloric acid. The ethyl acetate layer was separated, washed with water, dried over magnesium sulfate and filtered. The filtrate was concentrated in vacuo, and the residue was crystallized with a mixture of ethyl acetate and diisopropyl ether. The precipitates were collected by filtration and dried to give 7-[2-(2-formamidothiazol-4-yl)-2-propargyloxyiminoacetamido]-3-chloro-3-cephem-4-carboxylic acid (syn isomer, 1.5 g.), yellow powder.

I.R. $\nu_{max}^{Nujol}$: 3250~3300, 2500~2600, 2120, 1780, 1725, 1690, 1670 cm$^{-1}$.

N.M.R. δ (DMSO-d$_6$, ppm): 3.45 (1H, m), 3.57 (2H, AB-q, J=20 Hz), 4.77 (2H, d, J=2 Hz), 5.28 (1H, d, J=4 Hz), 5.80 (1H, d,d, J=4 Hz, 8 Hz), 8.42 (1H, s), 8.52 (1H, s), 9.78 (1H, d, J=8 Hz), 12.72 (1H, broad s).

(2) A mixture of 7-[2-(2-formamidothiazol-4-yl)-2-propargyloxyiminoacetamido]-3-chloro-3-cephem-4-carboxylic acid (syn isomer, 1.4 g.), conc. hydrochloric acid (1.4 ml.) and methanol (20 ml.) was treated in a similar manner to that of Example 51-(2) to give 7-[2-(2-aminothiazol-4-yl)-2-propargyloxyiminoacetamido]-3-chloro-3-cephem-4-carboxylic acid (syn isomer, 0.7 g.), yellowish white powder.

I.R. $\nu_{max}^{Nujol}$: 3350, 2500~2600, 2130, 1775, 1710, 1670, 1630 cm$^{-1}$.

N.M.R. δ (DMSO-d$_6$, ppm): 4.38 (1H, m), 4.48 (2H, AB-q, J=19 Hz), 4.72 (2H, d, J=2 Hz), 5.28 (1H, d, J=4 Hz), 5.80 (1H, d,d, J=4 Hz, 8 Hz), 6.78 (1H, s), 9.73 (1H, d, J=8 Hz).

EXAMPLE 54

Thiourea (11 mg.) and a solution of 7-[2-(2-bromoacetyl)-2-methoxyiminoacetamido]-3-cephem-4-carboxylic acid (syn isomer, 30 mg.) in ethanol (2 ml.) were treated in a similar manner to that of Example 36-(4) to give 7-[2-(2-amino-4-thiazolyl)-2-methoxyiminoacetamido]-3-cephem-4-carboxylic acid (syn isomer). The product was identified with an authentic sample by thin layer chromatography.

EXAMPLE 55

(1) A solution of 4-nitrobenzyl 7-amino-3-chloro-3-cephem-4-carboxylate hydrochloride (15.0 g.), bis(-trimethylsilyl)acetamide (11.3 g.) and trimethyl-silylacetamide (9.7 g.) in tetrahydrofuran (300 ml.), a solution of diketene (3.41 ml.) in methylene chloride (4 ml.), a solution of bromine (2.27 ml.) in methylene chloride (4 ml.), a solution of sodium nitrite (3.1 g.) in water (20 ml.) and a solution of thiourea (4.0 g.) in water (40 ml.) were treated in a similar manner to that of Example 37-(1) to give 4-nitrobenzyl 7-[2-(2-aminothiazol-4-yl)-2-hydroxyiminoacetamido]-3-chloro-3-cephem-4-carboxylate (syn isomer, 10.4 g.).

I.R. $\nu_{max}^{Nujol}$: 3300, 3180, 1777, 1730, 1670, 1603 cm$^{-1}$.

N.M.R. $\delta$ (DMSO-d$_6$, ppm): 3.93 (2H, d, J=5 Hz), 5.33 (1H, d, J=5 Hz), 5.49 (2H, s), 5.90 (1H, d,d, J=5 Hz, 8.2 Hz), 6.68 (1H, s), 7.14 (1H, broad s), 7.72 (2H, d, J=9.2 Hz), 8.27 (2H, d, J=9.2 Hz), 9.54 (1H, d, J=8.2 Hz).

(2) 4-Nitrobenzyl 7-[2-(2-aminothiazol-4-yl)-2-hydroxyiminoacetamido]-3-chloro-3-cephem-4-carboxylate (syn isomer, 5.0 g.), 10% palladium carbon (3.0 g.), methanol (100 ml.), water (10 ml.) and tetrahydrofuran (150 ml.) were treated in a similar manner to that of Example 37-(2), to give 7-[2-(2-aminothiazol-4-yl)-2-hydroxyiminoacetamido]-3-chloro-3-cephem-4-carboxylic acid (syn isomer, 1.28 g.).

I.R. $\nu_{max}^{Nujol}$: 3330, 1775, 1675, 1630 cm$^{-1}$.

N.M.R. $\delta$ (DMSO-d$_6$, ppm): 3.72 (2H, m), 5.24 (1H, d, J=5 Hz), 5.80 (1H, d,d, J=5.0 Hz, 8.2 Hz), 6.66 (1H, s), 9.50 (1H, d).

EXAMPLE R (1) Ethyl 2-hydroxyimino-3-oxobutyrate (syn isomer, 100 g.), N,N-dimethylformamide (300 ml.), potassium carbonate (130 g.) and bromooctane (121 g.) were treated in a similar manner to that of Example F-(1) to give ethyl 2-n-octyloxyimino-3-oxobutyrate (syn isomer, 165.5 g.), oil.

I.R. $\nu_{max}^{film}$: 1745, 1695, 1470 cm$^{-1}$.

N.M.R. $\delta$ (CCl$_4$, ppm): 0.6~2.1 (18H, m), 2.35 (3H, s), 4.0~4.6 (4H, m)

(2) Ethyl 2-n-octyloxyimino-3-oxobutyrate (syn isomer, 165.5 g.), sulfuryl chloride (84.7 g.) and acetic acid (165 ml.) were treated in a similar manner to that of Example F-(2) to give ethyl 2-n-octyloxyimino-4-chloro-3-oxobutyrate (syn isomer, 169.6 g.), oil.

I.R. $\nu_{max}^{film}$: 1745, 1710, 1465 cm$^{-1}$.

N.M.R. $\delta$ (CCl$_4$, ppm): 0.6~2.1 (18H, m), 4.0~4.6 (4H, m), 4.48 (2H, s).

(3) Ethyl 2-n-octyloxyimino-4-chloro-3-oxobutyrate (syn isomer, 169.6 g.), thiourea (42.3 g.), sodium acetate trihydrate (75.5 g.), water (420 ml.) and ethanol (1020 ml.) were treated in a similar manner to that of Example F-(3) to give ethyl 2-(2-aminothiazol-4-yl)-2-n-octyloxyiminoacetate (syn isomer, 65 g.), mp. 77° to 78° C.

I.R. $\nu_{max}^{Nujol}$: 3470, 3250, 3125, 1735, 1545, 1465 cm$^{-1}$.

N.M.R. $\delta$ (DMSO-d$_6$, ppm): 0.81 (3H, t, J=6Hz), 0.6~1.9 (15H, m), 4.07 (2H, t, J=6 Hz), 4.28 (2H, q, J=7 Hz), 6.86 (1H, s), 7.02 (2H, broad s).

(4) Ethyl 2-(2-aminothiazol-4-yl)-2-n-octyloxy-iminoacetate (syn isomer, 64 g.), 2N-aqueous solution of sodium hydroxide (196 ml.), methanol (196 ml.) and tetrahydrofuran (300 ml.) were treated in a similar manner to that of Example F-(4) to give 2-(2-aminothiazol-4-yl)-2-n-octyloxyiminoacetic acid (syn isomer, 52.5 g.), mp. 146° C. (dec.).

I.R. $\nu_{max}^{Nujol}$: 3170, 1635, 1565, 1460 cm$^{-1}$.

N.M.R. $\delta$ (DMSO-d$_6$, ppm): 0.86 (3H, t, J=6 Hz), 0.6~1.9 (12H, m), 4.06 (2H, t, J=6 Hz), 6.81 (1H, s), 7.22 (2H, s).

(5) 2-(2-Aminothiazol-4-yl)-2-n-octyloxyiminoacetic acid (syn isomer, 20 g.), acetic anhydride (27.3 g.) and formic acid (12.3 g.) were treated in a similar manner to that of Example F-(5) to give 2-(2-formamidothiazol-4-yl)-2-n-octyloxyiminoacetic acid (syn isomer, 21.3 g.), mp. 122° C. (dec.).

I.R. $\nu_{max}^{Nujol}$: 3350, 3150, 3050, 1700, 1675, 1560 cm$^{-1}$.

N.M.R. $\delta$ (DMSO-d$_6$, ppm): 0.6~2.0 (15H, m), 4.16 (2H, t, J=6 Hz), 7.56 (1H, s), 8.57 (1H, s), 12.67 (1H, s).

EXAMPLE 56

(1) A solution of 2-(2-formamidothiazol-4-yl)-2-n-octyloxyiminoacetic acid (syn isomer, 7.52 g.), phosphoryl chloride (5.4 g.) and N,N-dimethylformamide (2.58 g.) in tetrahydrofuran (16 ml.), which was prepared in a similar manner to that of Example 30-(1), and a solution of 7-amino-3-cephem-4-carboxylic acid (4 g.) in a mixture of acetone (20 ml.) water (20 ml.) and tetrahydrofuran (20 ml.) were treated in a similar manner to that of Example 30-(1) to give 7-[2-(2-formamidothiazol-4-yl)-2-n-octyloxyiminoacetamido]-3-cephem-4-carboxylic acid (syn isomer, 8.1 g.).

I.R. $\nu_{max}^{Nujol}$: 3280, 3200, 3060, 1795, 1705, 1660, 1630 cm$^{-1}$.

N.M.R. $\delta$ (DMSO-d$_6$, ppm): 0.6~2.1 (15H, m), 3.62 (2H, d, J=4 Hz), 4.14 (2H, t, J=6 Hz), 5.16 (1H, d, J=5 Hz), 5.88 (1H, d,d, J=5 Hz, 8 Hz), 6.51 (1H, t, J=4 Hz), 7.42 (1H, s), 8.54 (1H, s), 9.63 (1H, d, J=8 Hz), 12.66 (1H, s).

(2) 7-[2-(2-Formamidothiazol-4-yl)-4-n-octylox-yiminoacetamido]-3-cephem-4-carboxylic acid (syn isomer, 8.0 g.), conc. hydrochloric acid (6.23 g.), tetrahydrofuran (15 ml.) and methanol (120 ml.) were treated in a similar manner to that of Example 21-(3) to give 7-[2-(2-aminothiazol-4-yl)-2-n-octyloxyiminoacetamido]-3-cephem-4-carboxylic acid (syn isomer, 6.95 g.).

I.R. $\nu_{max}^{Nujol}$: 3320 (shoulder), 1785, 1660, 1630, 1535.

N.M.R. $\delta$ (DMSO-d$_6$, ppm): 0.6~2.0 (15H, m), 3.62 (2H, broad s), 4.07 (2H, t, J=6 Hz), 5.12 (1H, d, J=5 Hz), 5.83 (1H, d,d, J=5 Hz, 9 Hz), 6.48 (1H, broad s), 6.72 (1H, s), 7.22 (2H, s), 9.53 (1H, d, J=9 Hz).

Preparation S

The following compounds were obtained in any of a similar manner to those of Preparation D.

(1) Ethyl 2-cyclopentyloxyimino-3-oxobutyrate (syn isomer), oil.

I.R. $\nu_{max}^{Film}$: 1740, 1670, 1495, 1430 cm$^{-1}$.

N.M.R. δ(CCl$_4$, ppm): 1.32 (3H, t, J=7 Hz), 1.4–2.2 (8H, m), 2.33 (3H, s), 4.27 (2H, q, J=7 Hz), 4.87 (1H, m).

(2) Ethyl 4-chloro-2 -cyclopentyloxyimino-3-oxobutyrate (syn isomer), oil.

I.R. $\nu_{max}^{Film}$: 1735, 1750, 1465, 1435 cm$^{-1}$.

N.M.R. δ(CCl$_4$, ppm): 1.33 (3H, t, J=7 Hz), 1.3–2.4 (8H, m), 4.28 (2H, q, J=7 Hz), 4.46 (2H, s), 4.86 (1H, s).

(3) Ethyl 2-(2-aminothiazol-4-yl)-2-cyclopentyloxyiminoacetate (syn isomer), mp. 134°–136° C.

I.R. $\nu_{max}^{Nujol}$: 3490, 3450, 3250, 3120, 1735, 1540, 1460 cm$^{-1}$.

N.M.R. δ(DMSO-d$_6$): 1.25 (3H, t, J=7 Hz), 1.62 (8H, broad s), 4.27 (2H, q, J=7 Hz), 4.70 (1H, m), 6.85 (1H, s), 7.20 (2H, s).

(4) 2-(2-Aminothiazol-4-yl)-2-cyclopentyloxyiminoacetic acid (syn isomer), mp. 186° C. (dec.).

I.R. $\nu_{max}^{Nujol}$: 3330, 3120, 1635, 1450 cm$^{-1}$.

N.M.R. δ(DMSO-d$_6$): 1.1–2.2 (8H, m), 4.68 (1H, m), 6.81 (1H, s), 7.18 (2H, broad s).

(5) 2-[2-(2,2,2-trifluoroacetamido) thiazol-4-yl]-3-cyclopentyloxyiminoacetic acid (syn isomer).

I.R. $\nu_{max}^{Nujol}$: 3200, 3130, 1720, 1590, 1580 cm$^{-1}$.

N.M.R. δ(DMSO-d$_6$): 1.34–2.22 (8H, m), 4.81 (1H, m), 7.71 (1H, s).

(6) To acetic anhydride (32 g.) was added formic acid (14.4 g. ) under ice-coolind and stirred at 40° to 45° C. for an hour. 2-(2-Aminothiazol-4-yl)-2-cyclopentyloxyiminoacetic acid (syn isomer, 20 g.) and tetrahydrofuran (100 ml.) were added to the solution under ice-cooling and stirred at 35° C. for 3 hours. After the solution was concentrated in vacuo, the residue was pulverized with diisopropyl ether, and dried over phosphorus pentoxide to give 2-(2-formamidothiazol-4-yl)-2-cyclopentyloxyiminoacetic acid (syn isomer, 9.04 g.), mp. 158° C. (dec.).

I.R. $\nu_{max}^{Nujol}$: 3100, 1730, 1695, 1685, 1550, 1495 cm$^{-1}$.

N.M.R. δ(DMSO-d$_6$): 1.2–2.3 (8H, m), 4.77 (1H, quintet, J=4 Hz), 7.93 (1H, s), 9.37 (1H, s).

EXAMPLE 57

(1) A solution of 2-(2-formamidothiazol-4-yl)-2-cyclopentyloxyiminoacetic acid (syn isomer, 1.5 g.), phosphoryl chloride (974 mg.), N,N-dimethylformamide (464 mg.) and tetrahydrofuran (15 ml.) and a solution of 7-amino-3-cephem-4-carboxylic acid (1.38 g.) in 50% aqueous acetone (14 ml.) were treated in a similar manner to that of Example 15-(1) to give 7-[2-(2-formamidothiazol-4-yl)-2-cyclopentyloxyiminoacetamido]-3-cephem-4-carboxylic acid (syn isomer, 1.75 g.).

I.R. (Nujol): 3270, 3070, 1790, 1690, 1660, 1550 cm$^{-1}$.

N.M.R. (DMSO-d$_6$, ppm):1.2–2.3 (8H, m), 3.59 (2H, d, J=4 Hz), 4,75 (1H, broad s), 5.3 (1H, d, J=5 Hz), 5,54 (1H, dd, J=5 Hz, 8 Hz), 6.48 (1H, t, J=4 Hz), 7.35 (1H, s), 8.50 (1H, s), 9.55 (1H, d, J=8 Hz), 12.56 (1H, broad s).

7-[2-(2-formamidothiazol-4-yl)-2cyclopentyloxyiminoacetamido]-3-cephem-4-carboxylic acid (syn isomer, 1.7 g.) in methanol (17 ml.) and tetrahydrofuran (5 ml.), and conc. hydrochloric acid (1.5 g.) were treated in a similar manner to that of Example 15-(3) to give 7-[2-(2-aminothiazol-4-yl)-2cyclopentyloxyiminoacetamido]-3cephem-4-carboxylic acid (syn isomer, 1.3 g.).

I.R. (Nujol): 3280, 1765, 1655, 1620, 1530 cm$^{-1}$.

N.M.R. (DMSO-d$_6$, ppm): 1.1–2.2 (8H, m), 4.66 (1H, broad s), 5.08 (1H, d, J=5 Hz), 5.80 (1H, dd, J=5 Hz, 8 Hz), 6.44 (1H, t, J=4 Hz), 6.67 (1H, s), 7.14 (2H, s), 9.43 (1H, d, J=8 Hz).

What we claim is:

1. The compound 7-[2-(2-aminothiazol-4-yl)-2-cyclopentyloxyiminoacetamido]-3-cephem-4-carboxylic acid (syn isomer).

* * * * *

UNITED STATES PATENT AND TRADEMARK OFFICE
CERTIFICATE OF CORRECTION

PATENT NO. : 4,294,960
DATED : Oct. 13, 1981
INVENTOR(S) : TAKAO TAKAYA ET AL

It is certified that error appears in the above-identified patent and that said Letters Patent are hereby corrected as shown below:

Please correct the Priority Data to read as follows:

[30]---Foreign Application Priority Data

Mar. 14, 1977 [GB]  United Kingdom......10699/77

Jul. 12, 1977 [GB]  United Kingdom......29245/77

Oct. 11, 1977 [GB]  United Kingdom......42315/77

Jan. 3, 1978 [GB]  United Kingdom......75/77

Rather than

[30]---Foreign Application Priority Data

Mar. 14, 1977 [GB]  United Kingdom......10699/77

Jul. 12, 1977 [GB]  United Kingdom......29245/77

Nov. 11, 1977 [GB]  United Kingdom......42315/77

As it now appears.

Signed and Sealed this

Twenty-sixth Day of January 1982

[SEAL]

Attest:

*Attesting Officer*

GERALD J. MOSSINGHOFF

*Commissioner of Patents and Trademarks*